US012186380B2

(12) United States Patent
Werner

(10) Patent No.: US 12,186,380 B2
(45) Date of Patent: Jan. 7, 2025

(54) ***PLASMODIUM FALCIPARUM* AND *PLASMODIUM VIVAX* VACCINE**

(71) Applicant: Ekkehard Werner, Heidelberg (DE)

(72) Inventor: Ekkehard Werner, Heidelberg (DE)

( * ) Notice: Subject to any disclaimer, the term of this patent is extended or adjusted under 35 U.S.C. 154(b) by 0 days.

(21) Appl. No.: 16/615,490

(22) PCT Filed: May 24, 2018

(86) PCT No.: PCT/EP2018/063703
§ 371 (c)(1),
(2) Date: Nov. 21, 2019

(87) PCT Pub. No.: WO2018/215612
PCT Pub. Date: Nov. 29, 2018

(65) Prior Publication Data

US 2020/0113988 A1 Apr. 16, 2020
US 2020/0261561 A9 Aug. 20, 2020

(30) Foreign Application Priority Data

May 24, 2017 (DE) ........................ 102017004987.4

(51) Int. Cl.
*A61K 39/015* (2006.01)
*C07K 16/20* (2006.01)
*C12N 15/70* (2006.01)
*G01N 33/569* (2006.01)

(52) U.S. Cl.
CPC .......... *A61K 39/015* (2013.01); *C07K 16/205* (2013.01); *C12N 15/70* (2013.01); *G01N 33/56905* (2013.01); *G01N 2333/445* (2013.01); *G01N 2800/26* (2013.01)

(58) Field of Classification Search
None
See application file for complete search history.

(56) References Cited

U.S. PATENT DOCUMENTS 8,716,443 B2 * 5/2014 Druilhe ................ A61K 39/015
530/350
2006/0188527 A1 * 8/2006 Hoffman .............. C07K 14/445
424/272.1

FOREIGN PATENT DOCUMENTS

WO 00/25728 A2 5/2000
WO 2009/136373 A1 11/2009
WO 2011/119484 A1 9/2011

OTHER PUBLICATIONS

Voepel et al. 2014 (Malaria vaccine candidate antigen targeting the pre-erythrocytic stage of Plasmodium falciparum produced at high level in plants; Biotechnology Journal; vol. 9, No. 11, 1, pp. 1435-1445) (Year: 2014).*

Harini De Silva et al. 2011 (The antibody response to Plasmodium falciparum Merozoite Surface Protein 4: comparative assessment of specificity and growth inhibitory antibody activity to infection-acquired and immunization-induced epitopes; Malaria Journal, vol. 10, No. 1, p. 266) (Year: 2011).*

Greenspan et al. 1999 (Defining epitopes: It's not as easy as it seems; Nature Biotechnology, 17:936-937). (Year: 1999).*

Rosenthal et al. 2019 (Malaria: How are we doing and how can we do better?; Am. J. Trop. Med. Hyg. 100(2): 239-241). (Year: 2019).*

Werner Ebe, William WR Taylor, Holder AA. (1998) A Plasmodium chabaudi protein contains a repetitive region with a predicted spectrin-like structure. Mol Biochem Parasitol. 94:185-196.

Topolska AE, Richie TL, Nhan DH, Coppel, RL. (2004), Associations between responses to the rhoptry-associated membrane antigen of Plasmodium falciparum and immunity to malaria infection. Infect Immun 72(6):3325-3330.

Villard V, Agak GW, Frank G, Jafarshad A, Servis C, Servis C, Nébié I, Sirima SB, Felger I, Arevalo-Herrera M, Herrera S, Heitz F, Bäcker V, Druilhe P, Kajava AV, Corradin G (2007) Rapid identification of malaria vaccine candidates based on alpha-helical coiled coil protein motif. PLoS One, Issue 7, e645.

Watier H, Verwaerde C, Landau I, Werner E, Fontaine J, Capron A, Auriault C (1992). T-cell dependent immunity and thrombocytopenia in rats infected with Plasmodium chabaudi. Infect Immune, 60:136-142.

Leslie, M. (2013) Solution to Vaccine Mystery Starts to Crystallize. Science 341:26-27.

Wang Y, Wang G, Cai JP (2016) Identifying Novel B Cell Epitopes within Toxoplasma gondii GRA6. Korean J Parasitol. 54(4):431-437 (English. https://doi.org/10.3347/kjp.2016.54.4.431).

Garnier J, Robson B (1989) The GOR method for predicting secondary structures in proteins. In Fasman GD ed., Prediction of protein structure and the principles of protein conformation. New York, USA. Plenum Press. pp. 417-465.

Chou PY, Fasman GD (1978) Prediction of the secondary structure of proteins from their amino acid sequence. Adv Enzymol 47:45-148.

Kyte J, Doolittle RF. (1982) A simple method for displaying the hydro¬pathic character of a protein. J Mol Biol 157:105-132.

Garnier et al., GOR Method for Predicting Protein Secondary Structure from Amino Acid Sequence; Methods in Ezymology, vol. 266, pp. 540-553.

(Continued)

*Primary Examiner* — Mary Maille Lyons
(74) *Attorney, Agent, or Firm* — RAPHAEL BELLUM PLLC

(57) ABSTRACT

The present invention relates to a vaccine V comprising (A) at least one isolated polypeptide strand P comprising or consisting of at least nine consecutive amino acid moieties of the repetitive organellar protein, putative of *Plasmodium falciparum* or the hypothetical protein PVNG_04523 of *Plasmodium vivax* or a polynucleotide strand encoding for such polypeptide; and (B) at least one pharmaceutically acceptable carrier or excipient. Furthermore, the present invention refers to an antibody binding to the repetitive organellar protein, putative of *Plasmodium falciparumor* the hypothetical protein PVNG_04523 of *Plasmodium vivax* or a polynucleotide strand encoding therefor, to a method of generating such antibody and uses thereof.

8 Claims, No Drawings

Specification includes a Sequence Listing.

(56) References Cited

OTHER PUBLICATIONS

Karplus PA, Schulz GE. (1985) Prediction of chain flexibility in proteins: tool for the selection of peptide antigens. Naturwissenschaften 72:212-213.
Emini EA, Hughes JV, Perlow DS, Boger J (1985) Induction of hepatitis A virus-neutralizing antibody by virus specific synthetic peptide. J Virol 55:836-839.
Jameson BA, Wolf (1988) The antigenic index: a novel algorithm for predicting antigenic determinants. Comput Appl Biosci 4(1):181-186.
Kugler J, Wilke S, Meier D, Tomszak F, Frenzel A, Schirrmann T, Dübel S, Garritsen H, Hock B, Toleikis L, Schütte M, Hust M (2015) Generation and analysis of the improved human HAL9/10 antibody phage display libraries Biotechnology 15:10 ; DOI 10.1186/s12896-015-0125-0.
Jäger V, Büssow K, Wagner A, Weber S, Hust M, Frenzel A and Schirrmann (2013) High level transient production of recombinant antibodies and antibody fusion proteins in HEK293 cells. BMC Biotechnology 13:52, 1472-6750/13/52.
Kennedy MC, Jin Wang, Yanling Zhang, Miles AP, Chitsaz F, Saul A, Long CA, Miller LH, Stowers AW (2002) In vitro studies with recombinant Plasmodium falciparum apical membrane antigen 1 (AMA1): Production and activity of an AMA1 vaccine and generation of a multiallelic response. Infect Immun 70(12):6948-6960.
Stadler V et al. (2008) Combinatorial synthesis of peptide arrays with a laser printer. Angew. Chem. Int. Ed. Engl. 47 (37):7132-7135.
Voepel n et al.: "Malaria vaccine candidate antigen targeting the pre-erythrocytic stage of Plasmodium produced at high level in plants", Biotechnology Journal, Wiley-VCH Verlag, Weinheim, DE, vol. 9, No. 11, 2014, pp. 1435-1445.
Harini D De Silva et al.: "The antibody response to Plasmodium falciparum Merozoite Surface Protein 4: comparative assessment of specificity and growth inhibitory-aquired and immunization-induced epitopes", Malaria Journal, Biomed Central, London, GB, 2011, vol. 10, No. 1:266.
Kulangara, C., A. V. Kajava, G. Corradin, and I. Felger (2009) Sequence conservation in Plasmodium falciparum alpha-helical coiled coil domains proposed for vaccine development. PLoS One 4:e5419.
International Preliminary Report on Patentability in International Application No. PCT/EP2018/063703, dated Dec. 5, 2019.
"Plasmodium falciparum 3D7 PFB0145C protein, p8, SEQ ID 35.", XP055812228, retrieved from EBI accession No. GSP:AXS80015 Database accession No. AXS80015 database Geneseq, May 13, 2010, XP055812228, accession No. AXS80015.
Database Geneseq [Online] Jun. 24, 2012, "peptide; 27 AA.", XP055812255, retrieved from EBI accession No. GS_PROT_ALERT:WO2011119484.3324518; Database accession No. WO2011119484.3324518.

* cited by examiner

SEQUENCE LISTING

```
<160> NUMBER OF SEQ ID NOS: 25

<210> SEQ ID NO 1
<211> LENGTH: 1939
<212> TYPE: PRT
<213> ORGANISM: Plasmodium chabaudi

<400> SEQUENCE: 1

Met Ile Phe Asn Leu Lys Lys Ser Lys Lys Asn Glu Asp Gly Ser Asn
1               5                   10                  15

Lys Asp Ser Lys Lys Thr Asn Glu Thr Ser Gly Ile Glu Lys Lys Glu
            20                  25                  30

Lys Ser Asn Lys Trp Tyr Asn Lys Ile Val Asn Asn Ser Thr Lys Lys
        35                  40                  45

Asp Lys Asp Lys Asn Asn Asp Ser Ile Val Tyr Asp Asp Glu Ser Lys
    50                  55                  60

Val Gly Glu Asn Asp His His Met Lys Glu Tyr Glu Leu Glu Asp Gln
65                  70                  75                  80

Leu Lys Glu Thr Leu Lys Ser Ile Thr Ala Leu Ser Ile Lys Val Lys
                85                  90                  95

Glu Tyr Glu Val Lys Ile Glu Glu Leu Glu Lys Glu Leu Lys Leu Glu
            100                 105                 110

Lys Glu Lys Gln Ile Asn Lys Glu Tyr Glu Lys Glu Leu Asn Glu Lys
        115                 120                 125

Ser Glu Phe Ile Lys Arg Gln Met Glu Leu Leu Lys Glu Lys Glu Leu
    130                 135                 140

Asn Ile Asn Leu Lys Glu Asn Lys Ile Asn Asn Lys Glu Ile Ile Thr
145                 150                 155                 160

Leu Lys Arg Glu Glu Lys Leu Asn Asp Ile Glu Ser Glu Tyr Ile Glu
                165                 170                 175

Lys Asn Lys Glu Lys Glu Lys Leu Asn Tyr Glu Val Thr Asn Ile Lys
            180                 185                 190

Met Ser Leu Asp Lys Leu Thr Cys Glu Val Gln Glu Lys Lys Asp Asn
        195                 200                 205

Leu Glu Lys Ile Asn Lys Lys Val Ile Glu Lys Glu Asn Asn Leu Arg
    210                 215                 220

Glu Leu Lys Glu Phe Met Lys Glu Lys Asn Glu Ile Ile Glu Ser Leu
225                 230                 235                 240

Asp Gly Thr Ile Asn Asp Lys Lys Asn Ala Tyr Glu Lys Leu Glu Ile
```

-continued

```
                245                 250                 255

Ser Phe Glu Glu Lys Arg Lys Met Ile Glu Met Leu Asp Ser Lys Leu
            260                 265                 270

Ile Glu Lys Glu Glu Asn Phe Ala Asn Lys Gln Ala Lys Leu Glu Lys
        275                 280                 285

Glu Asn Glu Ile Ile Ile Glu Lys Leu Lys Asp Ile Glu Ser Arg Glu
    290                 295                 300

Lys Asp Phe Lys Ser Lys Glu Glu Lys Phe Ala Ser Met Glu Asn Glu
305                 310                 315                 320

Leu Asn Thr Leu Lys Ser Asp Leu Ser Lys Asn Ala Cys Gln Met Glu
                325                 330                 335

Val Tyr Lys Leu Glu Ile Lys Asp Leu Ser Gln Ser Leu Val Glu Lys
            340                 345                 350

Glu Arg Glu Ile Phe Glu Ile Lys Asn Glu Tyr Asp Asp Lys Ile Asn
        355                 360                 365

Asn Met Lys Glu Lys Leu Ser Ser Ile Asn Asp Lys Gly Ile Asp Asn
    370                 375                 380

Thr Val Leu His Ser Glu Glu Glu Lys Ile Asn Lys Leu Leu Lys Glu
385                 390                 395                 400

Lys Glu Thr Glu Leu Asn Glu Ile His Lys Lys Tyr Asn Leu Glu Ile
                405                 410                 415

Glu Thr Ile Lys Asn Glu Leu Asn Glu Lys Glu Glu Glu Leu Glu Lys
            420                 425                 430

Asn Lys Lys Ala His Thr Val Glu Val Thr Asn Leu Thr Lys Glu Ile
        435                 440                 445

Lys Leu Leu Glu Lys Lys Thr Glu Asp Ala Lys Glu Gly His Lys Asn
    450                 455                 460

Glu Leu Asn Glu Leu Asn Asn Gln Leu Ser Lys Leu Asn Lys Glu Lys
465                 470                 475                 480

Asp Asn Ile Lys Asn Glu Asn Thr Glu Leu Asn Asp Lys Ile Ser Ser
                485                 490                 495

Leu Asn Ser Glu Val Asn Ile Leu Asn Lys Asp Lys Gln Thr Leu Gly
            500                 505                 510

Asn Asp Ile Lys Thr Leu Asn Asp Leu Ile Asn Asn Leu Lys Asn Glu
        515                 520                 525

Ile Asn Thr Ser Asp Asn Lys Met Asn Lys Met Lys Glu Asp Leu Ala
    530                 535                 540

Met Leu Asn Glu Glu Met Glu Gly Lys Cys Val Val Ile Asp Glu Ile
545                 550                 555                 560

Glu Lys Lys Tyr Lys Asn Glu Ile Phe Met Leu Glu Glu Lys Leu Lys
                565                 570                 575

Glu Lys Glu Asn Tyr Ala Asp Leu Asn Asp Glu Ile Ser Ile Leu Arg
            580                 585                 590

Asn Ser Ile Tyr Val Lys Glu Lys Glu Phe Ile Glu Met Lys Glu Phe
        595                 600                 605

Tyr Glu Asn Lys Ile Asn Leu Phe Asn Lys Asn Phe Glu Glu Lys Lys
    610                 615                 620

Asn Ile Tyr Glu Asn Glu Leu Asn Ser Leu Arg Leu Lys Tyr Asp Asn
625                 630                 635                 640

Glu Gln Gly Leu Ile Lys Gln Ile Asp Glu Leu Asn Ile Gln Lys Leu
                645                 650                 655

Lys Thr Glu Glu Lys Tyr Leu Gln Leu Tyr Asn Asp Asn Met His Met
            660                 665                 670
```

```
Phe Arg Ser Ile Cys Thr Lys Ile Asp Met Pro Tyr Ser Glu Asn Ile
        675                 680                 685

Lys Gly Ser Asp Leu Val Asp Phe Val Thr Ala Tyr Ile Lys Arg Arg
    690                 695                 700

Asp Glu Ser Ser Ser Asp Ala Asn Pro Asp Thr Thr His Lys Glu Met
705                 710                 715                 720

Val Ala Glu Leu Glu Lys Arg His Ala Ala Ile Val Ala Glu Leu Glu
                725                 730                 735

Glu Lys His Lys Glu Glu Ile Ala Lys Leu Gly Glu Gly His Lys Glu
            740                 745                 750

Val Val Leu Arg Leu Gly Glu Gln His Lys Glu Glu Thr Ile Ile Leu
        755                 760                 765

Glu Glu Lys His Lys Asp Val Val Thr Lys Leu Gly Glu Gln His Lys
    770                 775                 780

Glu Asn Ile Ile Lys Leu Glu Glu Glu His Lys Asp Val Val Thr Lys
785                 790                 795                 800

Leu Gly Asp Gln Tyr Lys Glu Glu Ile Ala Lys Leu Lys Glu Glu His
                805                 810                 815

Ala Val Val Val Ala Glu Leu Glu Glu Lys His Lys Leu Gly Glu Gly
            820                 825                 830

His Lys Glu Met Val Asp Glu Leu Glu Lys Arg His Ala Asp Phe Val
        835                 840                 845

Glu Gly Leu Glu Glu Lys His Lys Ala Glu Thr Ala Lys Leu Glu Glu
    850                 855                 860

Gly His Lys Ser Glu Met Asn Glu Val Glu Lys Arg His Ala Asp Phe
865                 870                 875                 880

Val Glu Gly Leu Glu Glu Lys His Lys Ala Glu Thr Ala Lys Leu Gly
                885                 890                 895

Glu Gly His Arg Glu Val Val Ala Gly Leu Glu Glu Lys His Lys Glu
            900                 905                 910

Val Val Ala Glu Leu Glu Glu Lys His Lys Glu Glu Ile Ala Lys Leu
        915                 920                 925

Glu Glu Gly His Lys Glu Val Met Ala Glu Leu Gly Glu Lys His Lys
    930                 935                 940

Glu Val Val Ala Gly Leu Glu Ala Lys His Asn Leu Glu Glu Gly His
945                 950                 955                 960

Lys Glu Met Val Ala Glu Leu Glu Lys Arg His Ala Asp Leu Val Ala
                965                 970                 975

Val Leu Glu Glu Gln His Lys Ala Glu Ile Ile Lys Leu Gly Glu Glu
            980                 985                 990

His Lys Glu Val Val Ala Gly Ile  Glu Glu Lys Tyr Lys  Val Glu Ala
        995                 1000                1005

Ile Lys  Leu Ala Glu Glu His  Lys Asp Val Val Thr  Lys Leu Gly
    1010                1015                1020

Glu Gln  His Lys Glu Glu Ile  Ala Lys Leu Glu Asp  Gly His Lys
    1025                1030                1035

Glu Val  Val Asn Glu Val Glu  Lys Lys Asn Ala Ser  Leu Leu Asn
    1040                1045                1050

Met Leu  Glu Glu Asn His Lys  Asn Glu Met Ile Lys  Leu Lys Glu
    1055                1060                1065

Glu His  Lys Glu Ser Ala Ser  Asp Leu Val Glu Lys  Leu Tyr Gln
    1070                1075                1080
```

```
Lys Asp  Glu Glu Val Lys Asn  Ser Asn Asn Lys Ile  Glu Glu Leu
    1085                 1090                 1095

Thr Asn  Val Ile Lys Asp Leu  Asn Asp Ser Ile Met  Cys Tyr Lys
    1100                 1105                 1110

Lys Gln  Ile Leu Glu Glu Val  Glu Lys Arg Asn Glu  Tyr Asn Glu
    1115                 1120                 1125

Glu Ile  Asn Lys Leu Lys Ile  Val Gln Asn Glu Met  Lys Asp Met
    1130                 1135                 1140

Asn Asp  Lys Lys Ile Leu Glu  Lys Glu Asn Glu Ile  Lys Lys Leu
    1145                 1150                 1155

Asn Lys  Lys Leu Ser Asn Tyr  Lys Val Phe Glu Thr  Lys Glu Asn
    1160                 1165                 1170

Thr Tyr  Lys Asn Ser Glu Met  Val Val Asn Glu Asn  Lys Glu Arg
    1175                 1180                 1185

Ile Ile  Val Asp Ser Val Cys  Lys Glu Asn Ile Ser  Glu Ser Asp
    1190                 1195                 1200

Val Glu  Gly Lys Gly Gly Asn  Leu Lys Met Thr Leu  Ser Leu Lys
    1205                 1210                 1215

Lys Lys  Glu Arg Asn Ile Phe  Ser Ile Asn Asp Asn  Lys Asn Glu
    1220                 1225                 1230

Ser Ser  Glu Leu Val Asp Thr  Ile Lys Ser Ala Tyr  Ile Asn Lys
    1235                 1240                 1245

Ile Glu  Met Tyr Lys Lys Glu  Ile Glu Asp Asn Gly  Lys Asn Ile
    1250                 1255                 1260

Glu Asp  Leu Lys Asn Lys Ile  Leu Asp Leu Ser Asn  Glu Leu Ile
    1265                 1270                 1275

Asn Leu  Glu Asn Met Lys Asn  Val Leu Thr Asp Glu  Asn Asn Asn
    1280                 1285                 1290

Leu Lys  Lys Glu Ile Glu Ile  Lys Asp Asn Lys Leu  Asn Glu Lys
    1295                 1300                 1305

Glu Lys  Asn Glu Asn Thr Glu  Ile Leu Asn Leu Asn  Asp Asp Ile
    1310                 1315                 1320

Ile Lys  Leu Lys Lys Glu Ile  Ser Glu Trp Lys Asp  Glu Glu Glu
    1325                 1330                 1335

Lys Leu  Thr Lys Glu Asn Ile  Lys Leu Lys Asn Asp  Ile Glu Gln
    1340                 1345                 1350

Ile Asn  Lys Glu Tyr Lys Ile  Lys Glu Glu Asn Leu  Met Ile Lys
    1355                 1360                 1365

Phe Asn  Glu Asn Ile Asn Glu  Val Thr Ser Leu Lys  Asn Gln Ile
    1370                 1375                 1380

Glu Ile  Glu Lys Met Lys Leu  Glu Glu Leu Asn Lys  Asn Tyr Glu
    1385                 1390                 1395

Leu Leu  Leu Ala Glu Lys Arg  Glu Thr Asn Met Ser  Ile Ser Asn
    1400                 1405                 1410

Asp Asp  Asn Lys Ile Val Glu  Asn Asn Ile Leu Glu  Asp Thr Asp
    1415                 1420                 1425

Ser Lys  Gln Asn Asn Leu Asn  Lys Asn Val Glu Asp  Lys Thr Gly
    1430                 1435                 1440

Asp Asp  Ile Asn Cys Glu Lys  Asn Asn Asp Gln Ala  Lys Glu Ile
    1445                 1450                 1455

Ser Tyr  Leu Lys Asp Glu Ile  Lys Lys Ile Ser Met  Leu Tyr Gly
    1460                 1465                 1470

Glu Glu  Leu Asn Arg Lys Asn  Ser Tyr Asp Glu Lys  Val Lys Asn
```

```
    1475                1480                1485

Leu Thr  Asn Glu Leu Lys Glu  Leu Lys Ile Arg Asn  Lys Lys Gly
    1490                1495                1500

Glu Glu  Ala Ile Ala Glu Leu  Asn Lys Leu Lys Asn  Ile Lys Glu
    1505                1510                1515

Lys Asn  Lys Ser Val Lys Gln  Asn Asp Glu Ser Ser  Ser Asn Asn
    1520                1525                1530

Ile Ile  Thr Lys Asp Gly Asp  Lys Thr Pro Glu Tyr  Val Ser Asn
    1535                1540                1545

Asp Asp  Lys Ile Gln Lys Asp  Trp Lys Ala Asn Leu  Val Leu Lys
    1550                1555                1560

Leu Lys  Glu Lys Pro Asp Leu  Trp Asp Asn Ile Asn  Ser Leu Glu
    1565                1570                1575

Lys Glu  Asn Phe Arg Val Met  Ser Ile Val Lys Glu  Asn Lys Asn
    1580                1585                1590

Val Gln  Asn Asp Lys Ile Val  Gly Ile Tyr Ser Tyr  Phe Lys Lys
    1595                1600                1605

Cys Glu  Lys Glu Leu Lys Asn  Asp Met Leu Val Ile  Cys Leu Val
    1610                1615                1620

Leu Lys  Asp Ile Leu Ser Ile  Leu Phe Leu Asn Asp  Asn Phe Val
    1625                1630                1635

Asn Leu  Phe Glu Lys Ile Asp  Lys Ile Leu Trp Lys  Gln Met Tyr
    1640                1645                1650

Ile Pro  Thr Glu Ile Arg Ile  Leu Phe Leu Arg Tyr  Phe Ser Phe
    1655                1660                1665

Leu Asp  Lys Leu Arg Asn Tyr  Val Lys Cys Val Asn  Glu Glu Tyr
    1670                1675                1680

Val Asn  Asn Glu Arg Tyr Glu  Tyr Ser Trp Ala Leu  Phe Gln Thr
    1685                1690                1695

Tyr Leu  Glu Thr Ala Ser Asn  Leu Lys Lys Glu Met  Ile Tyr Tyr
    1700                1705                1710

Val Leu  Glu Lys Ala Glu Lys  Asp Ser Cys Glu Asn  Asn Ser Ser
    1715                1720                1725

Asn Phe  Asp Lys Pro Lys Ile  Thr Asp Ile Leu Asn  Phe Ser Lys
    1730                1735                1740

Asp Ser  Ile Arg Leu Lys Thr  Ile Ala Gln Leu Arg  Lys Glu Leu
    1745                1750                1755

Asn Phe  Glu Arg Glu Ala Lys  Asn Ile Leu Asn Tyr  Asp Tyr Gln
    1760                1765                1770

Ile Ile  Leu Asn Lys Tyr His  Glu Cys Leu Arg Lys  Leu Lys Ile
    1775                1780                1785

Val Lys  Asn Met Ala Arg Glu  Leu Asp Phe Asn Tyr  Asn Val Ser
    1790                1795                1800

Ser Lys  Phe Ser Ile Lys Lys  Glu Leu Glu Met Cys  Ser Asp Glu
    1805                1810                1815

Asn Asp  Glu Phe Lys Tyr Asn  Asn Ile Lys Asn Asn  Glu Glu Lys
    1820                1825                1830

Asn Asp  Thr Ile Lys Asp Pro  Lys His Asn Asn Leu  Ile Gln Lys
    1835                1840                1845

Ile Ile  Asn Leu Gln Arg Asn  Lys Lys Thr Glu Lys  Lys Lys Asn
    1850                1855                1860

Asn Leu  Val Asn Glu Ile Asn  Thr Met Tyr Pro Gly  Asp Thr Thr
    1865                1870                1875
```

```
Pro Lys  Gly Lys Ile Phe Thr  Thr Asn Asp Asn Ser  Lys Gln Asn
    1880                 1885                 1890

Glu Ile  Leu Lys Lys Lys Asp  Asn Ile Asn Asn Asn  Ile Thr His
    1895                 1900                 1905

Lys Asn  Val Tyr Thr Gly Gln  Val Lys Asn Ile Phe  Asn Glu Pro
    1910                 1915                 1920

Val Glu  Arg Lys Val Arg Ile  Ser Phe Ile His Lys  Ser Pro Phe
    1925                 1930                 1935

Asn


<210> SEQ ID NO 2
<211> LENGTH: 1979
<212> TYPE: PRT
<213> ORGANISM: Plasmodium falciparum

<400> SEQUENCE: 2

Met Val Phe Thr Phe Lys Asn Lys Lys Lys Lys Lys Glu Ala Ser Ser
1               5                   10                  15

Asp Lys Val Ser Lys Glu Ser Phe Asn Glu Glu Asp Asn Glu Asn Asn
            20                  25                  30

Glu Lys Arg Glu Lys Ser Asp Ser Trp Tyr Lys Lys Ile Ile Glu Thr
        35                  40                  45

Lys Gly Lys Ser Lys Thr Lys Tyr Lys Asn Asp Asn Ser Leu Asp Asp
    50                  55                  60

Asn Ile Asn Glu Asp Ile Ile Asn Asn Asn Asn Asn Asn Asn Asn Asp
65                  70                  75                  80

Asn Asn Asn Asp Asn Asn Asn Asp Asn Asn Asn Asp Asn Asn Asn Asp
                85                  90                  95

Asn Asn Asn Asp Asn Asn Asn Glu Asn Asn Asn Asp Asn Asn Asn Phe
            100                 105                 110

Asn Asn Tyr Ser Asp Glu Ile Ser Lys Asn Ile Ile His Lys Asp Asn
        115                 120                 125

Glu Leu Glu Asn Gln Leu Lys Asp Thr Leu Lys Ser Ile Ser Ser Leu
    130                 135                 140

Ser Asn Lys Ile Val Asn Tyr Glu Ser Lys Ile Glu Glu Leu Glu Lys
145                 150                 155                 160

Glu Leu Lys Glu Val Lys Asp Lys Asn Ile Asp Asn Asn Asp Tyr Glu
                165                 170                 175

Asn Lys Leu Lys Glu Lys Glu Asp Phe Val Lys Gln Lys Ile Asp Met
            180                 185                 190

Leu Asn Glu Lys Glu Asn Leu Leu Gln Glu Lys Glu Leu Asp Ile Asn
        195                 200                 205

Lys Arg Glu Lys Lys Ile Asn Glu Lys Glu Lys Asn Ile Ile Lys Lys
    210                 215                 220

Glu Glu Thr Phe His Asn Ile Glu Lys Glu Tyr Leu Glu Lys Asn Lys
225                 230                 235                 240

Glu Arg Glu Thr Ile Ser Ile Glu Ile Ile Asp Ile Lys Lys His Leu
                245                 250                 255

Glu Lys Leu Lys Ile Glu Ile Lys Glu Lys Lys Glu Asp Leu Glu Asn
            260                 265                 270

Leu Asn Lys Lys Leu Leu Ser Lys Glu Asn Val Leu Lys Glu Leu Lys
        275                 280                 285

Gly Cys Val Lys Glu Lys Asn Glu Thr Ile Asn Ser Leu Asn Asp Asn
    290                 295                 300
```

```
Ile Ile Glu Lys Glu Lys Lys Tyr Lys Leu Leu Glu Tyr Glu Leu Glu
305                 310                 315                 320

Glu Lys Asn Lys Gln Ile Asp Leu Leu Asn Lys Gln Glu Lys Glu Lys
                325                 330                 335

Glu Lys Glu Lys Glu Arg Glu Lys Glu Lys Glu Arg Glu Lys Glu Lys
            340                 345                 350

Glu Lys Glu Tyr Asp Thr Leu Ile Lys Glu Leu Lys Asp Glu Lys Ile
        355                 360                 365

Ser Ile Leu Glu Lys Val His Ser Ile Lys Val Arg Glu Met Asp Ile
    370                 375                 380

Glu Lys Arg Glu His Asn Phe Leu His Met Glu Asp Gln Leu Lys Asp
385                 390                 395                 400

Leu Lys Asn Ser Phe Val Lys Asn Asn Asn Gln Leu Lys Val Tyr Lys
                405                 410                 415

Cys Glu Ile Lys Asn Leu Lys Thr Glu Leu Glu Lys Lys Glu Lys Glu
            420                 425                 430

Leu Lys Asp Ile Glu Asn Val Ser Lys Glu Glu Ile Asn Lys Leu Ile
        435                 440                 445

Asn Gln Leu Asn Glu Lys Glu Lys Gln Ile Leu Ala Phe Asn Lys Asn
    450                 455                 460

His Lys Glu Glu Ile His Gly Leu Lys Glu Glu Leu Lys Glu Ser Val
465                 470                 475                 480

Lys Ile Thr Lys Ile Glu Thr Gln Glu Leu Gln Glu Met Val Asp Ile
                485                 490                 495

Lys Gln Lys Glu Leu Asp Gln Leu Gln Glu Lys Tyr Asn Ala Gln Ile
            500                 505                 510

Glu Ser Ile Ser Ile Glu Leu Ser Lys Lys Glu Lys Glu Tyr Asn Gln
        515                 520                 525

Tyr Lys Asn Thr Tyr Ile Glu Glu Ile Asn Asn Leu Asn Glu Lys Leu
    530                 535                 540

Glu Glu Thr Asn Lys Glu Tyr Thr Asn Leu Gln Asn Asn Tyr Thr Asn
545                 550                 555                 560

Glu Ile Asn Met Leu Asn Asn Asp Ile His Met Leu Asn Gly Asn Ile
                565                 570                 575

Lys Thr Met Asn Thr Gln Ile Ser Thr Leu Lys Asn Asp Val His Leu
            580                 585                 590

Leu Asn Glu Gln Ile Asp Lys Leu Asn Asn Glu Lys Gly Thr Leu Asn
        595                 600                 605

Ser Lys Ile Ser Glu Leu Asn Val Gln Ile Met Asp Leu Lys Glu Glu
    610                 615                 620

Lys Asp Phe Leu Asn Asn Gln Ile Val Asp Leu Ser Asn Gln Ile Asp
625                 630                 635                 640

Leu Leu Thr Arg Lys Met Glu Glu Lys Glu Asn Lys Met Leu Glu Gln
                645                 650                 655

Glu Asn Lys Tyr Lys Gln Glu Met Glu Leu Leu Arg Gly Asn Ile Lys
            660                 665                 670

Ser Ser Glu Asn Ile Leu Asn Asn Asp Glu Glu Val Cys Asp Leu Lys
        675                 680                 685

Arg Lys Leu Ser Leu Lys Glu Ser Glu Met Lys Met Met Lys Glu Glu
    690                 695                 700

His Asp Lys Lys Leu Ala Glu Leu Lys Asp Asp Cys Asp Val Arg Ile
705                 710                 715                 720
```

```
Arg Glu Met Asn Glu Lys Asn Glu Asp Lys Ile Asn Met Leu Lys Glu
                725                 730                 735

Glu Tyr Glu Asp Lys Ile Asn Thr Leu Lys Glu Gln Asn Glu Asp Lys
            740                 745                 750

Ile Asn Thr Leu Lys Glu Gln Asn Glu Asp Lys Ile Asn Thr Leu Lys
        755                 760                 765

Glu Glu Tyr Glu His Lys Ile Asn Thr Met Lys Glu Glu Tyr Glu His
    770                 775                 780

Lys Ile Asn Thr Leu Asn Glu Gln Asn Glu His Lys Ile Asn Thr Leu
785                 790                 795                 800

Asn Glu Gln Asn Glu His Lys Ile Asn Thr Met Lys Glu Glu Tyr Glu
                805                 810                 815

Asp Lys Met Asn Thr Leu Asn Glu Gln Asn Glu Asp Lys Met Asn Ser
            820                 825                 830

Leu Lys Glu Glu Tyr Glu Asn Lys Ile Asn Gln Ile Asn Ser Asn Asn
        835                 840                 845

Glu Ile Lys Ile Lys Asp Val Val Asn Glu Tyr Ile Glu Glu Val Asp
    850                 855                 860

Lys Leu Lys Val Thr Leu Asp Glu Lys Lys Lys Gln Phe Asp Lys Glu
865                 870                 875                 880

Ile Asn Tyr Ala His Ile Lys Ala His Glu Lys Glu Gln Ile Leu Leu
                885                 890                 895

Thr Glu Met Glu Glu Leu Lys Cys Gln Arg Asp Asn Lys Tyr Ser Asp
            900                 905                 910

Leu Tyr Glu Lys Tyr Ile Lys Leu Ile Lys Ser Ile Cys Met Ile Ile
        915                 920                 925

Asn Ile Glu Cys Cys Asp Asp Ile Glu Asn Glu Asp Ile Ile Arg Arg
    930                 935                 940

Ile Glu Glu Tyr Ile Asn Asn Asn Lys Gly Leu Lys Lys Glu Val Glu
945                 950                 955                 960

Glu Lys Glu His Lys Arg His Ser Ser Phe Asn Ile Leu Lys Ser Lys
                965                 970                 975

Glu Lys Phe Phe Lys Asn Ser Ile Glu Asp Lys Ser His Glu Leu Lys
            980                 985                 990

Lys Lys His Glu Lys Asp Leu Leu  Ser Lys Asp Lys Glu  Ile Glu Glu
        995                 1000                1005

Lys Asn  Lys Lys Ile Lys Glu  Leu Asn Asn Asp Ile  Lys Lys Leu
    1010                1015                1020

Gln Asp  Glu Ile Leu Val Tyr  Lys Lys Gln Ser Asn  Ala Gln Gln
    1025                1030                1035

Val Asp  His Lys Lys Lys Ser  Trp Ile Leu Leu Lys  Asp Lys Ser
    1040                1045                1050

Lys Glu  Lys Ile Lys Asp Lys  Glu Asn Gln Ile Asn  Val Glu Lys
    1055                1060                1065

Asn Glu  Glu Lys Asp Leu Lys  Lys Lys Asp Asp Glu  Ile Arg Ile
    1070                1075                1080

Leu Asn  Glu Glu Leu Val Lys  Tyr Lys Thr Ile Leu  Tyr Asn Leu
    1085                1090                1095

Lys Lys  Asp Pro Leu Leu Gln  Asn Gln Asp Leu Leu  Ser Lys Ile
    1100                1105                1110

Asp Ile  Asn Ser Leu Thr Ile  Asn Glu Gly Met Cys  Val Asp Lys
    1115                1120                1125

Ile Glu  Glu His Ile Leu Asp  Tyr Asp Glu Glu Ile  Asn Lys Ser
```

-continued

```
    1130                1135                1140

Arg Ser  Asn Leu Phe Gln Leu  Lys Asn Glu Ile Cys  Ser Leu Thr
    1145                1150                1155

Thr Glu  Val Met Glu Leu Asn  Asn Lys Lys Asn Glu  Leu Ile Glu
    1160                1165                1170

Glu Asn  Asn Lys Leu Asn Leu  Val Asp Gln Gly Lys  Lys Lys Leu
    1175                1180                1185

Lys Lys  Asp Val Glu Lys Gln  Lys Lys Glu Ile Glu  Lys Leu Asn
    1190                1195                1200

Lys Gln  Leu Thr Lys Cys Asn  Lys Gln Ile Asp Glu  Leu Asn Glu
    1205                1210                1215

Glu Val  Glu Lys Leu Asn Asn  Glu Asn Ile Glu Leu  Ile Thr Tyr
    1220                1225                1230

Ser Asn  Asp Leu Asn Asn Lys  Phe Asp Met Lys Glu  Asn Asn Leu
    1235                1240                1245

Met Met  Lys Leu Asp Glu Asn  Glu Asp Asn Ile Lys  Lys Met Lys
    1250                1255                1260

Ser Lys  Ile Asp Asp Met Glu  Lys Glu Ile Lys Tyr  Arg Glu Asp
    1265                1270                1275

Glu Lys  Lys Arg Asn Leu Asn  Glu Ile Asn Asn Leu  Lys Lys Lys
    1280                1285                1290

Asn Glu  Asp Met Cys Ile Lys  Tyr Asn Glu Met Asn  Ile Lys Tyr
    1295                1300                1305

Gly Asp  Ile Cys Val Lys Tyr  Glu Glu Met Ser Leu  Thr Tyr Lys
    1310                1315                1320

Glu Thr  Ser Leu Lys Tyr Glu  Gln Ile Lys Val Lys  Tyr Asp Glu
    1325                1330                1335

Lys Cys  Ser Gln Tyr Asp Glu  Ile Arg Phe Gln Tyr  Asp Glu Lys
    1340                1345                1350

Cys Phe  Gln Tyr Asp Glu Ile  Asn Lys Lys Tyr Gly  Ala Leu Leu
    1355                1360                1365

Asn Ile  Asn Ile Thr Asn Lys  Met Val Asp Ser Lys  Val Asp Arg
    1370                1375                1380

Asn Asn  Asn Glu Ile Ile Ser  Val Asp Asn Lys Val  Glu Gly Ile
    1385                1390                1395

Ala Asn  Tyr Leu Lys Gln Ile  Phe Glu Leu Asn Glu  Glu Ile Ile
    1400                1405                1410

Arg Leu  Lys Gly Glu Ile Asn  Lys Ile Ser Leu Leu  Tyr Ser Asn
    1415                1420                1425

Glu Leu  Asn Glu Lys Asn Ser  Tyr Asp Ile Asn Met  Lys His Ile
    1430                1435                1440

Gln Glu  Gln Leu Leu Phe Leu  Glu Lys Thr Asn Lys  Glu Asn Glu
    1445                1450                1455

Glu Lys  Ile Ile Asn Leu Thr  Ser Gln Tyr Ser Asp  Ala Tyr Lys
    1460                1465                1470

Lys Lys  Ser Asp Glu Ser Lys  Leu Cys Gly Ala Gln  Phe Val Asp
    1475                1480                1485

Asp Val  Asn Ile Tyr Gly Asn  Ile Ser Asn Asn Asn  Ile Arg Thr
    1490                1495                1500

Asn Glu  Tyr Lys Tyr Glu Glu  Met Phe Asp Thr Asn  Ile Glu Glu
    1505                1510                1515

Lys Asn  Gly Met His Leu Ser  Lys Tyr Ile His Leu  Leu Glu Glu
    1520                1525                1530
```

```
Asn Lys  Phe Arg Cys Met Lys  Ile Ile Tyr Glu Asn  Glu Asn Ile
    1535                 1540                 1545

Lys Ser  Ser Asn Lys Ile Ile  Gly Leu Tyr Asn Tyr  Ser Arg Tyr
    1550                 1555                 1560

Tyr Gly  Leu Arg Glu Asp Leu  Cys Lys Glu Glu Ile  Val Pro Ser
    1565                 1570                 1575

Lys Ile  Gly Asn Ile Ser Asn  Lys Asn Glu Asn Asn  Asn Lys Lys
    1580                 1585                 1590

Asn Asn  Thr Cys Asp Gly Tyr  Asp Glu Lys Val Thr  Ile Val Leu
    1595                 1600                 1605

Cys Ile  Ile Leu Asn Glu Ile  Ile Lys Phe Leu Phe  Leu Asn Asp
    1610                 1615                 1620

Glu Tyr  Val Leu Leu Phe Glu  Lys Ile His Lys Asn  Val Trp Lys
    1625                 1630                 1635

Arg Met  Tyr Ile Pro Glu Glu  Ile Lys Phe Phe Ile  Leu Lys Tyr
    1640                 1645                 1650

Ile Thr  Leu Leu Asn Asn Leu  Arg Asp Tyr Ile Ile  Ser Val His
    1655                 1660                 1665

Asn Asn  Met Lys Asn Glu Lys  Tyr Asp Glu Cys Trp  Phe Leu Phe
    1670                 1675                 1680

Gln His  Tyr Phe Glu Arg Ser  Ser Asp Val Arg Lys  Glu Met Val
    1685                 1690                 1695

His Phe  Leu Leu Glu Arg Lys  Ser Gln Glu Asn Leu  Ile Ser Phe
    1700                 1705                 1710

Lys Ser  Lys Leu Lys Ser Lys  Lys Glu Lys Ile Leu  Thr Met Asp
    1715                 1720                 1725

Ile Leu  Asn Phe Ser Lys Glu  His Met Gln Leu Lys  Thr Ile Ala
    1730                 1735                 1740

His Leu  Arg Lys Glu Ile Asn  Tyr Glu Lys Leu Ser  Lys Asp Thr
    1745                 1750                 1755

Leu Asn  Arg Asp Tyr Asn Leu  Leu Leu Tyr Lys Tyr  Gln Glu Cys
    1760                 1765                 1770

Val Ser  Lys Leu Lys Arg Val  Lys Asn Leu Met Lys  Glu Ile Asn
    1775                 1780                 1785

Gln Asn  Val Phe Ile Glu Lys  Tyr Asp Asp Ile Ser  Lys Glu Leu
    1790                 1795                 1800

Asp Asn  Phe Ser Asp Gly Tyr  Asn Glu Gln Asn Glu  Gln His Val
    1805                 1810                 1815

Met Asp  Pro Ile Leu Leu Asn  Asn Asn Lys Asn Lys  Asn Asn Lys
    1820                 1825                 1830

Leu Ile  Thr Glu His Asn Asn  Pro Ile Ile Asn Arg  Leu Thr Asn
    1835                 1840                 1845

Phe Thr  Gln Asn Arg Asp Ser  Lys Tyr Lys Asn Lys  Ile Met Asp
    1850                 1855                 1860

Asp Val  Lys Gln Arg Lys Ile  Asn Ser Thr Met Asn  Asn Thr Asn
    1865                 1870                 1875

Lys Asn  Gly Ile Asn Ile Ile  Tyr Asn His Tyr Glu  Asn Leu Asn
    1880                 1885                 1890

Lys Pro  Asn Tyr Asn Asp Asn  Ile Asn Arg Leu Asn  Ser Tyr His
    1895                 1900                 1905

Gln Asn  Ile His Ile Ala Asn  Ser Ile His Pro Asn  Arg Asn Gln
    1910                 1915                 1920
```

```
Asn Lys  Ser Phe Leu Thr Asn  Gln Ala Asn Ser Thr  Tyr Ser Val
    1925                 1930                 1935

Met Lys  Asn Tyr Ile Asn Ser  Asp Lys Pro Asn Leu  Asn Gly Lys
    1940                 1945                 1950

Lys Ser  Val Arg Asn Ile Phe  Asn Glu Ile Val Asp  Glu Asn Val
    1955                 1960                 1965

Asn Lys  Thr Phe Val His Lys  Ser Val Phe Phe
    1970                 1975


<210> SEQ ID NO 3
<211> LENGTH: 1867
<212> TYPE: PRT
<213> ORGANISM: Plasmodium vivax

<400> SEQUENCE: 3

Met Val Phe Lys Phe Lys Lys Lys Lys Lys Glu Glu Ser Ser Asp Lys
1               5                   10                  15

Leu Ser Lys Gln Ser Gln Asn Asp Glu Gly Asn Ala Asn Glu Glu Ala
            20                  25                  30

Glu Lys Lys Asp His Lys Ser Asn Ser Trp Tyr Lys Lys Ile Ile Asp
        35                  40                  45

Asn Ala Ile Ile Thr Lys Ser Lys His Asp Asp Lys Glu Glu Gln Glu
    50                  55                  60

Glu Glu Lys Asn Gly Glu Gly Asn Asp Ser Arg Ala Met Glu Arg Asn
65                  70                  75                  80

Lys Asp Tyr Gln Leu Glu Glu Gln Leu Lys Glu Thr Leu Arg Ser Ile
                85                  90                  95

Thr Ser Leu Ser Thr Lys Ile Val Asn Tyr Glu Thr Lys Ile Glu Asp
            100                 105                 110

Leu Glu Lys Glu Leu Lys Met Glu Lys Asp Lys Gln Val Asp Lys Ala
        115                 120                 125

Tyr Glu Lys Glu Leu Lys Glu Lys Glu Asn Phe Ile Lys Gln Lys Ile
    130                 135                 140

Gly Met Leu Asn Glu Lys Glu Asn Leu Leu Asn Glu Lys Glu Leu Asp
145                 150                 155                 160

Ile Asn Met Arg Glu Glu Lys Ile Asn Asp Arg Glu Met Phe Ile Ser
                165                 170                 175

Lys Lys Glu Asp Lys Leu Asn Asp Met Gln Glu Gln Tyr Leu Glu Lys
            180                 185                 190

Asn Lys Glu Lys Glu Lys Leu His Phe Glu Ile Ala Asp Ile Lys Ile
        195                 200                 205

Ser Leu Glu Lys Leu Lys Tyr Glu Val Lys Asp Lys Lys Asp Cys Leu
    210                 215                 220

Glu Asn Val Ser Asn Lys Val Ile Leu Lys Glu Asn Thr Leu Arg Glu
225                 230                 235                 240

Leu Lys Glu Phe Ile Arg Glu Lys Asn Glu Met Ile Glu Ser Leu Asn
                245                 250                 255

Glu Lys Ile Thr Glu Lys Glu Lys Ile Tyr Glu Gln Leu Gly Lys Asp
            260                 265                 270

Val Glu Glu Lys Arg Lys Ile Ile Glu Leu Leu Asp Met Lys Ala Asn
        275                 280                 285

Glu Lys Glu Lys Tyr Phe Glu Glu Lys Ile Lys Glu Leu Glu Lys Glu
    290                 295                 300

Gln Asn Ala Leu Leu Gln Lys Leu Asn Asn Val Lys Met Arg Glu Lys
305                 310                 315                 320
```

```
Glu Val Glu Thr Arg Glu Asn Asp Phe Leu His Met Glu Asp Glu Leu
                325                 330                 335

Asn Asp Leu Arg Ser Ser Phe Ser Lys Asn Asp Cys Gln Leu Lys Ile
            340                 345                 350

Tyr Lys Leu Glu Ile Lys Asp Leu Ser Ser Ala Leu Val Glu Lys Glu
        355                 360                 365

Arg Glu Ile Leu Asp Leu Lys Asn Thr Tyr Asp Gly Glu Ile Cys Ser
    370                 375                 380

Leu Lys Asp Gln Ile Lys Glu Lys Glu Lys Glu Ile Ala Lys Gly Ser
385                 390                 395                 400

Ser Ser Gly Gly Asp Val Gly Ala Gln Asp Glu Pro Ala Ser Glu Val
                405                 410                 415

Glu Ser Glu Glu Lys Ala Asp Pro Lys Glu Glu Gly Val Glu Asn Ser
            420                 425                 430

Leu Thr Asp Leu Leu Lys Met Lys Glu Arg Glu Leu His Glu Met Lys
        435                 440                 445

Glu Lys Tyr Ala Lys Glu Ile Asp Thr Leu Asn Ser Glu Leu Asn Glu
    450                 455                 460

Lys Lys Lys Glu Phe Val Glu Ala Lys Asn Ser His Ile Asn Gln Ile
465                 470                 475                 480

Asn Asn Leu Asn Asp Glu Ile Glu Glu Ser Glu Ser Lys Met Ala Glu
                485                 490                 495

Leu Lys Ser Gly Tyr Glu Met Glu Ile Lys Lys Leu Arg Ser Glu Ile
            500                 505                 510

Asn Ala Val His Glu Glu Lys Tyr Leu Leu Ser Asn Glu Lys Gln Thr
        515                 520                 525

Leu Ser Gly Glu Ile Asp Lys Leu Asn Glu Glu Lys Lys Ser Leu Ala
    530                 535                 540

Ser Glu Lys Glu Glu Leu His Asn Lys Ile Thr Thr Leu Asn Ser Glu
545                 550                 555                 560

Ile Gly Thr Leu His Val Glu Lys Gln Ala Leu Thr Gly Glu Ile Asn
                565                 570                 575

Thr Leu Asn Asp Leu Ile His Thr Leu Lys Asn Glu Ile Ser Ser Ser
            580                 585                 590

Asp Asn Leu Ile Ser Lys Leu Lys Glu Gln Met Asn Ala Ile Asn Glu
        595                 600                 605

Glu Lys Glu Gly Lys Glu Lys Leu Ile Thr Glu Ile Glu Asn Asn Tyr
    610                 615                 620

Lys Asn Glu Ile Asn Ala Leu Lys Glu Lys Leu Lys Asp Thr Asp Asn
625                 630                 635                 640

Gln Val Ser Ile Ser Ile Arg Glu Glu Met Asp His Leu Lys Cys Val
                645                 650                 655

Leu Gly Glu Thr Glu Lys Glu Asn Lys Gln Met Lys Glu Asp Tyr His
            660                 665                 670

Lys Lys Ile Lys Gln Tyr Asp Glu Glu Leu Leu Ser Lys Gln Gln Tyr
        675                 680                 685

Phe Glu Glu Glu Leu Asn Asn Ile Arg Ile Lys Ser His Glu Lys Glu
    690                 695                 700

Gln Ile Leu Ile Leu Lys Asn Asp Glu Leu Lys Glu Ser Lys Leu Lys
705                 710                 715                 720

Thr Glu Glu Lys Tyr Leu Lys Leu Tyr Asp Asp Lys Met Ser Leu Leu
                725                 730                 735
```

-continued

```
Arg Asn Met Cys Ser Lys Val Gly Leu Pro Tyr Ser Asp Glu Val Ser
            740                 745                 750

Val Glu Glu Leu Leu Glu Arg Val Gly Asn Tyr Val Ser Gly Met Gly
        755                 760                 765

Glu Pro Gly Gly Ala Ala His Arg Gly Glu Gln Ser Glu Glu Pro His
    770                 775                 780

Glu Gly Gln Ser Ile Val Glu Glu Thr Asn Glu Pro Leu Leu Ser Ala
785                 790                 795                 800

Gln Thr Ala Asp Asn Ala Asn Ser Leu Glu Asp Lys Thr Thr Leu Gln
                805                 810                 815

Ala Leu Gln Lys Glu Leu Glu Ser Val Gln Glu Glu Tyr Arg Glu Glu
            820                 825                 830

Val Ala Lys Met Lys Ser Tyr Leu Ala Met Lys Glu Lys Thr Ile Glu
        835                 840                 845

Glu Ser Asn His Thr Ile Ala Glu Leu Thr Gly Lys Ile Asn Ser Leu
    850                 855                 860

Asn Asp Thr Ile Ser Phe Phe Lys Val Asn His Ser Glu Glu Lys Ile
865                 870                 875                 880

Asn Ser Tyr Met Asp Glu Ile Asn Ser Leu Ser Leu Thr Leu Ser Glu
                885                 890                 895

Leu Lys Ala Asn Asn Glu Gln Glu Gln Leu Glu Asn Arg Asn Glu Ile
            900                 905                 910

Ala Arg Leu Ser Glu Glu Leu Ser Gly Tyr Lys Arg Arg Ala Asp Glu
        915                 920                 925

Gln Cys Arg Lys Arg Ser Ser Glu Lys Glu Arg Ser Glu Ser Lys Arg
    930                 935                 940

Gly Asp Thr Arg Gly Asp Ser Glu Lys Glu Gln Ile Ser Glu Ser Asp
945                 950                 955                 960

Val Glu Gly Gly Gly Asn Leu Lys Ser Phe Leu His Phe Pro Leu Arg
                965                 970                 975

Lys Ile Lys Gly Lys Lys Arg Lys Ala Ser Lys Thr Glu Lys Glu Ile
            980                 985                 990

Gln Thr Glu Leu Arg Arg Asn Glu  Pro Glu Asn Glu Gln  Ser Glu Lys
        995                 1000                1005

Asn Glu  Lys Ala Pro Arg Gly  Asp Ser Leu Glu Val  Asp Gln Tyr
    1010                1015                1020

Lys Lys  Glu Leu Glu Glu Lys  Ala Lys Ile Ile Glu  Asp Leu Lys
    1025                1030                1035

Asp Lys  Ile Cys Thr Leu Thr  Asn Glu Val Met Asp  Leu Lys Asn
    1040                1045                1050

Leu Lys  Asn Glu Leu Ala Glu  Arg Asp Ser Ser Leu  Ala Lys Ala
    1055                1060                1065

Gly Glu  Glu Ala Glu Arg Gln  Arg Glu Gln Leu Asp  Thr Leu Ser
    1070                1075                1080

Ala Gln  Leu Gly Gly Ala Asn  Gly Glu Val Glu Arg  Leu Ser Glu
    1085                1090                1095

Glu Val  Glu Arg Leu Asn Glu  Glu Val Glu Lys Leu  Lys Glu Gly
    1100                1105                1110

Glu Ala  Gln Ser Trp Gly Glu  Ala Glu Lys Trp Lys  Gly Glu Ala
    1115                1120                1125

Glu Lys  Trp Lys Glu Asp Ala  Ala Lys Trp Glu Ala  Asp Thr Val
    1130                1135                1140

Lys Leu  Lys Glu Asp Ala Ala  Lys Trp Glu Ser Asp  Ala Val Lys
```

```
    1145                1150                1155

Trp Glu  Ser Asp Ala Glu Thr  Trp Arg Lys Glu Ala  Glu Glu Leu
    1160                1165                1170

Arg Ser  Ser Ala Asn Gln Leu  Asn Glu Glu Leu Cys  Ser Lys Glu
    1175                1180                1185

Asn Asn  Tyr Val Leu Lys Leu  Asn Glu Asn Val Gly  Val Ile Gln
    1190                1195                1200

Lys Met  Lys Asp Ser Ile Asp  Ala Arg Glu Lys Glu  Lys Glu Asn
    1205                1210                1215

Tyr Val  Arg Glu Ile Asn Asp  Leu Arg Asn Glu Leu  Glu Gly Leu
    1220                1225                1230

Lys Leu  Lys His Asp Ala Leu  Ser Glu Thr Tyr Lys  Gln Leu Glu
    1235                1240                1245

Gly Lys  Ser Ser Pro Pro Ser  Gly Asp Asp Pro Pro  Gly Gly Asp
    1250                1255                1260

Asn Tyr  Thr Ser Glu Gly Glu  Asn Lys Leu Ser Ile  Pro Asn Glu
    1265                1270                1275

Asn Cys  Glu Met Asp Gln Ala  Glu Glu Ala Asn Ala  Asn Pro Gly
    1280                1285                1290

Val Pro  Lys Ser Glu Ile Ala  Thr Glu Gly Gly Val  Ser Ser Leu
    1295                1300                1305

Ala Val  Asn Asp Tyr Ile Ser  Glu Ile Ala His Leu  Lys Glu Glu
    1310                1315                1320

Ile Asn  Arg Leu Thr Leu Leu  Tyr Ser Asn Glu Leu  Asn Glu Lys
    1325                1330                1335

Asn Ser  Ser Asp Ile Arg Thr  Lys Glu Leu Leu Ser  Gln Leu Lys
    1340                1345                1350

Glu Leu  Glu Val Arg Asp Lys  Glu Asn Glu Glu Lys  Ile Ala Ala
    1355                1360                1365

Leu Ser  Lys Met Asn Glu Lys  Met Lys Ala Lys Asn  Glu Lys Leu
    1370                1375                1380

Lys Ser  Gly Lys Trp Leu Ser  Arg Lys Asp His Ala  Pro Asn Glu
    1385                1390                1395

Glu Val  Asp Ile Ala Gly Glu  Glu Arg Lys Lys Lys  Glu Lys Glu
    1400                1405                1410

Lys Val  Pro His Pro Asp Val  Lys Glu Glu Ser Leu  Ser Ser Glu
    1415                1420                1425

His Val  Asn Thr Leu Glu Gly  Asn Thr Tyr Arg Val  Met Arg Ile
    1430                1435                1440

Val Asp  Glu Ser Ser Pro Ala  Gly Gly Gly Gln Ile  Ile Gly Ser
    1445                1450                1455

Tyr Leu  Tyr Thr Lys Lys Val  Glu Asp Leu His Ala  Val Asn Gly
    1460                1465                1470

Ala Asn  Val Ala Asp Ala Gln  Leu Ala Glu Lys Asn  Ala Ile Thr
    1475                1480                1485

Val Val  Cys Leu Ile Leu Ser  Glu Ile Leu Ser Leu  Leu Phe Leu
    1490                1495                1500

Asn Asp  Gln Phe Val Asn Ala  Phe Glu Arg Ile Asn  Lys Ser Leu
    1505                1510                1515

Trp Lys  Leu Met Tyr Met Pro  Glu Glu Ile Lys Ala  Leu Leu Leu
    1520                1525                1530

Arg Tyr  Phe Ser Phe Met Ser  Lys Leu Arg Asp Tyr  Ala Lys Glu
    1535                1540                1545
```

```
Val His Gly Arg Val Glu Asn Glu Arg Tyr Glu Asp Ser Gln Arg
    1550                1555                1560

Gln Asp Asn Gln Arg Tyr Asp Asp Ser Trp Leu Leu Phe Gln Asn
    1565                1570                1575

Tyr Leu Glu Thr Ser Ser Ser Ile Lys Arg Asp Leu Val Cys Phe
    1580                1585                1590

Ile Leu Glu Glu Lys Glu Asn Glu Leu Ala Glu Leu Gly Glu His
    1595                1600                1605

Tyr Gly Gly Gly Met Arg Lys Gly Glu Glu Val Ile Gly Gly Val
    1610                1615                1620

Arg Gly Val Arg Gly Gly Lys Ile Ala Asp Ile Ile Asn Leu Ser
    1625                1630                1635

Lys Asp Glu Met Arg Leu Lys Thr Ile Ala Gln Leu Arg Arg Asp
    1640                1645                1650

Leu Asp Phe Glu Lys Lys Ser Lys Thr Leu Leu Ser Arg Asp Tyr
    1655                1660                1665

Gln Leu Leu Leu Tyr Lys Tyr Gln Glu Cys Val Arg Lys Leu Lys
    1670                1675                1680

Arg Val Lys Asn Met Ile Arg Gln Leu Asn Leu Asn Asp His Ser
    1685                1690                1695

Asn Arg Gly Ser Phe Ala Leu Asn Arg Glu Leu Asp Arg Cys Ser
    1700                1705                1710

Glu Val Ser Asn Glu Arg Gly Phe Asn Glu Glu Gly Gly Asp Glu
    1715                1720                1725

Asp Ser His Gly Asn Tyr Lys Asn Cys Ile Leu Gln Asp Asn Asn
    1730                1735                1740

Asn Asn Ser Ser Val Asn Asn Tyr Asn Ser Ser Asn Thr Lys Leu
    1745                1750                1755

Glu Ser Arg Glu Asn Val Leu Ile Lys Asp Leu Ile Asn Leu Arg
    1760                1765                1770

Arg Ala Gln Lys Val Lys Gly Asn Asn Leu Ile His Trp Gly Arg
    1775                1780                1785

Pro Ser Met Met Met Gly Gly Arg Cys His Gln Asp Ala Ser His
    1790                1795                1800

Val Val Arg Ala Met Val Asn Gly Pro Lys Ile Ser Ser Gln Asn
    1805                1810                1815

Ile Phe Ala His Met Asn Arg Leu Ser Asn Ala Pro Lys Ile Ser
    1820                1825                1830

Asp His Leu Asp Asp Met Lys Lys Met Lys Asn Ile Phe Asn Glu
    1835                1840                1845

Phe Val Glu Thr Arg Gly Asp Val Thr Phe Val His Arg Ser Pro
    1850                1855                1860

Phe Cys Glu Thr
    1865
```

<210> SEQ ID NO 4
<211> LENGTH: 5940
<212> TYPE: DNA
<213> ORGANISM: Plasmodium falciparum

<400> SEQUENCE: 4

```
atggtattca cgttcaaaaa taagaaaaag aaaaaagaag ctagttcaga taaagtaagc      60

aaagaatcat ttaatgagga agataatgaa aataatgaaa agagggaaaa aagcgattca     120
```

-continued

```
tggtataaaa aaataataga aactaaagga aaaagtaaaa ctaaatataa aaatgataat    180

tccttagatg ataatattaa tgaggacata ataaataata ataataataa taataatgat    240

aataataatg ataacaataa tgataataat aatgataata ataatgataa taataatgat    300

aataataatg agaataataa tgataataat aattttaata attatagcga tgaaatatca    360

aaaaatatta tacataaaga caatgagcta gaaaaccagc ttaaggatac attaaagtcc    420

attagttcgt tgtcgaataa aattgtgaat tacgaaagta aaattgaaga attagaaaaa    480

gaattaaaag aagtaaagga taagaatatt gataataatg attatgaaaa taaattaaaa    540

gaaaaagaag attttgttaa acaaaaaatt gatatgctaa atgaaaaaga aaatctttta    600

caagaaaaag aattagatat taataaaaga gaaaagaaaa ttaatgaaaa agaaaagaat    660

ataataaaaa aggaagaaac atttcataat atagaaaaag agtatttaga aaaaaataaa    720

gaaagagaaa cgatttctat agaaattata gatattaaaa aacatctaga aaaactaaaa    780

atagaaataa aagaaaaaaa agaagattta gaaaatttaa ataaaaaatt gttatcaaaa    840

gaaaatgtac taaaagaatt aaaaggatgt gttaaggaaa aaaatgaaac cattaattca    900

ttgaatgata atattattga aaaagaaaaa aaatataaat tattagaata tgagttggaa    960

gaaaaaaata aacaaattga tttattaaac aaacaagaaa aagaaaagga aaaggagaag   1020

gaaagggaaa aggagaagga aagggaaaag gaaaaagaaa aggaatatga tacattaatc   1080

aaagaattaa aagatgaaaa gatttccatt ttagaaaaag ttcattccat taaagtaaga   1140

gaaatggata ttgaaaaaag agaacataat ttccttcata tggaagatca attaaaagat   1200

ttaaaaaata gttttgtaaa gaataataat caattaaaag tatataaatg tgaaataaag   1260

aatcttaaaa ccgaattaga aaaaaaagaa aaagaattaa aagatataga aaatgtatct   1320

aaagaagaaa taaataaatt aataaaccaa ttaaatgaaa aggagaaaca aattcttgcg   1380

tttaataaaa atcataaaga agaaattcat ggattgaaag aagaattaaa agaatctgtg   1440

aaaataacca aaatagaaac acaagagtta caagaaatgg tagacatcaa acaaaaagag   1500

ttagaccaat tgcaggaaaa atataacgca caaatagaaa gtataagcat cgaattaagt   1560

aaaaaagaga aggaatataa tcaatataaa aatacttata tagaagaaat aaataattta   1620

aatgaaaaat tagaagaaac taataaagaa tatacgaatt tacaaaataa ttatacaaat   1680

gaaataaata tgttaaataa tgatatacat atgttaaatg gcaatataaa aaccatgaat   1740

acacaaataa gtactttaaa aaatgatgta catttgttaa atgaacaaat agataaatta   1800

aataatgaaa agggtacatt aaatagtaaa attagtgaat tgaatgttca aattatggat   1860

ttaaaagagg aaaaagattt cttaaataat caaattgtag atttaagtaa tcaaattgat   1920

ttgttaacaa gaaaaatgga agagaaggaa aataaaatgt tggaacagga gaataagtat   1980

aaacaagaga tggaactctt aagggggaat ataaaaagtt ctgagaatat tttaaacaat   2040

gacgaagagg tgtgtgattt aaaaaggaaa ttaagtttga aggaaagtga aatgaaaatg   2100

atgaaggagg aacatgataa gaagttggct gagttgaaag atgattgtga tgtgaggata   2160

cgggagatga atgaaaagaa tgaagataaa attaatatgt taaaggaaga atatgaagat   2220

aaaattaata cgttgaagga acaaaatgaa gataaaatta atacgttaaa ggaacaaaat   2280

gaagataaaa ttaatacatt gaaagaagag tatgaacata aaattaatac gatgaaggaa   2340

gaatatgaac ataaaattaa tacgttgaat gaacaaaatg aacataaaat taatacgttg   2400

aatgaacaaa atgaacataa aattaatacg atgaaggaag aatatgaaga taaaatgaac   2460

acgttgaatg aacaaaatga agataaaatg aattcgttga aggaagagta tgaaaataag   2520
```

```
ataaatcaaa ttaatagtaa taatgaaata aaaataaaag atgtagtgaa tgaatatatt   2580
gaagaagtgg acaaattaaa agttactttg gatgaaaaaa aaaaacaatt tgataaagaa   2640
ataaattacg cacatatcaa agctcatgaa aaggagcaaa tattattaac agaaatggaa   2700
gaattaaaat gtcagaggga taataaatat tcagatttat atgagaaata tattaaacta   2760
ataaaaagta tttgtatgat aattaacatt gaatgttgtg atgatataga aaatgaagat   2820
attataagaa gaattgaaga atatataaat aataacaaag gcttgaaaaa agaagtagaa   2880
gaaaaagaac ataaaagaca ttcctccttt aatattttaa aaagtaaaga aaagtttttt   2940
aaaaatagca tagaagataa aagtcatgaa ttaaaaaaaa aacatgaaaa agatttatta   3000
tcaaaagata aagaaattga agaaaagaat aaaaaaataa aagaactgaa taatgatata   3060
aaaaagttac aagatgaaat attagtatat aaaaaacaaa gtaatgcaca acaagtagat   3120
cataaaaaga aaagttggat tcttcttaaa gataaatcta aagagaaaat aaaagataaa   3180
gaaaatcaaa taaatgtaga aaaaaatgaa gaaaaggatt taaaaaaaaa agatgatgaa   3240
ataagaattt taaatgaaga acttgtaaaa tataaaacaa ttttatataa tttaaaaaaa   3300
gatccattat tacaaaatca agatttatta tcaaaaattg acataaattc tttaacaata   3360
aatgaaggaa tgtgtgtaga taaaatagaa gagcacattt tggattatga tgaagaaata   3420
aataaaagca gatctaattt gtttcaacta aaaaatgaaa tatgttcttt aacaactgag   3480
gttatggaac ttaataataa gaaaaatgaa ttaattgaag aaaataataa attaaattta   3540
gtagatcaag gaaagaagaa attaaaaaag gatgtggaaa aacaaaaaaa agaaatagag   3600
aaattaaata aacaattaac aaaatgtaat aaacaaatag atgaattaaa tgaagaagtg   3660
gaaaaattaa ataatgaaaa tattgaatta attacatatt caaatgattt aaataacaaa   3720
tttgatatga aagaaaataa tcttatgatg aaattagatg aaaatgaaga taatataaag   3780
aaaatgaaaa gtaaaattga tgatatggaa aaagaaataa aatatagaga agatgaaaaa   3840
aaaagaaatt taaatgaaat taataattta aagaaaaaga atgaagatat gtgtattaaa   3900
tataatgaaa tgaatattaa gtatggagat atttgtgtaa aatatgaaga aatgtctctt   3960
acgtataaag aaacatctct taaatatgag caaattaaag tgaaatatga tgaaaagtgt   4020
tctcaatatg acgaaatacg ttttcaatat gatgagaaat gttttcaata tgatgagata   4080
aataagaaat atggtgcttt attaaatata aatattacta ataaaatggt tgattcaaaa   4140
gtggatagaa ataataatga aataatttca gtagataata aagtagaagg aattgcgaat   4200
tatttaaaac aaatatttga attaaatgaa gagatcatac gattaaaagg agaaataaat   4260
aaaattagct tattatatag taatgaatta aatgagaaaa atagttatga tataaacatg   4320
aaacatatac aagaacaatt actttttttg gaaaagacaa ataaagaaaa tgaagaaaaa   4380
ataattaatt tgactagcca atattctgat gcatacaaga agaagagtga tgaatctaaa   4440
ttatgtggtg cacagtttgt tgatgatgtt aatatatatg gaaatatatc aaataataat   4500
ataagaacaa atgaatataa atatgaagag atgtttgata cgaatataga agagaagaat   4560
ggtatgcatt tatctaagta tattcatcta ttagaagaaa ataaatttcg atgtatgaaa   4620
ataatttatg aaaatgaaaa tataaaaagt agtaataaaa taattggatt gtataattat   4680
tcaaggtatt atgggttaag agaagatttg tgtaaagaag aaatcgttcc ttcaaaaata   4740
ggaaatatat ctaataaaaa tgaaaataat aataagaaga acaacacttg tgatggttat   4800
gatgagaagg ttacaatagt tttatgcatt atattaaatg aaataataaa atttttattt   4860
```

```
ttaaatgacg aatatgtatt attatttgaa aagattcata aaaatgtttg gaaacgaatg   4920

tatatcccag aagaaataaa attttttatc ctaaaatata ttacgctgtt aaataacttg   4980

agagattata taataagtgt acataataat atgaaaaatg agaaatatga tgaatgttgg   5040

tttttatttc aacattattt tgaaagatcg agtgatgtaa gaaaagagat ggttcatttc   5100

ttattagaaa gaaagagtca agaaaattta atatctttta aaagtaaatt aaaaagtaaa   5160

aaagaaaaaa tattaacaat ggacatattg aattttagta aagaacatat gcaattaaaa   5220

accatagctc atctaagaaa agaaataaat tatgaaaaac tttctaagga taccttaaat   5280

agagattata atttattatt atataaatat caagaatgtg taagtaaatt aaaaagggta   5340

aaaaatttaa tgaaagaaat aaatcaaaat gtatttatag aaaaatatga tgatataagt   5400

aaagaattag ataatttttc agatggatat aatgaacaaa atgaacaaca tgtaatggat   5460

cctattttat taaataataa taaaaacaaa aataacaaat tgataactga acataataat   5520

cctataatta ataggctaac taattttaca caaaacagag attcaaaata taaaaataaa   5580

ataatggatg atgtaaaaca aagaaaaata aatagtacaa tgaataatac aaataaaaat   5640

ggtattaata ttatatataa tcattatgaa aatttaaata aaccaaacta taatgataat   5700

ataaatagat taaattcata tcatcaaaat atacatattg ctaattcaat tcatcctaat   5760

agaaatcaaa ataaaagttt tcttacgaat caagcaaata gtacatatag tgttatgaaa   5820

aattatataa attcagataa accaaattta aatggaaaaa agagtgtaag aaatattttt   5880

aatgaaattg tcgatgaaaa tgtaaataaa acgtttgttc ataaaagtgt atttttttaa   5940
```

<210> SEQ ID NO 5
<211> LENGTH: 5604
<212> TYPE: DNA
<213> ORGANISM: Plasmodium vivax

<400> SEQUENCE: 5

```
atggtattca aatttaagaa gaaaaagaag gaagaaagct cggacaagtt aagcaagcaa     60

tcgcaaaacg atgaaggaaa tgccaatgag gaggcagaaa aaaaagacca caagagtaac    120

tcctggtaca agaaaataat cgacaatgca attataacga agagcaagca tgacgataag    180

gaggagcagg aggaggagaa aaatggcgaa ggaaatgaca gcagggcgat ggaaagaaat    240

aaagattatc aattggaaga gcaactgaag gaaaccctaa ggtcaatcac gtccttgtca    300

accaaaattg tgaattacga aacgaagatt gaagatttgg agaaagagtt aaaaatggaa    360

aaagataaac aagtggataa ggcatacgaa aaggagttga aggagaagga gaattttatt    420

aaacaaaaaa ttggcatgct aaatgagaag gaaaatctgc taaatgagaa ggagctggac    480

ataaatatga gagaagaaaa aattaatgac agagaaatgt tcatttcgaa aaaggaagac    540

aaactgaatg acatgcagga gcagtacttg gaaaaaaata aagaaaaaga aaaactccat    600

tttgaaattg cagatattaa gatttcctta gaaaagctaa agtacgaagt taaagataaa    660

aaggactgcc tagaaaatgt cagcaataag gtaattttga aggaaaatac tctgagggag    720

ttaaaagaat ttataaggga aaaaaacgaa atgatagaat cgcttaacga gaagataaca    780

gagaaggaga aaatatatga gcagttaggg aaggacgtgg aggagaagag aaagatcatc    840

gaattgctag acatgaaggc aaatgaaaag gaaaaatatt tcgaagaaaa aattaaagag    900

ttagaaaaag aacaaaatgc gcttctgcaa aagttaaata atgttaagat gagggagaag    960

gaagttgaga cgagggaaaa tgacttcctg cacatggagg acgagctgaa tgatcttcgc   1020

agtagcttct cgaagaatga ttgtcagcta aagatctaca aattggaaat aaaagatttg   1080
```

```
agcagcgccc ttgtggagaa ggagagagaa atattggact tgaaaaatac ctacgacggg   1140
gaaatctgct cattaaagga tcagataaag gaaaaggaaa aggaaatcgc caaaggtagt   1200
tcctccggtg gtgacgtggg tgcacaagat gagccagcta gcgaagttga aagtgaagaa   1260
aaggcggacc ccaaagagga aggtgtggag aacagcttga ccgatttgct caaaatgaag   1320
gaaagagagc tgcacgaaat gaaggaaaaa tacgcaaagg aaatagacac actgaatagc   1380
gagctgaatg agaaaaagaa agaattcgtg gaggcaaaaa atagccacat caaccagata   1440
aacaacctaa atgatgaaat tgaggagagc gaaagcaaaa tggcagaact gaaaagtggc   1500
tacgaaatgg agatcaaaaa actgcgcagc gaaattaatg cagtgcacga ggagaagtac   1560
ctcttgagca acgaaaaaca aacactcagt ggagagatag acaagctgaa tgaagagaag   1620
aagtccctgg ccagcgagaa ggaggagcta cataacaaaa taaccacgtt gaacagcgaa   1680
attgggacgt tacatgtgga gaaacaggca ctcactggag aaataaacac cttaaacgat   1740
ctgattcaca ccctgaagaa tgaaatcagc tcgtcggata acctgattag caaattgaaa   1800
gagcaaatga acgccatcaa cgaagaaaag gaaggaaagg aaaaactcat cacagagata   1860
gaaaataatt ataaaaatga aataaacgcg ctgaaggaaa aattaaaaga cacggacaat   1920
caagtgagca taagtattag ggaagagatg gaccacctca aatgcgtcct tggcgaaacg   1980
gaaaaggaaa acaaacagat gaaggaggac taccacaaaa agataaaaca gtatgatgaa   2040
gaattgctat cgaagcagca atattttgaa gaagaattaa ataacatacg catcaaatcg   2100
cacgaaaagg aacaaatttt gattttaaaa aatgacgagt tgaaggagtc gaagctaaag   2160
acggaggaga agtacctcaa gctgtacgat gacaaaatga gtctcctcag gaatatgtgc   2220
tccaaagtgg ggctccccta cagcgatgaa gtttcggtgg aggagcttct cgagcgggtg   2280
ggcaactacg taagtgggat gggtgaaccg gggggtgcgg cacacagggg ggagcaaagt   2340
gaggagccgc atgaggggca gtcgattgtg gaggagacga atgaacccct tttgagcgcc   2400
caaacggccg acaatgctaa tagcctagag gacaagacaa ccctacaggc gctacagaaa   2460
gaactggaaa gtgtgcaaga agagtacaga gaagaggtag ccaaaatgaa gagctatttg   2520
gcgatgaagg aaaaaacgat agaggagtcg aaccacacaa tcgccgagtt gaccggaaag   2580
ataaacagcc tgaatgatac catttcgttt tttaaggtta accactctga ggagaaaatt   2640
aattcctata tggacgaaat taacagcttg agcttgacgc ttagcgagct gaaggctaat   2700
aatgaacagg agcagttgga gaatcgaaac gaaattgcca ggctgtcgga agagctcagc   2760
gggtataagc ggcgtgctga tgagcaatgt agaaagagga gcagcgagaa ggagagaagc   2820
gagtccaaga ggggagacac aagaggtgac tccgagaagg aacaaatctc cgagtcggac   2880
gtggaagggg ggggcaattt aaaatccttt ttacactttc cccttcgaaa aataaaaggg   2940
aaaaaaagaa aggcctctaa aactgagaag gaaatacaaa cggagcttag gagaaacgag   3000
ccagagaatg aacagagtga gaaaaatgag aaggcgccta gaggagacag cctggaggtg   3060
gaccagtaca aaaaggaatt ggaggaaaag gcgaagatta ttgaggactt gaaggacaaa   3120
atatgcaccc tgacgaatga ggttatggat ttgaagaatt tgaagaacga gctggctgag   3180
cgggatagca gcttggcgaa ggcgggcgag gaggcggaaa ggcaaagaga gcagttggac   3240
acgctgagcg cccaactggg gggtgcaaac ggagaggtgg agagactcag cgaagaggtg   3300
gagaggctca acgaagaggt ggagaagctg aaggagggag aggcacaatc gtggggggaa   3360
gcggagaagt ggaaagggga agcagagaag tggaaagaag acgcagcgaa gtgggaagcg   3420
```

```
gacacagtga aattgaaaga ggacgcagcg aaatgggaat cggacgcagt gaagtgggaa   3480
tcggacgccg agacgtggag gaaagaagcg gaggaactga gaagcagcgc gaatcaattg   3540
aacgaagaat tatgctcgaa ggaaaataac tacgtgttga agctgaacga aaatgtggga   3600
gttatacaaa aaatgaagga ctcaattgat gcacgtgaaa aggagaagga gaattacgtt   3660
cgcgagataa acgatttgag aaacgaactc gaagggttga aattgaagca tgatgcgttg   3720
agtgagacgt ataagcagtt ggaggggaag agcagccccc ccagtggaga tgaccccccct  3780
ggtggagata actacaccag tgagggagag aataaattaa gcatcccaaa tgagaattgc   3840
gaaatggacc aagcggagga agcgaatgcc aacccaggtg ttcccaagag cgaaattgcc   3900
accgaggggg gtgtctcctc attggcagtg aacgattaca taagcgaaat agcgcacctg   3960
aaggaagaaa taaacagact aaccctactg tatagcaacg aactgaacga aaaaaacagc   4020
tctgatatta ggaccaaaga gctgctgagc cagttgaagg aactcgaagt gagggataaa   4080
gaaaatgagg aaaagattgc tgcgctgagc aaaatgaatg agaaaatgaa agcgaaaaat   4140
gaaaagctga aatcggggaa gtggttatct aggaaggacc acgcgccgaa tgaagaggta   4200
gatatcgcag gggaggagcg taagaagaag gagaaggaga aagtgcctca cccggatgtg   4260
aaagaggaga gtctgtcttc agagcatgtg aacacactgg aaggaaacac ctaccgcgtg   4320
atgagaatag ttgatgaaag tagccccgcg ggaggaggcc aaataatagg gtcctacttg   4380
tacaccaaaa aggtggaaga tttacacgca gtaaatggag caaatgtggc agatgcacag   4440
ctggctgaga aaaacgcaat cacagttgtg tgtctaattc taagcgaaat cttaagcctc   4500
ctatttttga acgatcaatt tgttaacgcc tttgaacgga taaacaaaag tctgtggaag   4560
cttatgtaca tgcctgaaga gattaaagcg ctgcttctga ggtatttttc ctttatgagt   4620
aagctcaggg attatgccaa ggaggtgcac gggagggtgg aaaatgagag gtatgaagac   4680
agccaaaggc aggacaacca acggtacgac gattcgtggt tactttttca aaactatttg   4740
gagacgtcga gtagtatcaa gagggacctg gtgtgcttca ttttggaaga gaaggaaaat   4800
gaactagccg agctgggcga gcactatggt ggtggaatga gaaagggaga ggaagtaatc   4860
gggggagtac gcggagtgcg cgggggaaaa atcgccgaca tcataaacct ttcaaaggac   4920
gaaatgagat tgaagaccat agcacagtta agaagagacc tagattttga aaagaaatcg   4980
aaaacattgc taagcaggga ttatcagttg ttactttata agtaccagga atgcgtgagg   5040
aagctaaaga gggtaaaaaa tatgataagg cagctaaatc tgaacgacca ttcaaataga   5100
ggcagtttcg ccttaaacag ggagctggac aggtgttccg aagtgagcaa cgagcgaggt   5160
tttaacgagg agggggtga tgaagattcg cacggaaatt acaaaaactg cattctgcaa    5220
gacaataata ataatagcag tgtaaataac tataatagta gtaacaccaa attggagagt   5280
cgggaaaatg ttctaatcaa ggacctaatc aatttgagga gggcgcaaaa ggtgaaggga   5340
aataatttga tccactgggg ccgtcccagc atgatgatgg ggggcaggtg tcaccaagac   5400
gcttcccatg tggtaagggc gatggtaaat ggacccaaaa taagcagcca gaatatcttc   5460
gcacacatga acaggctgag caatgcgccc aaaattagcg accacttgga tgacatgaaa   5520
aaaatgaaaa atatttttaa cgaatttgtt gaaaccagag gggacgttac gtttgtgcac   5580
aggagtccct tctgcgaaac gtga                                          5604
```

<210> SEQ ID NO 6
<211> LENGTH: 600
<212> TYPE: PRT
<213> ORGANISM: Plasmodium falciparum

<400> SEQUENCE: 6

```
Met Val Phe Thr Phe Lys Asn Lys Lys Lys Lys Lys Glu Ala Ser Ser
1               5                   10                  15

Asp Lys Val Ser Lys Glu Ser Phe Asn Glu Glu Asp Asn Glu Asn Asn
            20                  25                  30

Glu Lys Arg Glu Lys Ser Asp Ser Trp Tyr Lys Lys Ile Ile Glu Thr
        35                  40                  45

Lys Gly Lys Ser Lys Thr Lys Tyr Lys Asn Asp Asn Ser Leu Asp Asp
    50                  55                  60

Asn Ile Asn Glu Asp Ile Ile Asn Asn Asn Asn Asn Asn Asn Asn Asp
65                  70                  75                  80

Asn Asn Asn Asp Asn Asn Asn Asp Asn Asn Asn Asp Asn Asn Asn Asp
                85                  90                  95

Asn Asn Asn Asp Asn Asn Asn Glu Asn Asn Asn Asp Asn Asn Asn Phe
            100                 105                 110

Asn Asn Tyr Ser Asp Glu Ile Ser Lys Asn Ile Ile His Lys Asp Asn
        115                 120                 125

Glu Leu Glu Asn Gln Leu Lys Asp Thr Leu Lys Ser Ile Ser Ser Leu
    130                 135                 140

Ser Asn Lys Ile Val Asn Tyr Glu Ser Lys Ile Glu Glu Leu Glu Lys
145                 150                 155                 160

Glu Leu Lys Glu Val Lys Asp Lys Asn Ile Asp Asn Asn Asp Tyr Glu
                165                 170                 175

Asn Lys Leu Lys Glu Lys Glu Asp Phe Val Lys Gln Lys Ile Asp Met
            180                 185                 190

Leu Asn Glu Lys Glu Asn Leu Leu Gln Glu Lys Glu Leu Asp Ile Asn
        195                 200                 205

Lys Arg Glu Lys Lys Ile Asn Glu Lys Glu Lys Asn Ile Ile Lys Lys
    210                 215                 220

Glu Glu Thr Phe His Asn Ile Glu Lys Glu Tyr Leu Glu Lys Asn Lys
225                 230                 235                 240

Glu Arg Glu Thr Ile Ser Ile Glu Ile Ile Asp Ile Lys Lys His Leu
                245                 250                 255

Glu Lys Leu Lys Ile Glu Ile Lys Glu Lys Lys Glu Asp Leu Glu Asn
            260                 265                 270

Leu Asn Lys Lys Leu Leu Ser Lys Glu Asn Val Leu Lys Glu Leu Lys
        275                 280                 285

Gly Cys Val Lys Glu Lys Asn Glu Thr Ile Asn Ser Leu Asn Asp Asn
    290                 295                 300

Ile Ile Glu Lys Glu Lys Lys Tyr Lys Leu Leu Glu Tyr Glu Leu Glu
305                 310                 315                 320

Glu Lys Asn Lys Gln Ile Asp Leu Leu Asn Lys Gln Glu Lys Glu Lys
                325                 330                 335

Glu Lys Glu Lys Glu Arg Glu Lys Glu Lys Glu Arg Glu Lys Glu Lys
            340                 345                 350

Glu Lys Glu Tyr Asp Thr Leu Ile Lys Glu Leu Lys Asp Glu Lys Ile
        355                 360                 365

Ser Ile Leu Glu Lys Val His Ser Ile Lys Val Arg Glu Met Asp Ile
    370                 375                 380

Glu Lys Arg Glu His Asn Phe Leu His Met Glu Asp Gln Leu Lys Asp
385                 390                 395                 400

Leu Lys Asn Ser Phe Val Lys Asn Asn Asn Gln Leu Lys Val Tyr Lys
```

```
                405                 410                 415

Cys Glu Ile Lys Asn Leu Lys Thr Glu Leu Glu Lys Lys Glu Lys Glu
            420                 425                 430

Leu Lys Asp Ile Glu Asn Val Ser Lys Glu Glu Ile Asn Lys Leu Ile
        435                 440                 445

Asn Gln Leu Asn Glu Lys Glu Lys Gln Ile Leu Ala Phe Asn Lys Asn
    450                 455                 460

His Lys Glu Glu Ile His Gly Leu Lys Glu Glu Leu Lys Glu Ser Val
465                 470                 475                 480

Lys Ile Thr Lys Ile Glu Thr Gln Glu Leu Gln Glu Met Val Asp Ile
                485                 490                 495

Lys Gln Lys Glu Leu Asp Gln Leu Gln Glu Lys Tyr Asn Ala Gln Ile
            500                 505                 510

Glu Ser Ile Ser Ile Glu Leu Ser Lys Lys Glu Lys Glu Tyr Asn Gln
        515                 520                 525

Tyr Lys Asn Thr Tyr Ile Glu Glu Ile Asn Asn Leu Asn Glu Lys Leu
    530                 535                 540

Glu Glu Thr Asn Lys Glu Tyr Thr Asn Leu Gln Asn Asn Tyr Thr Asn
545                 550                 555                 560

Glu Ile Asn Met Leu Asn Asn Asp Ile His Met Leu Asn Gly Asn Ile
                565                 570                 575

Lys Thr Met Asn Thr Gln Ile Ser Thr Leu Lys Asn Asp Val His Leu
            580                 585                 590

Leu Asn Glu Gln Ile Asp Lys Leu
        595                 600


<210> SEQ ID NO 7
<211> LENGTH: 26
<212> TYPE: PRT
<213> ORGANISM: Plasmodium falciparum

<400> SEQUENCE: 7

Lys Gln Glu Lys Glu Lys Glu Lys Glu Lys Glu Arg Glu Lys Glu Lys
1               5                   10                  15

Glu Arg Glu Lys Glu Lys Glu Lys Glu Tyr
            20                  25


<210> SEQ ID NO 8
<211> LENGTH: 28
<212> TYPE: PRT
<213> ORGANISM: Plasmodium falciparum

<400> SEQUENCE: 8

Lys Asn Leu Lys Thr Glu Leu Glu Lys Lys Glu Lys Glu Leu Lys Asp
1               5                   10                  15

Ile Glu Asn Val Ser Lys Glu Glu Ile Asn Lys Leu
            20                  25


<210> SEQ ID NO 9
<211> LENGTH: 41
<212> TYPE: PRT
<213> ORGANISM: Plasmodium falciparum

<400> SEQUENCE: 9

Ser Lys Lys Glu Lys Glu Tyr Asn Gln Tyr Lys Asn Thr Tyr Ile Glu
1               5                   10                  15

Glu Ile Asn Asn Leu Asn Glu Lys Leu Glu Glu Thr Asn Lys Glu Tyr
            20                  25                  30
```

```
Thr Asn Leu Gln Asn Asn Tyr Thr Asn
        35                  40


<210> SEQ ID NO 10
<211> LENGTH: 29
<212> TYPE: PRT
<213> ORGANISM: Plasmodium falciparum

<400> SEQUENCE: 10

Lys Glu Glu Tyr Glu Asp Lys Met Asn Thr Leu Asn Glu Gln Asn Glu
1               5                   10                  15

Asp Lys Met Asn Ser Leu Lys Glu Glu Tyr Glu Asn Lys
            20                  25


<210> SEQ ID NO 11
<211> LENGTH: 44
<212> TYPE: PRT
<213> ORGANISM: Plasmodium falciparum

<400> SEQUENCE: 11

Lys Gly Leu Lys Lys Glu Val Glu Glu Lys Glu His Lys Arg His Ser
1               5                   10                  15

Ser Phe Asn Ile Leu Lys Ser Lys Glu Lys Phe Phe Lys Asn Ser Ile
            20                  25                  30

Glu Asp Lys Ser His Glu Leu Lys Lys Lys His Glu
        35                  40


<210> SEQ ID NO 12
<211> LENGTH: 30
<212> TYPE: PRT
<213> ORGANISM: Plasmodium falciparum

<400> SEQUENCE: 12

Lys Asp Lys Ser Lys Glu Lys Ile Lys Asp Lys Glu Asn Gln Ile Asn
1               5                   10                  15

Val Glu Lys Asn Glu Glu Lys Asp Leu Lys Lys Lys Asp Asp
            20                  25                  30


<210> SEQ ID NO 13
<211> LENGTH: 29
<212> TYPE: PRT
<213> ORGANISM: Plasmodium falciparum

<400> SEQUENCE: 13

Glu Asp Glu Lys Lys Arg Asn Leu Asn Glu Ile Asn Asn Leu Lys Lys
1               5                   10                  15

Lys Asn Glu Asp Met Cys Ile Lys Tyr Asn Glu Met Asn
            20                  25


<210> SEQ ID NO 14
<211> LENGTH: 28
<212> TYPE: PRT
<213> ORGANISM: Plasmodium falciparum

<400> SEQUENCE: 14

Lys Thr Asn Lys Glu Asn Glu Glu Lys Ile Ile Asn Leu Thr Ser Gln
1               5                   10                  15

Tyr Ser Asp Ala Tyr Lys Lys Lys Ser Asp Glu Ser
            20                  25


<210> SEQ ID NO 15
```

```
<211> LENGTH: 25
<212> TYPE: PRT
<213> ORGANISM: Plasmodium falciparum

<400> SEQUENCE: 15

Ser Asn Asn Asn Ile Arg Thr Asn Glu Tyr Lys Tyr Glu Glu Met Phe
1               5                   10                  15

Asp Thr Asn Ile Glu Glu Lys Asn Gly
            20                  25


<210> SEQ ID NO 16
<211> LENGTH: 25
<212> TYPE: PRT
<213> ORGANISM: Plasmodium falciparum

<400> SEQUENCE: 16

Gly Asn Ile Ser Asn Lys Asn Glu Asn Asn Asn Lys Lys Asn Asn Thr
1               5                   10                  15

Cys Asp Gly Tyr Asp Glu Lys Val Thr
            20                  25


<210> SEQ ID NO 17
<211> LENGTH: 45
<212> TYPE: PRT
<213> ORGANISM: Plasmodium falciparum

<400> SEQUENCE: 17

Ile Lys Thr Met Asn Thr Gln Ile Ser Thr Leu Lys Asn Asp Val His
1               5                   10                  15

Leu Leu Asn Glu Gln Asp Lys Leu Asn Asn Glu Lys Gly Thr Leu Asn
            20                  25                  30

Ser Lys Ile Ser Glu Leu Asn Val Gln Ile Met Asp Leu
        35                  40                  45


<210> SEQ ID NO 18
<211> LENGTH: 25
<212> TYPE: PRT
<213> ORGANISM: Plasmodium falciparum

<400> SEQUENCE: 18

Leu Leu Ser Lys Asp Lys Glu Ile Glu Glu Lys Asn Lys Lys Ile Lys
1               5                   10                  15

Glu Leu Asn Asn Asp Ile Lys Lys Leu
            20                  25


<210> SEQ ID NO 19
<211> LENGTH: 49
<212> TYPE: PRT
<213> ORGANISM: Plasmodium falciparum

<400> SEQUENCE: 19

Ile Cys Ser Leu Thr Thr Glu Val Met Glu Leu Asn Asn Lys Lys Asn
1               5                   10                  15

Glu Leu Ile Glu Glu Asn Asn Lys Leu Asn Leu Val Asp Gln Gly Lys
            20                  25                  30

Lys Lys Leu Lys Lys Asp Val Glu Lys Gln Lys Lys Glu Ile Glu Lys
        35                  40                  45

Leu


<210> SEQ ID NO 20
<211> LENGTH: 77
```

```
<212> TYPE: PRT
<213> ORGANISM: Plasmodium falciparum

<400> SEQUENCE: 20

Val Asp Lys Ile Glu Glu His Ile Leu Asp Tyr Asp Glu Glu Ile Asn
1               5                   10                  15

Lys Ser Arg Ser Asn Leu Phe Gln Leu Lys Asn Glu Ile Cys Ser Leu
            20                  25                  30

Thr Thr Glu Val Met Glu Leu Asn Asn Lys Lys Asn Glu Leu Ile Glu
        35                  40                  45

Glu Asn Asn Lys Leu Asn Leu Val Asp Gln Gly Lys Lys Lys Leu Lys
    50                  55                  60

Lys Asp Val Glu Lys Gln Lys Lys Glu Ile Glu Lys Leu
65                  70                  75


<210> SEQ ID NO 21
<211> LENGTH: 25
<212> TYPE: PRT
<213> ORGANISM: Plasmodium falciparum

<400> SEQUENCE: 21

Leu Asp Glu Asn Glu Asp Asn Ile Lys Lys Met Lys Ser Lys Ile Asp
1               5                   10                  15

Asp Met Glu Lys Glu Ile Lys Tyr Arg
            20                  25


<210> SEQ ID NO 22
<211> LENGTH: 25
<212> TYPE: PRT
<213> ORGANISM: Plasmodium falciparum

<400> SEQUENCE: 22

Leu Asp Glu Asn Glu Asp Asn Ile Lys Lys Met Lys Ser Lys Ile Asp
1               5                   10                  15

Asp Met Glu Lys Glu Ile Lys Tyr Arg
            20                  25


<210> SEQ ID NO 23
<211> LENGTH: 27
<212> TYPE: PRT
<213> ORGANISM: Plasmodium falciparum

<400> SEQUENCE: 23

Thr Ile Ser Ser Leu Ser Asn Lys Ile Val Asn Tyr Glu Ser Lys Ile
1               5                   10                  15

Glu Glu Leu Glu Lys Glu Leu Lys Glu Val Lys
            20                  25


<210> SEQ ID NO 24
<211> LENGTH: 25
<212> TYPE: PRT
<213> ORGANISM: Plasmodium falciparum

<400> SEQUENCE: 24

Ile Ile Asp Ile Lys Lys His Leu Glu Lys Leu Lys Ile Glu Ile Lys
1               5                   10                  15

Glu Lys Lys Glu Asp Leu Glu Asn Leu
            20                  25


<210> SEQ ID NO 25
<211> LENGTH: 38
```

```
<212> TYPE: PRT
<213> ORGANISM: Plasmodium falciparum

<400> SEQUENCE: 25

Ile Lys Thr Met Asn Thr Gln Ile Ser Thr Leu Lys Asn Asp Val His
1               5                   10                  15

Leu Leu Asn Glu Gln Asp Lys Leu Asn Asn Glu Lys Gly Thr Leu Asn
            20                  25                  30

Ser Lys Ile Ser Glu Leu
        35
```

*PLASMODIUM FALCIPARUM* AND *PLASMODIUM VIVAX* VACCINE

The present invention relates to a vaccine V comprising (A) at least one isolated polypeptide strand P comprising or consisting of at least nine consecutive amino acid moieties of the repetitive organellar protein, putative of *Plasmodium falciparum* or the hypothetical protein PVNK_04523 of *Plasmodium vivax* or a polynucleotide strand encoding for such polypeptide; and (B) at least one pharmaceutically acceptable carrier or excipient. Furthermore, the present invention refers to an antibody binding to the repetitive organellar protein, putative of *Plasmodium falciparum* or the hypothetical protein PVNK_04523 of *Plasmodium vivax* or a polynucleotide strand encoding therefore, and to a method of generating such antibodies and uses thereof.

Malaria is a life-threatening disease caused by parasites that are transmitted to people through the bites of infected female *Anopheles* mosquitoes. There are 5 parasite species that cause malaria in humans, and 2 of these species, *P. falciparum* and *P. vivax*, pose the greatest threat. *P. falciparum* is responsible for most malaria-related deaths globally. *P. vivax* is the dominant malaria parasite in most countries outside of sub-Saharan Africa.

The malaria life cycle begins when the sporozoite stages of the *P. falciparum* parasite developing inside the salivary glands of an infected *Anopheles* female mosquito are transmitted to humans during a blood meal. Once inside the bloodstream, sporozoites travel to the liver, where they multiply and transform into infectious stages named merozoites. This represents the liver stage, a pre-erythrocytic stage. Each merozoite released from the liver invades an erythrocyte, inside which it grows and multiplies. Once the intraerythrocytic cycle is completed, the infected erythrocyte membrane lyses, releasing newly formed merozoites that go on to invade more erythrocytes by means of specialized invasion processes. This represents the blood stage. Blood stage parasites are responsible for the clinical manifestations of the disease.

According to the latest WHO estimates, released in December 2016, there were 212 million cases of malaria in 2015 and about 429,000 deaths. Some population groups are at considerably higher risk of contracting malaria, and developing severe disease, than others. Children under 5 are particularly susceptible to infection, illness and death; more than two thirds (70%) of all malaria deaths occur in this age group. Partial immunity against malaria is developed over years of exposure, and while it never provides complete protection, it does reduce the risk that malaria infection will cause severe disease.

The control of the mosquitos (the so-called vector) is the main way to prevent and reduce malaria transmission (vector control). Two forms of vector control—insecticide-treated mosquito nets and indoor residual spraying—are effective in a wide range of circumstances. Much of the success in controlling malaria is due to vector control. However, malaria-endemic areas of sub-Saharan Africa and India are causing significant concern due to high levels of malaria transmission and widespread reports of insecticide resistance. Rotational use of different classes of insecticides for IRS is recommended as one approach to manage insecticide resistance.

Malaria can be prevented through chemoprophylaxis (with antimalarial drugs), which suppresses the blood stage of malaria infections, thereby preventing malaria disease. Resistance to antimalarial medicines is a recurring problem. Resistance of *P. falciparum* to previous generations of medicines, such as chloroquine and sulfadoxine-pyrimethamine (SP), became widespread in the 1950s and 1960s. A good available treatment, particularly for *P. falciparum* malaria, is artemisinin-based combination therapy (ACT). An ACT contains both, the drug artemisinin and a partner drug. In recent years, parasite resistance to artemisinin has been detected in 5 countries of the Greater Mekong subregion: Cambodia, Lao People's Democratic Republic, Myanmar, Thailand and Viet Nam. In parallel, there were reports of increased resistance to ACT partner drugs in some settings.

All these means for treating bear considerable drawbacks. It has also been tried to prepare a variety of vaccines against malaria. Malaria vaccines are considered amongst the most important modalities for potential prevention of malaria disease and reduction of malaria transmission. Research and development in this field has been an area of intense effort by many groups over the last few decades.

Despite this, there is currently no licensed malaria vaccine. Malaria vaccines can address either the pre-erythrocytic-stage or the blood-stage (more rarely transmission-blocking vaccines are investigated). Also pre-erythrocytic malaria vaccines have been developed. RTS, S/AS01 (RTS, S) is an injectable pre-erythrocytic vaccine, directed against sporozoites, that provides partial protection against malaria in young children. The vaccine is being evaluated in sub-Saharan Africa as a complementary malaria control tool that potentially could be added to (and not replace) the core package of WHO-recommended preventive, diagnostic and treatment measures.

Furthermore, blood-stage malaria vaccines have been developed. Erythrocyte invasion by merozoites, the blood-stage, is an essential step in *Plasmodium falciparum* infection and leads to subsequent disease pathology. Proteins both on the merozoite surface and secreted from the apical organelles (micronemes, rhoptries and dense granules) mediate the invasion of erythrocytes; some of the molecules have been regarded as targets in the development of an anti-malaria vaccine.

Unfortunately, the anti-malaria vaccines known in the art so far bear rather limited effectiveness. Therefore, there is still the need for providing further effective anti-malaria vaccines. It has been shown that several rhoptry polypeptides generally qualify as potential vaccine candidates. This is of particular interest, because there are only about thirty proteins present in the rhoptries. One example could be the Rhoptry-associated membrane antigen (RAMA) (Topolska et al., 2004).

The rhoptry protein Pch ROPE—Repeated Organellar Protein; Pch ROPE was first identified, described and characterized in a BALB/c mouse model from the rodent malaria parasite *Plasmodium chabaudi*. Examples for ROPE peptides that could, in principle, have some antigenic properties have been mentioned by Villard et al., 2007, and Kulangara et al., 2009. These documents do, however, not teach a vaccine suitible for efficiently treating or preventing malaria in a patient by means of active immunization. Antigens of *Plasmodium vivax* are not considered at all.

U.S. Pat. No. 8,716,443 teaches that the serum of malaria patients may comprise antibodies against malaria proteins, in particular against a truncated version of 844 amino acid moieties or less of a hypothetical protein of *Plasmodium falciparum*(MAL6P1.37 (PFF0165c)). However, no vaccine based on rhoptry protein Pf ROPE or Pv ROPE is taught or suggested.

The sequence of ROPE was originally obtained from cDNA—and genomic DNA—libraries of *Plasmodium cha-*

*baudi* 96V (Werner et al., 1998, Mol Biochem Parasitol. 94(2):185-96). (SEQ ID NO: 1): polypeptide sequence of the Repeat Organellar Protein of *Plasmodium chabaudi* (cf., also GenBank: AAC63403):

```
MIFNLKKSKKNEDGSNKDSKKTNETSGIEKKEKSNKWYNKIVNNSTKKDK

DKNNDSIVYDDESKVGENDHHMKEYELEDQLKETLKSITALSIKVKEYEV

KIEELEKELKLEKEKQINKEYEKELNEKSEFIKRQMELLKEKELNINLKE

NKINNKEIITLKREEKLNDIESEYIEKNKEKEKLNYEVTNIKMSLDKLTC

EVQEKKDNLEKINKKVIEKENNLRELKEFMKEKNEIIESLDGTINDKKNA

YEKLEISFEEKRKMIEMLDSKLIEKEENFANKQAKLEKENEIIIEKLKDI

ESREKDFKSKEEKFASMENELNTLKSDLSKNACQMEVYKLEIKDLSQSLV

EKEREIFEIKNEYDDKINNMKEKLSSINDKGIDNTVLHSEEEKINKLLKE

KETELNEIHKKYNLEIETIKNELNEKEEELEKNKKAHTVEVTNLTKEIKL

LEKKTEDAKEGHKNELNELNNQLSKLNKEKDNIKNENTELNDKISSLNSE

VNILNKDKQTLGNDIKTLNDLINNLKNEINTSDNKMNKMKEDLAMLNEEM

EGKCVVIDEIEKKYKNEIFMLEEKLKEKENYADLNDEISILRNSIYVKEK

EFIEMKEFYENKINLFNKNFEEKKNIYENELNSLRLKYDNEQGLIKQIDE

LNIQKLKTEEKYLQLYNDNMHMFRSICTKIDMPYSENIKGSDLVDFVTAY

IKRRDESSSDANPDTTHKEMVAELEKRHAAIVAELEEKHKEEIAKLGEGH

KEVVLRLGEQHKEETIILEEKHKDVVTKLGEQHKENIIKLEEEHKDVVTK

LGDQYKEEIAKLKEEHAVVVAELEEKHKLGEGHKEMVDELEKRHADFVEG

LEEKHKAETAKLEEGHKSEMNEVEKRHADFVEGLEEKHKAETAKLGEGHR

EVVAGLEEKHKEVVAELEEKHKEEIAKLEEGHKEVMAELGEKHKEVVAGL

EAKHNLEEGHKEMVAELEKRHADLVAVLEEQHKAEIIKLGEEHKEVVAGI

EEKYKVEAIKLAEEHKDVVTKLGEQHKEEIAKLEDGHKEVVNEVEKKNAS

LLNMLEENHKNEMIKLKEEHKESASDLVEKLYQKDEEVKNSNNKIEELTN

VIKDLNDSIMCYKKQILEEVEKRNEYNEEINKLKIVQNEMKDMNDKKILE

KENEIKKLNKKLSNYKVFETKENTYKNSEMVVNENKERIIVDSVCKENIS

ESDVEGKGGNLKMTLSLKKKERNIFSINDNKNESSELVDTIKSAYINKIE

MYKKEIEDNGKNIEDLKNKILDLSNELINLENMKNVLTDENNNLKKEIEI

KDNKLNEKEKNENTEILNLNDDIIKLKKEISEWKDEEEKLTKENIKLKND

IEQINKEYKIKEENLMIKFNENINEVTSLKNQIEIEKMKLEELNKNYELL

LAEKRETNMSISNDDNKIVENNILEDTDSKQNNLNKNVEDKTGDDINCEK

NNDQAKEISYLKDEIKKISMLYGEELNRKNSYDEKVKNLTNELKELKIRN

KKGEEAIAELNKLKNIKEKNKSVKQNDESSSNNIITKDGDKTPEYVSNDD

KIQKDWKANLVLKLKEKPDLWDNINSLEKENFRVMSIVKENKNVQNDKIV

GIYSYFKKCEKELKNDMLVICLVLKDILSILFLNDNFVNLFEKIDKILWK

QMYIPTEIRILFLRYFSFLDKLRNYVKCVNEEYVNNERYEYSWALFQTYL

ETASNLKKEMIYYVLEKAEKDSCENNSSNFDKPKITDILNFSKDSIRLKT

IAQLRKELNFEREAKNILNYDYQIILNKYHECLRKLKIVKNMARELDFNY

NVSSKFSIKKELEMCSDENDEFKYNNIKNNEEKNDTIKDPKHNNLIQKII
```

-continued

```
NLQRNKKTEKKKNNLVNEINTMYPGDTTPKGKIFTTNDNSKQNEILKKKD

NINNNITHKNVYTGQVKNIFNEPVERKVRISFIHKSPFN
```

(Pch ROPE is encoded by an intronless gene. Its dominant structural features are that of a mainly alpha-helical protein, that will build a coiled-coil structure and has a putative transmembrane anchor sequence close to its C-terminal end. Partial sequences of the Pch ROPE DNA sequence were expressed as a recombinant protein in *E. coli* (Werner et al., 1998). These Pch ROPE partial protein sequences were use to further characterize Pch ROPE.

Pch ROPE is a Natural Antigen

BALB/c mice were, after infection with *Plasmodium chabaudi* 96V, treated with 1 mg of Nivaquine, once 40% of their red blood cells were infected with *Plasmodium chabaudi* 96V. Here BALB/c mice survived an otherwise 100% lethal infection with *Plasmodium chabaudi*. Mice were now immune against any further infection with *Plasmodium chabaudi* 96V. Sera from these mice were immune-sera. It was shown in Western-blot studies that immune-sera recognize recombinant partial Pch ROPE protein sequences, demonstrating that Pch ROPE is a natural antigen occurring during an infection of BALB/c mice with *Plasmodium chabaudi* 96V (Werner et al., 1998).

Pch ROPE is a Rhoptry Protein

Antisera against recombinant fragments of the Pch ROPE protein were raised in Fisher rats. These anti-sera were subsequently used in IF—Indirect Immunofluorescence microscopy on erythrocytes of BALB/c-mice infected with *Plasmodium chabaudi* 96V. Pch ROPE can be localized in the rhoptry organelles of *Plasmodium chabaudi* 96V during the more mature blood-stages and Pch ROPE can be localized around the entire erythrocyte membrane during the early stage of the invasion of the BALB/c erythrocyte by *Plasmodium chabaudi* 96V (Werner et al., 1998). The localization of Pch ROPE in the rhoptry organelles, which are known to be involved in the invasion process, and the localization of Pch ROPE at the membrane of the newly infected erythrocyte suggest a direct role of the Pch ROPE protein during the invasion process of the erythrocyte by *Plasmodium chabaudi* 96V.

Pch ROPE is a Protective Antigen

BALB/c mice, immunized with recombinant parts of Pch ROPE, were protected from an otherwise 100% lethal infection with *Plasmodium chabaudi* 96V. It is important to emphasize here, that in the presented BALB/c mice—*Plasmodium chabaudi* 96V model, which we used over a period of about 4 years, not a single unprotected BALB/c mice did ever survive an infection with *Plasmodium chabaudi* 96V.

The Pch ROPE Homologues (orthologues) of *Plasmodium falciparum* and *Plasmodium vivax* are Potential Vaccine Candidates Survival of mice immunized with recombinant parts of Pch ROPE is a direct proof of Pch ROPE being a protective antigen in this model and thus suggesting that the Pch ROPE protein homologue (orthologue) of the human malaria parasites (*Plasmodium falciparum* and *Plasmodium vivax*) being potential vaccine candidates for human malaria disease.

In this context it seems to be noteworthy that Pch ROPE shares some similarities with other vaccine candidates located in the rhoptries, e.g. the Rhoptry-associated membrane antigen (RAMA) (Topolska et al. Infect Immun (2004) June; 72(6):3325-30) of *Plasmodium falciparum*, for example with respect to its transient location to the erythrocyte membrane during the early invasion stages of the erythrocyte. The homologue (orthologue) of Pch ROPE is the "repetitive organellar protein, putative" of *Plasmodium falciparum* 3D7 (GenBank: CZT98043.1) [formerly named *Plasmodium falciparum* 3D7 "Kid domain containing protein" (NCBI Reference Sequence: XP_0013495431)] SEQ ID NO: 2 and SEQ ID NO: 4 and the "hypothetical protein PVNG_04523" of *Plasmodium vivax* North Korean (GenBank: KNA01322.1) SEQ ID NO: 3 and SEQ ID NO: 5 for the two major human malaria parasite species.

The three homologues (orthologues) share a comparable size: Pch ROPE with 1939 amino acids the "repetitive organellar protein, putative" of *Plasmodium falciparum* 3D7 with 1979 amino acids and the "hypothetical protein PVNG_04523" of *Plasmodium vivax* North Korean with 1887 amino acids. The three homologues (orthologues) share an identical predicted overall secondary structure: large alpha-helical segments, extended non-helical segments at the N- and C-termini of the protein, a predominantly coiled-coil structure and a sequence at identical sites upstream from the C-termini representing a putative transmembrane segment, thus suggesting further a homologous biological function of the three homologous (orthologous) proteins.

A vaccine comprising an isolated polypeptide strand P of at least nine consecutive amino acid moieties of the repetitive organellar protein, putative of *Plasmodium falciparum* 3D7 or the hypothetical protein PVNG_04523 of *Plasmodium vivax* North Korean as well as a polynucleotide strand encoding for such polypeptide serve as effective means for targeting *Plasmodium falciparum* or *Plasmodium vivax*. This can be used in a medicinal as well as a non-medicinal context for generating antibodies.

Accordingly, a first aspect of the invention relates to a vaccine V comprising:

(A) at least one isolated polypeptide strand P comprising or consisting of at least nine consecutive amino acid moieties of the repetitive organellar protein, putative of *Plasmodium falciparum* 3D7 (SEQ ID NO: 2) and/or the hypothetical protein PVNG_04523 of *Plasmodium vivax* North Korean (SEQ ID NO: 3) or a polynucleotide strand encoding for said polypeptide strand P; and (B) at least one pharmaceutically acceptable carrier or excipient.

In a preferred embodiment, the vaccine V comprises:

(A) at least one isolated polypeptide strand P comprising or consisting of at least nine consecutive amino acid moieties of SEQ ID NO: 2 or SEQ ID NO: 3 or a polynucleotide strand encoding for said polypeptide strand P; and (B) at least one pharmaceutically acceptable carrier or excipient.

In another preferred embodiment, the vaccine V comprises:

(A) at least one isolated polypeptide strand P comprising or consisting of at least nine consecutive amino acid moieties of SEQ ID NO: 2 and (concomitantly) SEQ ID NO: 3 or a polynucleotide strand encoding for said polypeptide strand P; and (B) at least one pharmaceutically acceptable carrier or excipient.

As used herein, the vaccine of the present invention is designated as "vaccine V" in order to ease finding of the vaccine of the present invention in the text. It will be understand that the designation "V" does not have a technical meaning and can also be omitted without altering the scope of the present invention. As used herein, the polypeptide strand of the present invention is designated as "polypeptide strand P" in order to ease finding of the polypeptide strand of the present invention in the text. It will be understand that the designation "P" does not have a technical meaning and can also be omitted without altering the scope of the present invention.

It will be understood that the term "at least nine consecutive amino acid moieties of" in the context of a certain sequence may embrace any peptide strand that overlaps with nine or more consecutive amino acid moieties of the respective protein sequence.

The polypeptide sequence of the full repetitive organellar protein, putative of *Plasmodium falciparum* 3D7 (GenBank: CZT98043.1) (SEQ ID NO: 2):

```
MVFTFKNKKKKKEASSDKVSKESFNEEDNENNEKREKSDSWYKKIIETKG
KSKTKYKNDNSLDDNINEDIINNNNNNNNDNNNDNNNDNNNDNNNDNNND
NNNENNNDNNNFNNYSDEISKNIIHKDNELENQLKDTLKSISSLSNKIVN
YESKIEELEKELKEVKDKNIDNNDYENKLKEKEDFVKQKIDMLNEKENLL
QEKELDINKREKKINEKEKNIIKKEETFHNIEKEYLEKNKERETISIEII
DIKKHLEKLKIEIKEKKEDLENLNKKLLSKENVLKELKGCVKEKNETINS
LNDNIIEKEKKYKLLEYELEEKNKQIDLLNKQEKEKEKEKEREKEKEREK
EKEKEYDTLIKELKDEKISILEKVHSIKVREMDIEKREHNFLHMEDQLKD
LKNSFVKNNNQLKVYKCEIKNLKTELEKKEKELKDIENVSKEEINKLINQ
LNEKEKQILAFNKNHKEEIHGLKEELKESVKITKIETQELQEMVDIKQKE
LDQLQEKYNAQIESISIELSKKEKEYNQYKNTYIEEINNLNEKLEETNKE
YTNLQNNYTNEINMLNNDIHMLNGNIKTMNTQISTLKNDVHLLNEQIDKL
NNEKGTLNSKISELNVQIMDLKEEKDFLNNQIVDLSNQIDLLTRKMEEKE
NKMLEQENKYKQEMELLRGNIKSSENILNNDEEVCDLKRKLSLKESEMKM
MKEEHDKKLAELKDDCDVRIREMNEKNEDKINMLKEEYEDKINTLKEQNE
DKINTLKEQNEDKINTLKEEYEHKINTMKEEYEHKINTLNEQNEHKINTL
NEQNEHKINTMKEEYEDKMNTLNEQNEDKMNSLKEEYENKINQINSNNEI
KIKDVVNEYIEEVDKLKVTLDEKKKQFDKEINYAHIKAHEKEQILLTEME
ELKCQRDNKYSDLYEKYIKLIKSICMIINIECCDDIENEDIIRRIEEYIN
NNKGLKKEVEEKEHKRHSSFNILKSKEKFFKNSIEDKSHELKKKHEKDLL
SKDKEIEEKNKKIKELNNDIKKLQDEILVYKKQSNAQQVDHKKKSWILLK
DKSKEKIKDKENQINVEKNEEKDLKKKDDEIRILNEELVKYKTILYNLKK
DPLLQNQDLLSKIDINSLTINEGMCVDKIEEHILDYDEEINKSRSNLFQL
KNEICSLTTEVMELNNKKNELIEENNKLNLVDQGKKKLKKDVEKQKKEIE
KLNKQLTKCNKQIDELNEEVEKLNNENIELITYSNDLNNKFDMKENNLMM
KLDENEDNIKKMKSKIDDMEKEIKYREDEKKRNLNEINNLKKKNEDMCIK
YNEMNIKYGDICVKYEEMSLTYKETSLKYEQIKVKYDEKCSQYDEIRFQY
DEKCFQYDEINKKYGALLNINITNKMVDSKVDRNNNEIISVDNKVEGIAN
YLKQIFELNEEIIRLKGEINKISLLYSNELNEKNSYDINMKHIQEQLLFL
EKTNKENEEKIINLTSQYSDAYKKKSDESKLCGAQFVDDVNIYGNISNNN
IRTNEYKYEEMFDTNIEEKNGMHLSKYIHLLEENKFRCMKIIYENENIKS
```

-continued

```
SNKIIGLYNYSRYYGLREDLCKEEIVPSKIGNISNKNENNNKKNNTCDGY
DEKVTIVLCIILNEIIKFLFLNDEYVLLFEKIHKNVWKRMYIPEEIKFFI
LKYITLLNNLRDYIISVHNNMKNEKYDECWFLFQHYFERSSDVRKEMVHF
LLERKSQENLISFKSKLKSKKEKILTMDILNFSKEHMQLKTIAHLRKEIN
YEKLSKDTLNRDYNLLLYKYQECVSKLKRVKNLMKEINQNVFIEKYDDIS
KELDNFSDGYNEQNEQHVMDPILLNNNKNKNNKLITEHNNPIINRLTNFT
QNRDSKYKNKIMDDVKQRKINSTMNNTNKNGINIIYNHYENLNKPNYNDN
INRLNSYHQNIHIANSIHPNRNQNKSFLTNQANSTYSVMKNYINSDKPNL
NGKKSVRNIFNEIVDENVNKTFVHKSVFF
```

The polypeptide sequence of the full length hypothetical protein PVNG_04523 of *Plasmodium vivax* North Korean (GenBank: KNA01322.1) (SEQ ID NO: 3):

```
MVFKFKKKKKEESSDKLSKQSQNDEGNANEEAEKKDHKSNSWYKKIIDNA
IITKSKHDDKEEQEEEKNGEGNDSRAMERNKDYQLEEQLKETLRSITSLS
TKIVNYETKIEDLEKELKMEKDKQVDKAYEKELKEKENFIKQKIGMLNEK
ENLLNEKELDINMREEKINDREMFISKKEDKLNDMQEQYLEKNKEKEKLH
FEIADIKISLEKLKYEVKDKKDCLENVSNKVILKENTLRELKEFIREKNE
MIESLNEKITEKEKIYEQLGKDVEEKRKIIELLDMKANEKEKYFEEKIKE
LEKEQNALLQKLNNVKMREKEVETRENDFLHMEDELNDLRSSFSKNDCQL
KIYKLEIKDLSSALVEKEREILDLKNTYDGEICSLKDQIKEKEKEIAKGS
SSGGDVGAQDEPASEVESEEKADPKEEGVENSLTDLLKMKERELHEMKEK
YAKEIDTLNSELNEKKKEFVEAKNSHINQINNLNDEIEESESKMAELKSG
YEMEIKKLRSEINAVHEEKYLLSNEKQTLSGEIDKLNEEKKSLASEKEEL
HNKITTLNSEIGTLHVEKQALTGEINTLNDLIHTLKNEISSSDNLISKLK
EQMNAINEEKEGKEKLITEIENNYKNEINALKEKLKDTDNQVSISIREEM
DHLKCVLGETEKENKQMKEDYHKKIKQYDEELLSKQQYFEEELNNIRIKS
HEKEQILILKNDELKESKLKTEEKYLKLYDDKMSLLRNMCSKVGLPYSDE
VSVEELLERVGNYVSGMGEPGGAAHRGEQSEEPHEGQSIVEETNEPLLSA
QTADNANSLEDKTTLQALQKELESVQEEYREEVAKMKSYLAMKEKTIEES
NHTIAELTGKINSLNDTISFFKVNHSEEKINSYMDEINSLSLTLSELKAN
NEQEQLENRNEIARLSEELSGYKRRADEQCRKRSSEKERSESKRGDTRGD
SEKEQISESDVEGGGNLKSFLHFPLRKIKGKKRKASKTEKEIQTELRRNE
PENEQSEKNEKAPRGDSLEVDQYKKELEEKAKIIEDLKDKICTLTNEVMD
LKNLKNELAERDSSLAKAGEEAERQREQLDTLSAQLGGANGEVERLSEEV
ERLNEEVEKLKEGEAQSWGEAEKWKGEAEKWKEDAAKWEADTVKLKEDAA
KWESDAVKWESDAETWRKEAEELRSSANQLNEELCSKENNYVLKLNENVG
VIQKMKDSIDAREKEKENYVREINDLRNELEGLKLKHDALSETYKQLEGK
SSPPSGDDPPGGDNYTSEGENKLSIPNENCEMDQAEEANANPGVPKSEIA
TEGGVSSLAVNDYISEIAHLKEEINRLTLLYSNELNEKNSSDIRTKELLS
QLKELEVRDKENEEKIAALSKMNEKMKAKNEKLKSGKWLSRKDHAPNEEV
DIAGEERKKKEKEKVPHPDVKEESLSSEHVNTLEGNTYRVMRIVDESSPA
```

-continued

```
GGGQIIGSYLYTKKVEDLHAVNGANVADAQLAEKNAITVVCLILSEILSL
LFLNDQFVNAFERINKSLWKLMYMPEEIKALLLRYFSFMSKLRDYAKEVH
GRVENERYEDSQRQDNQRYDDSWLLFQNYLETSSSIKRDLVCFILEEKEN
ELAELGEHYGGGMRKGEEVIGGVRGVRGGKIADIINLSKDEMRLKTIAQL
RRDLDFEKKSKTLLSRDYQLLLYKYQECVRKLKRVKNMIRQLNLNDHSNR
GSFALNRELDRCSEVSNERGFNEEGGDEDSHGNYKNCILQDNNNNSSVNN
YNSSNTKLESRENVLIKDLINLRRAQKVKGNNLIHWGRPSMMMGGRCHQD
ASHVVRAMVNGPKISSQNIFAHMNRLSNAPKISDHLDDMKKMKNIFNEFV
ETRGDVTFVHRSPFCET
```

The polynucleotide strand encoding for the at least nine consecutive amino acid moieties of SEQ ID NO: 2 can be any sequence suitable for this purpose. Preferably, it is a part of or the whole sequence according to the repetitive organellar protein, putative of *Plasmodium falciparum* 3D7 (GenBank: CZT98043.1): 1..1979/locus_tag="PF3D7_0203000"/coded_by="complement (LN999943.1:141625..147564)" (SEQ ID NO: 4):

```
ATGGTATTCACGTTCAAAAATAAGAAAAAGAAAAAAGAAGCTAGTTCAGA
TAAAGTAAGCAAAGAATCATTTAATGAGGAAGATAATGAAAATAATGAAA
AGAGGGAAAAAAGCGATTCATGGTATAAAAAAATAATAGAAACTAAAGGA
AAAAGTAAAACTAAATATAAAAATGATAATTCCTTAGATGATAATATTAA
TGAGGACATAATAAATAATAATAATAATAATAATAATGATAATAATAATG
ATAACAATAATGATAATAATAATGATAATAATAATGATAATAATAATGAT
AATAATAATGAGAATAATAATGATAATAATAATTTTAATAATTATAGCGA
TGAAATATCAAAAAATATTATACATAAAGACAATGAGCTAGAAAACCAGC
TTAAGGATACATTAAAGTCCATTAGTTCGTTGTCGAATAAAATTGTGAAT
TACGAAAGTAAAATTGAAGAATTAGAAAAAGAATTAAAAGAAGTAAAGGA
TAAGAATATTGATAATAATGATTATGAAAATAAATTAAAAGAAAAAGAAG
ATTTTGTTAAACAAAAAATTGATATGCTAAATGAAAAAGAAAATCTTTTA
CAAGAAAAAGAATTAGATATTAATAAAAGAGAAAAGAAAATTAATGAAAA
AGAAAAGAATATAATAAAAAAGGAAGAAACATTTCATAATATAGAAAAAG
AGTATTTAGAAAAAAATAAAGAAAGAGAAACGATTTCTATAGAAATTATA
GATATTAAAAAACATCTAGAAAAACTAAAAATAGAAATAAAAGAAAAAAA
AGAAGATTTAGAAAATTTAAATAAAAAATTGTTATCAAAAGAAAATGTAC
TAAAAGAATTAAAAGGATGTGTTAAGGAAAAAAATGAAACCATTAATTCA
TTGAATGATAATATTATTGAAAAAGAAAAAAAATATAAATTATTAGAATA
TGAGTTGGAAGAAAAAAATAAACAAATTGATTTATTAAACAAACAAGAAA
AAGAAAAGGAAAAGGAGAAGGAAAGGGAAAAGGAGAAGGAAAGGGAAAAG
GAAAAAGAAAAGGAATATGATACATTAATCAAAGAATTAAAAGATGAAAA
GATTTCCATTTTAGAAAAAGTTCATTCCATTAAAGTAAGAGAAATGGATA
TTGAAAAAAGAGAACATAATTTCCTTCATATGGAAGATCAATTAAAAGAT
TTAAAAAATAGTTTTGTAAAGAATAATAATCAATTAAAAGTATATAAATG
```

-continued

TGAAATAAAGAATCTTAAAACCGAATTAGAAAAAAAAGAAAAAGAATTAA

AAGATATAGAAAATGTATCTAAAGAAGAAATAAATAAATTAATAAACCAA

TTAAATGAAAAGGAGAAACAAATTCTTGCGTTTAATAAAAATCATAAAGA

AGAAATTCATGGATTGAAAGAAGAATTAAAAGAATCTGTGAAAATAACCA

AAATAGAAACACAAGAGTTACAAGAAATGGTAGACATCAAACAAAAAGAG

TTAGACCAATTGCAGGAAAAATATAACGCACAAATAGAAAGTATAAGCAT

CGAATTAAGTAAAAAAGAGAAGGAATATAATCAATATAAAAATACTTATA

TAGAAGAAATAAATAATTTAAATGAAAAATTAGAAGAAACTAATAAAGAA

TATACGAATTTACAAAATAATTATACAAATGAAATAAATATGTTAAATAA

TGATATACATATGTTAAATGGCAATATAAAAACCATGAATACACAAATAA

GTACTTTAAAAAATGATGTACATTTGTTAAATGAACAAATAGATAAATTA

AATAATGAAAAGGGTACATTAAATAGTAAAATTAGTGAATTGAATGTTCA

AATTATGGATTTAAAAGAGGAAAAAGATTTCTTAAATAATCAAATTGTAG

ATTTAAGTAATCAAATTGATTTGTTAACAAGAAAAATGGAAGAGAAGGAA

AATAAAATGTTGGAACAGGAGAATAAGTATAAACAAGAGATGGAACTCTT

AAGGGGGAATATAAAAAGTTCTGAGAATATTTTAAACAATGACGAAGAGG

TGTGTGATTTAAAAAGGAAATTAAGTTTGAAGGAAAGTGAAATGAAAATG

ATGAAGGAGGAACATGATAAGAAGTTGGCTGAGTTGAAAGATGATTGTGA

TGTGAGGATACGGGAGATGAATGAAAAGAATGAAGATAAAATTAATATGT

TAAAGGAAGAATATGAAGATAAAATTAATACGTTGAAGGAACAAAATGAA

GATAAAATTAATACGTTAAAGGAACAAAATGAAGATAAAATTAATACATT

GAAAGAAGAGTATGAACATAAAATTAATACGATGAAGGAAGAATATGAAC

ATAAAATTAATACGTTGAATGAACAAAATGAACATAAAATTAATACGTTG

AATGAACAAAATGAACATAAAATTAATACGATGAAGGAAGAATATGAAGA

TAAAATGAACACGTTGAATGAACAAAATGAAGATAAAATGAATTCGTTGA

AGGAAGAGTATGAAAATAAGATAAATCAAATTAATAGTAATAATGAAATA

AAAATAAAAGATGTAGTGAATGAATATATTGAAGAAGTGGACAAATTAAA

AGTTACTTTGGATGAAAAAAAAAAACAATTTGATAAAGAAATAAATTACG

CACATATCAAAGCTCATGAAAAGGAGCAAATATTATTAACAGAAATGGAA

GAATTAAAATGTCAGAGGGATAATAAATATTCAGATTTATATGAGAAATA

TATTAAACTAATAAAAAGTATTTGTATGATAATTAACATTGAATGTTGTG

ATGATATAGAAAATGAAGATATTATAAGAAGAATTGAAGAATATATAAAT

AATAACAAAGGCTTGAAAAAAGAAGTAGAAGAAAAAGAACATAAAAGACA

TTCCTCCTTTAATATTTTAAAAAGTAAAGAAAAGTTTTTTAAAAATAGCA

TAGAAGATAAAAGTCATGAATTAAAAAAAAAACATGAAAAAGATTTATTA

TCAAAAGATAAAGAAATTGAAGAAAAGAATAAAAAAATAAAAGAACTGAA

TAATGATATAAAAAAGTTACAAGATGAAATATTAGTATATAAAAAACAAA

GTAATGCACAACAAGTAGATCATAAAAAGAAAAGTTGGATTCTTCTTAAA

GATAAATCTAAAGAGAAAATAAAAGATAAAGAAAATCAAATAAATGTAGA

AAAAAATGAAGAAAAGGATTTAAAAAAAAAAGATGATGAAATAAGAATTT

TAAATGAAGAACTTGTAAAATATAAAACAATTTTATATAATTTAAAAAAA

GATCCATTATTACAAAATCAAGATTTATTATCAAAAATTGACATAAATTC

TTTAACAATAAATGAAGGAATGTGTGTAGATAAAATAGAAGAGCACATTT

TGGATTATGATGAAGAAATAAATAAAAGCAGATCTAATTTGTTTCAACTA

AAAAATGAAATATGTTCTTTAACAACTGAGGTTATGGAACTTAATAATAA

GAAAAATGAATTAATTGAAGAAAATAATAAATTAAATTTAGTAGATCAAG

GAAAGAAGAAATTAAAAAAGGATGTGGAAAAACAAAAAAAAGAAATAGAG

AAATTAAATAAACAATTAACAAAATGTAATAAACAAATAGATGAATTAAA

TGAAGAAGTGGAAAAATTAAATAATGAAAATATTGAATTAATTACATATT

CAAATGATTTAAATAACAAATTTGATATGAAAGAAAATAATCTTATGATG

AAATTAGATGAAAATGAAGATAATATAAAGAAAATGAAAAGTAAAATTGA

TGATATGGAAAAAGAAATAAAATATAGAGAAGATGAAAAAAAAAGAAATT

TAAATGAAATTAATAATTTAAAGAAAAAGAATGAAGATATGTGTATTAAA

TATAATGAAATGAATATTAAGTATGGAGATATTTGTGTAAAATATGAAGA

AATGTCTCTTACGTATAAAGAAACATCTCTTAAATATGAGCAAATTAAAG

TGAAATATGATGAAAAGTGTTCTCAATATGACGAAATACGTTTTCAATAT

GATGAGAAATGTTTTCAATATGATGAGATAAATAAGAAATATGGTGCTTT

ATTAAATATAAATATTACTAATAAAATGGTTGATTCAAAAGTGGATAGAA

ATAATAATGAAATAATTTCAGTAGATAATAAAGTAGAAGGAATTGCGAAT

TATTTAAAACAAATATTTGAATTAAATGAAGAGATCATACGATTAAAAGG

AGAAATAAATAAAATTAGCTTATTATATAGTAATGAATTAAATGAGAAAA

ATAGTTATGATATAAACATGAAACATATACAAGAACAATTACTTTTTTTG

GAAAAGACAAATAAAGAAAATGAAGAAAAAATAATTAATTTGACTAGCCA

ATATTCTGATGCATACAAGAAGAAGAGTGATGAATCTAAATTATGTGGTG

CACAGTTTGTTGATGATGTTAATATATATGGAAATATATCAAATAATAAT

ATAAGAACAAATGAATATAAATATGAAGAGATGTTTGATACGAATATAGA

AGAGAAGAATGGTATGCATTTATCTAAGTATATTCATCTATTAGAAGAAA

ATAAATTTCGATGTATGAAAATAATTTATGAAAATGAAAATATAAAAAGT

AGTAATAAAATAATTGGATTGTATAATTATTCAAGGTATTATGGGTTAAG

AGAAGATTTGTGTAAAGAAGAAATCGTTCCTTCAAAAATAGGAAATATAT

CTAATAAAAATGAAAATAATAATAAGAAGAACAACACTTGTGATGGTTAT

GATGAGAAGGTTACAATAGTTTTATGCATTATATTAAATGAAATAATAAA

ATTTTTATTTTTAAATGACGAATATGTATTATTATTTGAAAAGATTCATA

AAAATGTTTGGAAACGAATGTATATCCCAGAAGAAATAAAATTTTTTATC

CTAAAATATATTACGCTGTTAAATAACTTGAGAGATTATATAATAAGTGT

ACATAATAATATGAAAAATGAGAAATATGATGAATGTTGGTTTTTATTTC

AACATTATTTTGAAAGATCGAGTGATGTAAGAAAAGAGATGGTTCATTTC

TTATTAGAAAGAAAGAGTCAAGAAAATTTAATATCTTTTAAAAGTAAATT

AAAAAGTAAAAAAGAAAAAATATTAACAATGGACATATTGAATTTTAGTA

AAGAACATATGCAATTAAAAACCATAGCTCATCTAAGAAAAGAAATAAAT

TATGAAAAACTTTCTAAGGATACCTTAAATAGAGATTATAATTTATTATT

-continued

```
ATATAAATATCAAGAATGTGTAAGTAAATTAAAAAGGGTAAAAAATTTAA
TGAAAGAAATAAATCAAAATGTATTTATAGAAAAATATGATGATATAAGT
AAAGAATTAGATAATTTTTCAGATGGATATAATGAACAAAATGAACAACA
TGTAATGGATCCTATTTTATTAAATAATAATAAAAACAAAAATAACAAAT
TGATAACTGAACATAATAATCCTATAATTAATAGGCTAACTAATTTTACA
CAAAACAGAGATTCAAAATATAAAAATAAAATAATGGATGATGTAAAACA
AAGAAAAATAAATAGTACAATGAATAATACAAATAAAAATGGTATTAATA
TTATATATAATCATTATGAAAATTTAAATAAACCAAACTATAATGATAAT
ATAAATAGATTAAATTCATATCATCAAAATATACATATTGCTAATTCAAT
TCATCCTAATAGAAATCAAAATAAAAGTTTTCTTACGAATCAAGCAAATA
GTACATATAGTGTTATGAAAAATTATATAAATTCAGATAAACCAAATTTA
AATGGAAAAAAGAGTGTAAGAAATATTTTTAATGAAATTGTCGATGAAAA
TGTAAATAAAACGTTTGTTCATAAAAGTGTATTTTTTTAA
```

The N-terminal part of the repetitive organellar protein, putative of *Plasmodium falciparum* 3D7 (GenBank: CZT98043.1) (SEQ ID NO: 6):

```
MVFTFKNKKKKKEASSDKVSKESFNEEDNENNEKREKSDSWYKKIIETKG
KSKTKYKNDNSLDDNINEDIINNNNNNNNDNNNDNNNDNNNDNNNDNNND
NNNENNNDNNNFNNYSDEISKNIIHKDNELENQLKDTLKSISSLSNKIVN
YESKIEELEKELKEVKDKNIDNNDYENKLKEKEDFVKQKIDMLNEKENLL
QEKELDINKREKKINEKEKNIIKKEETFHNIEKEYLEKNKERETISIEII
DIKKHLEKLKIEIKEKKEDLENLNKKLLSKENVLKELKGCVKEKNETINS
LNDNIIEKEKKYKLLEYELEEKNKQIDLLNKQEKEKEKEKEREKEKEREK
EKEKEYDTLIKELKDEKISILEKVHSIKVREMDIEKREHNFLHMEDQLKD
LKNSFVKNNNQLKVYKCEIKNLKTELEKKEKELKDIENVSKEEINKLINQ
LNEKEKQILAFNKNHKEEIHGLKEELKESVKITKIETQELQEMVDIKQKE
LDQLQEKYNAQIESISIELSKKEKEYNQYKNTYIEEINNLNEKLEETNKE
YTNLQNNYTNEINMLNNDIHMLNGNIKTMNTQISTLKNDVHLLNEQIDKL
```

The polynucleotide strand encoding for the at least nine consecutive amino acid moieties of SEQ ID NO: 3 can be any sequence suitable for this purpose. Preferably, it is a part of or the whole sequence according to the polypeptide sequence of the full length hypothetical protein PVNG_04523 of *Plasmodium vivax* North Korean (GenBank: KNA01322.1; GenBank: KQ235267.1_1:98732-104326 *Plasmodium vivax* North Korean chromosome Unknown supercont.1.94) (SEQ ID NO: 5):

```
ATGGTATTCAAATTTAAGAAGAAAAAGAAGGAAGAAAGCTCGGACAAGTT
AAGCAAGCAATCGCAAAACGATGAAGGAAATGCCAATGAGGAGGCAGAAA
AAAAAGACCACAAGAGTAACTCCTGGTACAAGAAAATAATCGACAATGCA
ATTATAACGAAGAGCAAGCATGACGATAAGGAGGAGCAGGAGGAGGAGAA
AAATGGCGAAGGAAATGACAGCAGGGCGATGGAAAGAAATAAAGATTATC
AATTGGAAGAGCAACTGAAGGAAACCCTAAGGTCAATCACGTCCTTGTCA
```

-continued

```
ACCAAAATTGTGAATTACGAAACGAAGATTGAAGATTTGGAGAAAGAGTT
AAAAATGGAAAAAGATAAACAAGTGGATAAGGCATACGAAAAGGAGTTGA
AGGAGAAGGAGAATTTTATTAAACAAAAAATTGGCATGCTAAATGAGAAG
GAAAATCTGCTAAATGAGAAGGAGCTGGACATAAATATGAGAGAAGAAAA
AATTAATGACAGAGAAATGTTCATTTCGAAAAAGGAAGACAAACTGAATG
ACATGCAGGAGCAGTACTTGGAAAAAAATAAAGAAAAAGAAAAACTCCAT
TTTGAAATTGCAGATATTAAGATTTCCTTAGAAAAGCTAAAGTACGAAGT
TAAAGATAAAAAGGACTGCCTAGAAAATGTCAGCAATAAGGTAATTTTGA
AGGAAAATACTCTGAGGGAGTTAAAAGAATTTATAAGGGAAAAAAACGAA
ATGATAGAATCGCTTAACGAGAAGATAACAGAGAAGGAGAAAATATATGA
GCAGTTAGGGAAGGACGTGGAGGAGAAGAGAAAGATCATCGAATTGCTAG
ACATGAAGGCAAATGAAAAGGAAAAATATTTCGAAGAAAAAATTAAAGAG
TTAGAAAAAGAACAAAATGCGCTTCTGCAAAAGTTAAATAATGTTAAGAT
GAGGGAGAAGGAAGTTGAGACGAGGGAAAATGACTTCCTGCACATGGAGG
ACGAGCTGAATGATCTTCGCAGTAGCTTCTCGAAGAATGATTGTCAGCTA
AAGATCTACAAATTGGAAATAAAAGATTTGAGCAGCGCCCTTGTGGAGAA
GGAGAGAGAAATATTGGACTTGAAAAATACCTACGACGGGGAAATCTGCT
CATTAAAGGATCAGATAAAGGAAAAGGAAAAGGAAATCGCCAAAGGTAGT
TCCTCCGGTGGTGACGTGGGTGCACAAGATGAGCCAGCTAGCGAAGTTGA
AAGTGAAGAAAAGGCGGACCCCAAAGAGGAAGGTGTGGAGAACAGCTTGA
CCGATTTGCTCAAAATGAAGGAAAGAGAGCTGCACGAAATGAAGGAAAAA
TACGCAAAGGAAATAGACACACTGAATAGCGAGCTGAATGAGAAAAAGAA
AGAATTCGTGGAGGCAAAAAATAGCCACATCAACCAGATAAACAACCTAA
ATGATGAAATTGAGGAGAGCGAAAGCAAAATGGCAGAACTGAAAAGTGGC
TACGAAATGGAGATCAAAAAACTGCGCAGCGAAATTAATGCAGTGCACGA
GGAGAAGTACCTCTTGAGCAACGAAAAACAAACACTCAGTGGAGAGATAG
ACAAGCTGAATGAAGAGAAGAAGTCCCTGGCCAGCGAGAAGGAGGAGCTA
CATAACAAAATAACCACGTTGAACAGCGAAATTGGGACGTTACATGTGGA
GAAACAGGCACTCACTGGAGAAATAAACACCTTAAACGATCTGATTCACA
CCCTGAAGAATGAAATCAGCTCGTCGGATAACCTGATTAGCAAATTGAAA
GAGCAAATGAACGCCATCAACGAAGAAAAGGAAGGAAAGGAAAAACTCAT
CACAGAGATAGAAAATAATTATAAAAATGAAATAAACGCGCTGAAGGAAA
AATTAAAAGACACGGACAATCAAGTGAGCATAAGTATTAGGGAAGAGATG
GACCACCTCAAATGCGTCCTTGGCGAAACGGAAAAGGAAAACAAACAGAT
GAAGGAGGACTACCACAAAAAGATAAAACAGTATGATGAAGAATTGCTAT
CGAAGCAGCAATATTTTGAAGAAGAATTAAATAACATACGCATCAAATCG
CACGAAAAGGAACAAATTTTGATTTTAAAAAATGACGAGTTGAAGGAGTC
GAAGCTAAAGACGGAGGAGAAGTACCTCAAGCTGTACGATGACAAAATGA
GTCTCCTCAGGAATATGTGCTCCAAAGTGGGGCTCCCCTACAGCGATGAA
GTTTCGGTGGAGGAGCTTCTCGAGCGGGTGGGCAACTACGTAAGTGGGAT
```

-continued

```
GGGTGAACCGGGGGGTGCGGCACACAGGGGGGAGCAAAGTGAGGAGCCGC
ATGAGGGGCAGTCGATTGTGGAGGAGACGAATGAACCCCTTTTGAGCGCC
CAAACGGCCGACAATGCTAATAGCCTAGAGGACAAGACAACCCTACAGGC
GCTACAGAAAGAACTGGAAAGTGTGCAAGAAGAGTACAGAGAAGAGGTAG
CCAAAATGAAGAGCTATTTGGCGATGAAGGAAAAAACGATAGAGGAGTCG
AACCACACAATCGCCGAGTTGACCGGAAAGATAAACAGCCTGAATGATAC
CATTTCGTTTTTTAAGGTTAACCACTCTGAGGAGAAAATTAATTCCTATA
TGGACGAAATTAACAGCTTGAGCTTGACGCTTAGCGAGCTGAAGGCTAAT
AATGAACAGGAGCAGTTGGAGAATCGAAACGAAATTGCCAGGCTGTCGGA
AGAGCTCAGCGGGTATAAGCGGCGTGCTGATGAGCAATGTAGAAAGAGGA
GCAGCGAGAAGGAGAGAAGCGAGTCCAAGAGGGGAGACACAAGAGGTGAC
TCCGAGAAGGAACAAATCTCCGAGTCGGACGTGGAAGGGGGGGGCAATTT
AAAATCCTTTTTACACTTTCCCCTTCGAAAAATAAAAGGGAAAAAAAGAA
AGGCCTCTAAAACTGAGAAGGAAATACAAACGGAGCTTAGGAGAAACGAG
CCAGAGAATGAACAGAGTGAGAAAAATGAGAAGGCGCCTAGAGGAGACAG
CCTGGAGGTGGACCAGTACAAAAAGGAATTGGAGGAAAAGGCGAAGATTA
TTGAGGACTTGAAGGACAAAATATGCACCCTGACGAATGAGGTTATGGAT
TTGAAGAATTTGAAGAACGAGCTGGCTGAGCGGGATAGCAGCTTGGCGAA
GGCGGGCGAGGAGGCGGAAAGGCAAAGAGAGCAGTTGGACACGCTGAGCG
CCCAACTGGGGGGTGCAAACGGAGAGGTGGAGAGACTCAGCGAAGAGGTG
GAGAGGCTCAACGAAGAGGTGGAGAAGCTGAAGGAGGGAGAGGCACAATC
GTGGGGGGAAGCGGAGAAGTGGAAAGGGGAAGCAGAGAAGTGGAAAGAAG
ACGCAGCGAAGTGGGAAGCGGACACAGTGAAATTGAAAGAGGACGCAGCG
AAATGGGAATCGGACGCAGTGAAGTGGGAATCGGACGCCGAGACGTGGAG
GAAAGAAGCGGAGGAACTGAGAAGCAGCGCGAATCAATTGAACGAAGAAT
TATGCTCGAAGGAAAATAACTACGTGTTGAAGCTGAACGAAAATGTGGGA
GTTATACAAAAAATGAAGGACTCAATTGATGCACGTGAAAAGGAGAAGGA
GAATTACGTTCGCGAGATAAACGATTTGAGAAACGAACTCGAAGGGTTGA
AATTGAAGCATGATGCGTTGAGTGAGACGTATAAGCAGTTGGAGGGGAAG
AGCAGCCCCCCCAGTGGAGATGACCCCCCTGGTGGAGATAACTACACCAG
TGAGGGAGAGAATAAATTAAGCATCCCAAATGAGAATTGCGAAATGGACC
AAGCGGAGGAAGCGAATGCCAACCCAGGTGTTCCCAAGAGCGAAATTGCC
ACCGAGGGGGGTGTCTCCTCATTGGCAGTGAACGATTACATAAGCGAAAT
AGCGCACCTGAAGGAAGAAATAAACAGACTAACCCTACTGTATAGCAACG
AACTGAACGAAAAAAACAGCTCTGATATTAGGACCAAAGAGCTGCTGAGC
CAGTTGAAGGAACTCGAAGTGAGGGATAAAGAAAATGAGGAAAAGATTGC
TGCGCTGAGCAAAATGAATGAGAAAATGAAAGCGAAAAATGAAAAGCTGA
AATCGGGGAAGTGGTTATCTAGGAAGGACCACGCGCCGAATGAAGAGGTA
GATATCGCAGGGGAGGAGCGTAAGAAGAAGGAGAAGGAGAAAGTGCCTCA
CCCGGATGTGAAAGAGGAGAGTCTGTCTTCAGAGCATGTGAACACACTGG
AAGGAAACACCTACCGCGTGATGAGAATAGTTGATGAAAGTAGCCCCGCG
```

-continued

```
GGAGGAGGCCAAATAATAGGGTCCTACTTGTACACCAAAAAGGTGGAAGA
TTTACACGCAGTAAATGGAGCAAATGTGGCAGATGCACAGCTGGCTGAGA
AAAACGCAATCACAGTTGTGTGTCTAATTCTAAGCGAAATCTTAAGCCTC
CTATTTTTGAACGATCAATTTGTTAACGCCTTTGAACGGATAAACAAAAG
TCTGTGGAAGCTTATGTACATGCCTGAAGAGATTAAAGCGCTGCTTCTGA
GGTATTTTTCCTTTATGAGTAAGCTCAGGGATTATGCCAAGGAGGTGCAC
GGGAGGGTGGAAAATGAGAGGTATGAAGACAGCCAAAGGCAGGACAACCA
ACGGTACGACGATTCGTGGTTACTTTTTCAAAACTATTTGGAGACGTCGA
GTAGTATCAAGAGGGACCTGGTGTGCTTCATTTTGGAAGAGAAGGAAAAT
GAACTAGCCGAGCTGGGCGAGCACTATGGTGGTGGAATGAGAAAGGGAGA
GGAAGTAATCGGGGGAGTACGCGGAGTGCGCGGGGGAAAAATCGCCGACA
TCATAAACCTTTCAAAGGACGAAATGAGATTGAAGACCATAGCACAGTTA
AGAAGAGACCTAGATTTTGAAAAGAAATCGAAAACATTGCTAAGCAGGGA
TTATCAGTTGTTACTTTATAAGTACCAGGAATGCGTGAGGAAGCTAAAGA
GGGTAAAAAATATGATAAGGCAGCTAAATCTGAACGACCATTCAAATAGA
GGCAGTTTCGCCTTAAACAGGGAGCTGGACAGGTGTTCCGAAGTGAGCAA
CGAGCGAGGTTTTAACGAGGAGGGGGTGATGAAGATTCGCACGGAAATT
ACAAAAACTGCATTCTGCAAGACAATAATAATAATAGCAGTGTAAATAAC
TATAATAGTAGTAACACCAAATTGGAGAGTCGGGAAAATGTTCTAATCAA
GGACCTAATCAATTTGAGGAGGGCGCAAAAGGTGAAGGGAAATAATTTGA
TCCACTGGGGCCGTCCCAGCATGATGATGGGGGGCAGGTGTCACCAAGAC
GCTTCCCATGTGGTAAGGGCGATGGTAAATGGACCCAAAATAAGCAGCCA
GAATATCTTCGCACACATGAACAGGCTGAGCAATGCGCCCAAAATTAGCG
ACCACTTGGATGACATGAAAAAAATGAAAAATATTTTTAACGAATTTGTT
GAAACCAGAGGGGACGTTACGTTTGTGCACAGGAGTCCCTTCTGCGAAAC
GTGA
```

As used herein, the term "isolated" may be understood in the broadest sense as any increase in purity. The isolated polypeptide strand P does not form part of a plasmodium or larger sized fragments of 100 or more nm thereof. Preferably, the isolated polypeptide strand P represents at least 5% by weight, more preferably at least 10% by weight, even more preferably at least 25% by weight, even more preferably at least 50% by weight, even more preferably at least 75% by weight, in particular at least 90% by weight of the whole polypeptide content of the vaccine V.

The terms "polypeptide", "protein" and "peptide" may be understood interchangeably throughout the invention in the broadest sense as any chemical entity mainly composed of amino acid residues and comprising at least nine amino acid residues consecutively linked with another via amide bonds. It will be understood that a protein in the sense of the present invention may or may not be subjected to one or more posttranslational modification(s) and/or be conjugated with one or more non-amino acid moiety/moieties. The termini of the protein may, optionally, be capped by any means known in the art, such as, e.g., amidation, acetylation, methylation, acylation. Posttranslational modifications are well-known in the art and may be but may not be limited to lipidation, phosphorylation, sulfatation, glycosylation, truncation, oxidation, reduction, decarboxylation, acetylation, amidation, deamidation, disulfide bond formation, amino acid addition, cofactor addition (e.g., biotinylation, heme addition, eicosanoid addition, steroid addition) and complexation of metal ions, non-metal ions, peptides or small molecules and addition of iron-sulphide clusters. Moreover, optionally, co-factors, in particular cyclic guanidinium monophosphate (cGMP), but optionally also such as, e.g., ATP, ADP, $NAD^+$, $NADH+H^+$, $NADP^+$, $NADPH+H^+$, metal ions, anions, lipids, etc. may be bound to the protein, irrespective on the biological influence of these co-factors. In the context of Glu-plasminogen in particular glycosylation may play a role. In a particularly preferred embodiment, the isolated polypeptide strand P does not bear posttranslational modifications, i.e., consists of the plain polypeptide sequence consisting of consecutive amino acid moieties.

As used herein, the terms "pharmaceutically acceptable carrier", "pharmaceutically acceptable excipient", "carrier" and "excipient" may be understood interchangeably in the broadest sense as any substance that may support the pharmacological acceptance of the vaccine V. A pharmaceutically acceptable carrier may exemplarily be selected from the list consisting of an aqueous buffer, saline, water, dimethyl sulfoxide (DMSO), ethanol, vegetable oil, paraffin oil or combinations of two or more thereof. Furthermore, the pharmaceutically acceptable carrier may optionally contain one or more detergent(s), one or more foaming agent(s) (e.g., sodium lauryl sulfate (SLS), sodium doceyl sulfate (SDS)), one or more coloring agent(s) (e.g., food coloring), one or more vitamin(s), one or more salt(s) (e.g., sodium, potassium, calcium, zinc salts), one or more humectant(s) (e.g., sorbitol, glycerol, mannitol, propylenglycol, polydextrose), one or more enzyme(s), one or more preserving agent(s) (e.g., benzoic acid, methylparabene, one or more antioxidant(s), one or more herbal and plant extract(s), one or more stabilizing agent(s), one or more chelating agents (e.g., ethylenediaminetetraacetic acid (EDTA), and/or one or more uptake mediator(s) (e.g., polyethylene imine (PEI), a cell-penetrating peptide (CPP), a protein transduction domain (PTD), an antimicrobial peptide, etc.). In addition, the excipient of the vaccine V may or may not comprise one or more adjuvants. An excipient may be an adjuvant such as, e.g., alum.

As used herein, the term "adjuvant" may be understood in the broadest sense as any that supports immunologic stimulation. It may be a solution or emulsion of antigen emulsified in mineral oil and used as an immunopotentiator (booster). An adjuvant may also comprise muramyl peptide (MDP). An adjuvant typically significantly enhances the immune response to the isolated polypeptide strand P. Typically, immune response is at least two-fold higher compared to a comparable vaccine lacking the adjuvant.

In a preferred embodiment, the vaccine V comprises an adjuvant supporting immunologic stimulation. In a preferred embodiment, the excipient of the vaccine V comprises at least one adjuvant, such as, e.g., alum. In a preferred embodiment, the vaccine V comprises at least one adjuvant supporting immunologic stimulation selected from the group consisting of alum and an immunostimulatory peptide, and optionally one or more further pharmaceutically acceptable carriers. The combination of an adjuvant such as alum and one or more immunostimulatory peptides may also be designated as composite adjuvant. In a preferred embodiment, an adjuvant in the sense of the present invention is a composite adjuvant. In a preferred embodiment, such composite adjuvant includes alum and one or more further immunostimulatory agents. In a preferred embodiment, such composite adjuvant includes alum and one or more immunostimulatory peptides (e.g., muramyl peptide (MDP) and/or monophosphoryl lipid A (MPL), a modified bacterial coat molecule). In a preferred embodiment, an immunostimulatory peptide is selected from the group consisting of muramyl peptide (MDP) and/or monophosphoryl lipid A (MPL).

It is known that alum bears several technical disadvantages such as rather unsatisfactory enlisting of cytotoxic T cells that may be helpful for fighting malaria (Leslie, 2013). It will be, thus, understood that alum may be replaced by another adjuvant that at least partly overcomes these drawbacks. Such replacement of an adjuvant would not alter the sense of the present invention.

As experimentally evidenced, peptides derived from SEQ ID NO: 2 or SEQ ID NO: 3 are particularly strong immunogens. Therefore, in some preferred embodiments, an adjuvant such as, e.g., muramyl peptide (MDP), may also be omitted. This may avoid undesired side effects and/or may be more cost-efficient. Accordingly, in another preferred embodiment, the vaccine V does (essentially) not comprise (thus, is (essentially) free of) muramyl peptide (MDP).

In an alternative preferred embodiment, the vaccine V does (essentially) not comprise (thus, is (essentially) free of) an adjuvant.

In a preferred embodiment, the vaccine V comprises at least one isolated polypeptide strand P comprising or consisting of at least nine consecutive amino acid moieties of the repetitive organellar protein, putative of *Plasmodium falciparum* 3D7 (SEQ ID NO: 2) or the hypothetical protein PVNG_04523 of *Plasmodium vivax* North Korean (SEQ ID NO: 3) or a polynucleotide strand encoding for said polypeptide strand P.

In a preferred embodiment, the vaccine V comprises or consists of:

(A) at least one isolated polypeptide strand P comprising or consisting of at least nine consecutive amino acid moieties of SEQ ID NO: 2; and (B) at least one pharmaceutically acceptable carrier or excipient.

In another preferred embodiment, the vaccine V comprises or consists of:

(A) at least one isolated polypeptide strand P comprising or consisting of at least nine consecutive amino acid moieties of SEQ ID NO: 3; and (B) at least one pharmaceutically acceptable carrier or excipient.

In another preferred embodiment, the vaccine V comprises or consists of:

(A) at least one polynucleotide strand encoding for a polypeptide strand P comprising or consisting of at least nine consecutive amino acid moieties of SEQ ID NO: 2; and (B) at least one pharmaceutically acceptable carrier or excipient.

In another preferred embodiment, the vaccine V comprises or consists of:

(A) at least one polynucleotide strand encoding for a polypeptide strand P comprising or consisting of at least nine consecutive amino acid moieties of SEQ ID NO: 3; and (B) at least one pharmaceutically acceptable carrier or excipient.

Preferably, the isolated polypeptide strand P is not too short in order to provide various antigens and to improve antigenicity. In a preferred embodiment, the isolated polypeptide strand P comprises or consists of at least 10, at least 15, at least 20, at least 50 or at least 100 consecutive amino acid moieties of SEQ ID NO: 2 and/or SEQ ID NO: 3.

In a preferred embodiment, the polypeptide strand P comprises or consists of from 10 to 250, from 10 to 100, from 15 to 75, from 20 to 50, or from 25 to 45 consecutive amino acid moieties of SEQ ID NO: 2. In another preferred embodiment, the polypeptide strand P comprises or consists of from 10 to 250, of from 11 to 100, from 15 to 75, from 20 to 50, or from 25 to 45 consecutive amino acid moieties of SEQ ID NO: 3. In another preferred embodiment, the polypeptide strand P comprises or consists of from 10 to 250, of from 11 to 100, from 15 to 75, from 20 to 50, or from 25 to 45 consecutive amino acid moieties of SEQ ID NO: 6.

In a preferred embodiment, the isolated polypeptide strand P comprises (or consists of) at least 100, at least 200, at least 500, at least 1000, or at least 1800 consecutive amino acids having at least 80%, more preferably at least 90%, even more preferably at least 95%, more preferably at least 98% or homology to or even sequence identity with the polypeptide sequence of SEQ ID NO: 2 and/or SEQ ID NO: 3.

In a preferred embodiment, the isolated polypeptide strand P comprises or consists of an amino acid sequence having at least 80%, more preferably at least 90%, even more preferably at least 95%, more preferably at least 98% or homology to or even sequence identity with the polypeptide sequence of SEQ ID NO: 2.

In another preferred embodiment, the isolated polypeptide strand P comprises or consists of an amino acid sequence having at least 80%, more preferably at least 90%, even more preferably at least 95%, more preferably at least 98% or homology to or even sequence identity with the polypeptide sequence of SEQ ID NO: 3.

In a highly preferred embodiment, the isolated polypeptide strand P consists of an amino acid sequence having the polypeptide sequence of SEQ ID NO: 2. In a highly preferred embodiment, the isolated polypeptide strand P consists of an amino acid sequence having the polypeptide sequence of SEQ ID NO: 2 obtained from heterologous expression. In a highly preferred embodiment, the isolated polypeptide strand P consists of an amino acid sequence having the polypeptide sequence of SEQ ID NO: 2 obtained from heterologous expression in a bacterium, in particular in *Escherichia coli* (*E. coli*).

In a highly preferred embodiment, the isolated polypeptide strand P consists of an amino acid sequence having the polypeptide sequence of SEQ ID NO: 3. In a highly preferred embodiment, the isolated polypeptide strand P consists of an amino acid sequence having the polypeptide sequence of SEQ ID NO: 3 obtained from heterologous expression. In a highly preferred embodiment, the isolated polypeptide strand P consists of an amino acid sequence having the polypeptide sequence of SEQ ID NO: 3 obtained from heterologous expression in a bacterium, in particular in *Escherichia coli* (*E. coli*).

In a highly preferred embodiment, the vaccine V comprises two isolated polypeptide strands P consisting of amino acid sequence having the polypeptide sequences of SEQ ID NO: 2 and SEQ ID NO: 3. In a highly preferred embodiment, the vaccine V comprises two isolated polypeptide strands P consisting of amino acid sequence having the polypeptide sequences of SEQ ID NO: 2 and SEQ ID NO: 3 each obtained from heterologous expression, preferably obtained from heterologous expression in a bacterium, in particular in *Escherichia coli* (*E. coli*).

In another preferred embodiment, the isolated polypeptide strand P comprises or consists of an amino acid sequence having at least 80%, more preferably at least 90%, even more preferably at least 95%, more preferably at least 98% or homology to or even sequence identity with the polypeptide sequence of SEQ ID NO: 6.

In an alternative preferred embodiment, the isolated polypeptide strand P comprises or consists of an amino acid sequence having at least 80%, more preferably at least 90%, even more preferably at least 95%, more preferably at least 98% or homology to or even sequence identity with the polypeptide sequence of SEQ ID NO: 1.

In an alternative preferred embodiment, the isolated polypeptide strand P comprises or consists of an amino acid sequence having amino acids of positions 1283-1516 (234 amino acids) of SEQ ID NO: 1.

In a preferred embodiment, the nucleotide sequence usable as antigen encodes for such polypeptide sequence of SEQ ID NO: 2 and/or SEQ ID NO: 3. In a preferred embodiment, the nucleotide sequence usable as antigen (including an indirect antigen encoding the polypeptide strand P (that may serve as antigen)) bears at least 300, at least 600, at least 1500, at least 3000, or at least 5000 consecutive nucleotides having at least 80%, more preferably at least 90%, even more preferably at least 95%, more preferably at least 98% or homology to or even sequence identity with the sequence of SEQ ID NO: 4 and/or SEQ ID NO: 5. As indicated herein, such sequence may optionally be embedded in a larger polynucleotide sequence. In a preferred embodiment, the nucleotide sequence encodes for the polypeptide strand P (that may serve as antigen).

In a preferred embodiment, the nucleotide sequence encoding the polypeptide strand P bears at least 300, at least 600, at least 1500, at least 3000, or at least 5000 consecutive nucleotides having at least 80%, more preferably at least 90%, even more preferably at least 95%, more preferably at least 98% or homology to or even sequence identity with the sequence of SEQ ID NO: 4. In a preferred embodiment, the nucleotide sequence encoding the polypeptide strand P bears at least 300, at least 600, at least 1500, at least 3000, or at least 5000 consecutive nucleotides having at least 80%, more preferably at least 90%, even more preferably at least 95%, more preferably at least 98% or homology to or even sequence identity with the sequence of SEQ ID NO: 5.

In a preferred embodiment, the at least one isolated polypeptide strand P consists of or comprises a peptide strand having at least 80% sequence homology to sequence SEQ ID NO: 2 or SEQ ID NO: 3 obtained from heterologous expression. In a preferred embodiment, the at least one isolated polypeptide strand P consists of or comprises a peptide strand having at least 90% sequence homology to sequence SEQ ID NO: 2 or SEQ ID NO: 3 obtained from heterologous expression. In a preferred embodiment, the at least one isolated polypeptide strand P consists of or comprises a peptide strand having at least 95% sequence homology to sequence SEQ ID NO: 2 or SEQ ID NO: 3 obtained from heterologous expression. In a preferred embodiment, the at least one isolated polypeptide strand P consists of or comprises a peptide strand having at least 98% sequence homology to sequence SEQ ID NO: 2 or SEQ ID NO: 3 obtained from heterologous expression. In a preferred embodiment, the at least one isolated polypeptide strand P consists of or comprises a peptide strand having a sequence SEQ ID NO: 2 or SEQ ID NO: 3 obtained from heterologous expression.

The person skilled in the art will notice that the isolated polypeptide strand P as used in a vaccine V of the present invention may also form part of a fusion protein, a multi-antigen vaccine, or a viral vector.

In a highly preferred embodiment, the isolated polypeptide strand P comprises (essentially) the whole polypeptide sequence of SEQ ID NO: 2 and/or SEQ ID NO: 3. In a highly preferred embodiment, the nucleotide sequence usable as antigen comprises (essentially) the whole polypeptide sequence of SEQ ID NO: 4 and/or SEQ ID NO: 5.

The isolated polypeptide strand P may be obtained by any means. In order to obtain a rather pure and polypeptide one effective mean is to employ an effective (over)expression technique. The person skilled in the art is aware of numerous methods suitable for this purpose. In a preferred embodiment, the isolated polypeptide strand P is obtained from heterologous expression.

As used herein, "heterologous expression" may be understood in the broadest sense as expression of a gene encoding for the polypeptide according to SEQ ID NO: 2 and/or SEQ ID NO: 3 or fragment thereof in a host organism, which does not naturally have this gene or gene fragment. Insertion of the gene in the heterologous host may be performed by recombinant DNA technology which is well-known to the person skilled in the art. For this purpose, the gene may be inserted to the host, wherein it may be integrated into the host DNA causing permanent expression, or may not be integrated causing transient expression of this gene.

In a more preferred embodiment, the isolated polypeptide strand P is obtained from heterologous expression in bacterial or eukaryotic cells. In a highly preferred embodiment, the isolated polypeptide strand P is obtained from heterologous expression in bacterial cells such as *E. coli*. Such host organism comprising the gene encoding for the polypeptide strand P may also be designated as "expression system". An advantage of such heterologous expression is that high amounts of the peptide are obtainable in good purity. In contrast to peptide synthesis, toxic agents can be avoided. On the other hand, in particular when expressed in bacteria, the peptides are typically not glycosylated.

In a preferred embodiment, the vaccine V of the present invention comprises or consists of:

(A) at least one isolated polypeptide strand P comprising or consisting of a peptide strand having at least 80% sequence homology to a sequence SEQ ID NO: 2 or SEQ ID NO: 3 obtained from heterologous expression; and (B) at least one adjuvant supporting immunologic stimulation and optionally one or more further pharmaceutically acceptable carriers.

In view of the further preferred embodiments described herein, it will be understood that the isolated polypeptide strand P may also have a higher homology and/or any of the other properties described herein. Further, in view of the further preferred embodiments described herein, the pharmaceutically acceptable carrier and/or the adjuvant may bear more specific properties.

In a preferred embodiment, the vaccine V comprises or consists of:

(A) at least one isolated polypeptide strand P comprising or consisting of a peptide strand of sequence SEQ ID NO: 2 or SEQ ID NO: 3 obtained from heterologous expression; and (B) at least one adjuvant supporting immunologic stimulation selected from the group consisting of alum and an immunostimulatory peptide, and optionally one or more further pharmaceutically acceptable carriers.

In a preferred embodiment, the vaccine V comprises or consists of:

(A) at least one isolated polypeptide strand P comprising or consisting of a peptide strand of sequence SEQ ID NO: 2 or SEQ ID NO: 3 obtained from heterologous expression in bacteria; and (B) a composite adjuvant supporting immunologic stimulation comprising alum and at least one immunostimulatory peptide, and optionally one or more further pharmaceutically acceptable carriers.

Alternatively, the polypeptide strand P may also be isolated from *Plasmodium falciparum* or *Plasmodium vivax*. This may optionally be performed by chromatographic means.

In a preferred embodiment, the at least one isolated polypeptide strand P comprises or consists of at least nine consecutive amino acid moieties of a sequence having at least 80% sequence homology to a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

The sequences of SEQ ID Nos 7 to 15 are the following:

```
                                    (SEQ ID NO: 7)
KQEKEKEKEKEREKEKEREKEKEKEY

                                    (SEQ ID NO: 8)
KNLKTELEKKEKELKDIENVSKEEINKL

                                    (SEQ ID NO: 9)
SKKEKEYNQYKNTYIEEINNLNEKLEETNKEYTNLQNNYTN

                                   (SEQ ID NO: 10)
KEEYEDKMNTLNEQNEDKMNSLKEEYENK

                                   (SEQ ID NO: 11)
KGLKKEVEEKEHKRHSSFNILKSKEKFFKNSIEDKSHELKKKHE

                                   (SEQ ID NO: 12)
KDKSKEKIKDKENQINVEKNEEKDLKKKDD

                                   (SEQ ID NO: 13)
EDEKKRNLNEINNLKKKNEDMCIKYNEMN

                                   (SEQ ID NO: 14)
KTNKENEEKIINLTSQYSDAYKKKSDES

                                   (SEQ ID NO: 15)
SNNNIRTNEYKYEEMFDTNIEEKNG

                                   (SEQ ID NO: 16)
GNISNKNENNNKKNNTCDGYDEKVT
```

These sequences are described in more detail in the experimental part below.

In a preferred embodiment, the at least one isolated polypeptide strand P comprises or consists of at least nine consecutive amino acid moieties of a sequence having at least 90% sequence homology to a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P comprises or consists of at least nine consecutive amino acid moieties of a sequence having at least 95% sequence homology to a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P comprises or consists of at least nine consecutive amino acid moieties of a sequence having at least 98% sequence homology to a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P comprises or consists of at least nine consecutive amino acid moieties of a sequence having a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the above peptides may also be at least ten consecutive amino acid moieties, at least 15 consecutive amino acid moieties, at least 20 consecutive amino acid moieties, at least 25 consecutive amino acid moieties, at least 50 consecutive amino acid moieties, or at least 100 consecutive amino acid moieties as far as the respective sequence provided above is long enough.

In another preferred embodiment, the at least one isolated polypeptide strand P comprises or consists of a sequence having at least 80% sequence homology to a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P comprises or consists of a sequence having at least 90% sequence homology to a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P comprises or consists of a sequence having at least 95% sequence homology to a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P comprises or consists of a sequence having at least 98% sequence homology to a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P comprises or consists of a sequence having a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P is a truncated version of SEQ ID NO: 2 comprising at least one peptide sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P is a truncated version of SEQ ID NO: 2 comprising at least two peptide sequences selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In a preferred embodiment, the at least one isolated polypeptide strand P is a truncated version of SEQ ID NO: 2 comprising at least sequences of SEQ ID NO: 7 and 8, SEQ ID NO: 7 and 9, SEQ ID NO: 7 and 10, SEQ ID NO: 7 and 11, SEQ ID NO: 7 and 12, SEQ ID NO: 7 and 13, SEQ ID NO: 7 and 14, SEQ ID NO: 7 and 15, SEQ ID NO: 7 and 16, SEQ ID NO: 8 and 9, SEQ ID NO: 8 and 10, SEQ ID NO: 8 and 11, SEQ ID NO: 8 and 12, SEQ ID NO: 8 and 13, SEQ ID NO: 8 and 14, SEQ ID NO: 8 and 15, SEQ ID NO: 8 and 16, SEQ ID NO: 9 and 10, SEQ ID NO: 9 and 11, SEQ ID NO: 9 and 12, SEQ ID NO: 9 and 13, SEQ ID NO: 9 and 14, SEQ ID NO: 9 and 15, SEQ ID NO: 9 and 16, SEQ ID NO: 10 and 11, SEQ ID NO: 10 and 12, SEQ ID NO: 10 and 13, SEQ ID NO: 10 and 14, SEQ ID NO: 10 and 15, SEQ ID NO: 10 and 16, SEQ ID NO: 11 and 12, SEQ ID NO: 11 and 13, SEQ ID NO: 11 and 14, SEQ ID NO: 11 and 15, SEQ ID NO: 11 and 16, SEQ ID NO: 12 and 13, SEQ ID NO: 12 and 14, SEQ ID NO: 12 and 15, SEQ ID NO: 12 and 16, SEQ ID NO: 13 and 14, SEQ ID NO: 13 and 15, SEQ ID NO: 13 and 16, SEQ ID NO: 14 and 15, SEQ ID NO: 14 and 16, or SEQ ID NO: 15 and 16.

As used throughout the present invention, the term "truncated version of SEQ ID NO: 2" means a peptide comprising or consisting of a fraction of SEQ ID NO: 2 truncated by at least one amino acid moiety in length. In other words, in a t truncated version of SEQ ID NO: 2, at least one amino acid moiety is missing. Even if the truncated peptide sequence is extended by one or more amino acid moieties, these are not the same as those of SEQ ID NO: 2.

In a preferred embodiment, a truncated version of SEQ ID NO: 2 comprises or consists of a fraction of SEQ ID NO: 2 truncated by at least two, at least three, at least five, at least ten, at least 20, at least 50, at least 75, at least 100, at least 200, at least 500, or at least 1000 amino acid moieties in length. In a preferred embodiment, the polypeptide strand P which is a truncated version of SEQ ID NO: 2 comprises or consists of from 32 to 1900, from 40 to 1800, from 50 to 1700, from 60 to 1600, from 70 to 1500, from 80 to 1400, from 90 to 1300, from 100 to 1200, from 200 to 1100, from 300 to 1000 amino acid moieties in length.

In a preferred embodiment, a truncated version of SEQ ID NO: 2 comprises or consists of a fraction of SEQ ID NO: 2 truncated by at least 100 amino acid moieties in length.

In a preferred embodiment, the at least one isolated polypeptide strand P is a truncated version of SEQ ID NO: 2 comprising or consisting of a fraction of SEQ ID NO: 2 truncated by at least 100 amino acid moieties in length and comprising at least two peptide sequences selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P is a truncated version of SEQ ID NO:

2 comprising or consisting of a fraction of SEQ ID NO: 2 truncated by at least 100 amino acid moieties in length and comprising all of the peptide sequences SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P is a truncated version of SEQ ID NO: 2 comprising at least three peptide sequences selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P is a truncated version of SEQ ID NO: 2 comprising at least four peptide sequences selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In a preferred embodiment, the at least one isolated polypeptide strand P is a truncated version of SEQ ID NO: 2 comprising at least five peptide sequences selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. In a preferred embodiment, the at least one isolated polypeptide strand P is a truncated version of SEQ ID NO: 2 comprising at least six, at least seven, at least eight, or least nine, peptide sequences selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one isolated polypeptide strand P is a truncated version of SEQ ID NO: 2 comprising all of the peptide sequences SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

As indicated herein, the polypeptide strand P may also be obtained by means of heterologous expression. It has been surprisingly found that also polypeptide strands P which were obtained from heterologous expression in bacteria led to a remarkable effectivity. Therefore, also non-glycosylated peptide strands P showed activity as experimentally evidenced.

Accordingly, in a preferred embodiment, the polypeptide strand P does not comprise (i.e., is (essentially) free of glycosylation.

Alternatively, it will be understood that glycosylated peptides are, however, also suitable. Therefore, in an alternative preferred embodiment, the polypeptide strand P comprises one or more glycosylated sides.

In a preferred embodiment, the polypeptide strand P comprises or consists of an easily assessable epitope. Accordingly, it preferably bears a sequence as laid out above. This is evidenced further by bioinformatic means as laid out in the experimental section below. In a preferred embodiment, the polypeptide strand P is not a hardly assessable sequence.

Thus, in a preferred embodiment, in particular when the polypeptide strand P is not the full-length protein (of any of SEQ ID NOs: 2 or 3), the polypeptide strand P is not and/or comprises no peptide strand that has a length of nine or more consecutive amino acid moieties of at least 80% homology of any of SEQ ID NOs: 17-24. In a preferred embodiment, in particular when the polypeptide strand P is not the full-length protein (of any of SEQ ID NOs: 2 or 3), the polypeptide strand P is not and/or comprises no peptide strand that has a length of nine or more consecutive amino acid moieties of at least 80% homology of any of SEQ ID NOs: 17-21.

In a preferred embodiment, in particular when the polypeptide strand P is not the full-length protein (of any of SEQ ID NOs: 2 or 3), the polypeptide strand P is not and/or comprises no peptide strand that has a length of nine or more consecutive amino acid moieties of at least 98% homology of any of SEQ ID NOs: 17-21. In a preferred embodiment, in particular when the polypeptide strand P is not the full-length protein (of any of SEQ ID NOs: 2 or 3), the polypeptide strand P is not and/or comprises no peptide strand that has a length of nine or more consecutive amino acid moieties of at least 98% homology of any of SEQ ID NOs: 17-24. In a preferred embodiment, in particular when the polypeptide strand P is not the full-length protein (of any of SEQ ID NOs: 2 or 3), the polypeptide strand P is not and/or comprises no peptide strand that has a length of nine or more consecutive amino acid moieties of any of SEQ ID NOs: 17-21. In a preferred embodiment, in particular when the polypeptide strand P is not the full-length protein (of any of SEQ ID NOs: 2 or 3), the polypeptide strand P is not and/or comprises no peptide strand that has a length of nine or more consecutive amino acid moieties of any of SEQ ID NOs: 17-24.

In a preferred embodiment, the polypeptide strand P is not a sequence having at least 80% sequence homology to a peptide sequence selected from the group consisting of one or more of SEQ ID NOs: 17-24. In a preferred embodiment, the polypeptide strand P is not a peptide strand of a sequence having at least 80% sequence homology to all of SEQ ID NOs: 17-21. In a preferred embodiment, the polypeptide strand P is not a peptide strand of a sequence having at least 80% sequence homology to all of SEQ ID NOs: 17-24.

SEQ ID NOs: 17-24 refer to the following sequences:

```
                                        (SEQ ID NO: 17)
IKTMNTQISTLKNDVHLLNEQDKLNNEKGTLNSKISELNVQI

MDL

                                        (SEQ ID NO: 18)
LLSKDKEIEEKNKKIKELNNDIKKL

                                        (SEQ ID NO: 19)
ICSLTTEVMELNNKKNELIEENNKLNLVDQGKKKLKKDVEK

QKKEIEKL

                                        (SEQ ID NO: 20)
VDKIEEHILDYDEEINKSRSNLFQLKNEICSLTTEVMELNNKK

NELIEENNKLNLVDQGKKKLKKDVEKQKKEIEKL

                                        (SEQ ID NO: 21)
LDENEDNIKKMKSKIDDMEKEIKYR

                                        (SEQ ID NO: 22)
TISSLSNKIVNYESKIEELEKELKEVK

                                        (SEQ ID NO: 23)
IIDIKKHLEKLKIEIKEKKEDLENL

                                        (SEQ ID NO: 24)
IKTMNTQISTLKNDVHLLNEQDKLNNEKGTLNSKISEL
```

In a preferred embodiment, the polypeptide strand P does not have a sequence of SEQ ID NOs: 17-21. In a preferred embodiment, the polypeptide strand P does not have a sequence of SEQ ID NOs: 17-24.

A vaccine V based on a polynucleotide strand encoding for the polypeptide strand P may be any kind of polynucleotide. In a preferred embodiment, the polynucleotide strand encoding for said polypeptide strand P is double or single stranded DNA or double or single stranded RNA, or an analogue of double or single stranded DNA or double or single stranded RNA.

Such nucleotide analogue may exemplarily comprise or even consist of nucleotide analogues such as, e.g., peptide nucleic acid (PNA), Morpholino and locked nucleic acid (LNA), as well as glycol nucleic acid (GNA) and threose nucleic acid (TNA).

In a preferred embodiment, the polynucleotide strand encoding for said polypeptide strand P is a plasmid.

In a preferred embodiment, the at least one polynucleotide strand encoding for the polypeptide strand P is a polynucleotide strand encoding for a sequence having at least 80% sequence homology, at least 90% sequence homology, at least 95% sequence homology, or at least 98% sequence homology to a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In a preferred embodiment, the at least one polynucleotide strand encoding for the polypeptide strand P is a polynucleotide strand encoding for a sequence having a peptide sequence selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

As indicated above, it will be understood that the vaccine V of the present invention is well suitible for preventing malaria in a patient.

Accordingly, as indicated above, a further aspect of the present invention relates to the vaccine V of the present invention for use in a method for preventing malaria in a patient.

In other words, the present invention relates to a method for preventing malaria in a patient, wherein a sufficient amount of the vaccine V is administered to said patient. This method may be understood as active immunization.

As throughout the present invention, malaria is preferably malaria caused by *Plasmodium falciparum* or *Plasmodium vivax*. The person skilled in eth art will notice that the respective vaccine V (comprising at least one isolated polypeptides P or at least one nucleotide encoding for such) will provide at least partly protection against *Plasmodia* of the respective type. A vaccine V comprising at least one isolated polypeptides P of a sequence homolog to *Plasmodium falciparum* or at least one nucleotide encoding for such will particularly prevent the patient from malaria caused by *Plasmodium falciparum.*

A vaccine V comprising at least one isolated polypeptides P of a sequence homolog to *Plasmodium vivax* or at least one nucleotide encoding for such will particularly prevent the patient from malaria caused by *Plasmodium vivax.*

As used herein, "preventing" does not necessarily means that the disease is completely prohibited, but means, in the broadest sense, that the symptoms of malaria are diminish, when the patient is exposed to the respective plasmodia (e.g., *Plasmodium falciparum* and/or *Plasmodium vivax* (and/or, regarding rodents, *Plasmodium chabaudi*)). The effect of diminishing symptoms is the reduction in comparison to a comparable patient exposed to a comparable amount of the respective plasmodia (e.g., *Plasmodium falciparum* and/or *Plasmodium vivax* (and/or, regarding rodents, *Plasmodium chabaudi*)) without administration of the vaccine V.

As used herein, a "sufficient amount" may be understood in the broadest sense as an amount that is suitible to provoke an immune response against plasmodia. Preferably, a sufficient amount vaccine V is suitible to diminish the quantity of the respective plasmodia (e.g., *Plasmodium falciparum* and/or *Plasmodium vivax* (and/or, regarding rodents, *Plasmodium chabaudi*)) when the patient is exposed to plasmodia.

In a preferred embodiment, at each administration, the patient is administered with an amount of an isolated polypeptide strand P in the range of from 0.1 μg/kg to 1 g/kg, of from 1 μg/kg to 100 mg/kg, of from 5 μg/kg to 50 mg/kg, of from 10 μg/kg to 25 mg/kg, of from 25 μg/kg to 20 mg/kg, of from 50 μg/kg to 10 mg/kg, or of from 100 μg/kg to 5 mg/kg.

In a preferred embodiment, the patient is administered with a sufficient amount of the vaccine V to diminish the symptoms of malaria or even to prohibit the outbreak of malaria completely. In other words, this may be sufficient to confer protection.

The patient may be administered with the vaccine V of the present invention once, twice, three times of more often. The patient may also be administered on a regular basis (e.g., once per month, once per two months, one per three months, once per half a year, once per year or once every five years).

In a preferred embodiment, the patient is administered only once. This may already be sufficient for developing an immune response to diminish the quantity of the respective plasmodia (e.g., *Plasmodium falciparum* and/or *Plasmodium vivax* (and/or, regarding rodents, *Plasmodium chabaudi*)) when the patient is exposed to plasmodia. This may diminish the symptoms of malaria or even to prohibit the outbreak of malaria completely. In other words, this may be sufficient to confer protection.

In a preferred embodiment, the vaccine V is administered at least once to the patient before exposure to the respective plasmodia (e.g., *Plasmodium falciparum* and/or *Plasmodium vivax* (and/or, regarding rodents, *Plasmodium chabaudi*)). In another preferred embodiment, the vaccine V is administered to the patient during and/or after exposure to the respective plasmodia. In a preferred embodiment, the vaccine V is administered at least once to the patient before exposure to the respective plasmodia and during and/or after exposure to the respective plasmodia As indicated above, the vaccine V of the present invention may be very well be used for generating antibodies binding to *Plasmodium falciparum* or *Plasmodium vivax*. As used in the context of antibodies, terms like "binding to", "directed to", "targeted" or the like may be understood interchangeably in the broadest sense as interacting selectively and non-covalently with a binding affinity of a dissociation constant (Kd) of 1000 nM or less. Accordingly, the present invention also refers to the generation of antibodies by means of a vaccine V of the present invention. In other words, the present invention also refers to the use of a vaccine V of the present invention for preparing an antibody AB binding to *Plasmodium falciparum* or *Plasmodium vivax*, in particular, binding to the repetitive organellar protein, putative of *Plasmodium falciparum* 3D7 or the hypothetical protein PVNG_04523 of *Plasmodium vivax* North Korean.

Accordingly, a further aspect of the present invention refers a method for preparing an antibody AB, binding to *Plasmodium falciparum* or *Plasmodium vivax* comprising the following steps:

(i) providing:

(a) a vaccine V according to the present invention, and (b) an organism O suitible for generating antibodies;

(ii) administering the organism O with the vaccine V;

(iii) waiting until the subjected organism of step (ii) shows an immune response against the antigens of the vaccine V;

(iv) obtaining antibody-generating cells C of the organism O of step (iii);

(v) optionally hybridizing the antibody-generating cells of step (iv) with myeloma cells obtaining immortalized antibody-generating cells C1;

(vi) optionally isolating the nucleotide encoding for the antibody AB of interest and transfer it to another antibody-generating cell type C2 suitible for expressing the antibody AB;

(vii) cultivating the antibody-generating cells C, C1 or C2 of any of steps (iv) to (vi) under conditions enabling the production of the antibody AB; and (viii) isolating the antibody from step (vii).

In the context of such method, the organism O may be any organism suitible for generating antibodies. Preferably, the organism is a (typically non-human) mammalian. Exemplarily, the organism O may be selected from the group consisting of a mouse, a rat, a rabbit, a goat, a hamster, a donkey, a cow, a pig, or a camel.

Preferably, administration of step (ii) is systemic administration (e.g., intravenously (i.v.), intraarterially (i.a.), intraperitoneally (i.p.), intramusculary (i.m.), subcutaneously (s.c.), transdermally, nasally). Alternatively, administration may also be local administration (e.g., intrathecally or intravitreally). Preferably, administration is systemic administration, in particular intravenous injection.

The waiting time depends on the vaccine V, the species of the organism O and the like. Typically it will take several days up to several weeks until an immune response is obtained. Exemplarily, the waiting time may be between 1 day and twenty weeks, preferably between 2 days and ten weeks, more preferably between 3 days and five weeks, exemplarily between 4 days and three weeks. During this time, the animals are kept under suitable conditions for maintain health for this species.

Obtaining antibody-generating cells C of the organism O of step (iii) may be performed by any means known for this purpose in the art. Optionally, the cells C may be obtained from the blood of the immunized organism O. Alternatively, the cells C may be obtained from the lymph and/or spleen of the immunized organism O. Depending on the method used the organism O may be kept alive or may be sacrificed.

The antibodies AB of interest may be directly obtained from the cells C or may be obtained from further processed cells.

In a preferred embodiment, the method comprised the further step (v) of hybridizing the antibody-generating cells of step (iv) with myeloma cells obtaining immortalized antibody-generating cells C1. This may enable obtaining monoclonal antibodies. The person skilled in the art is well aware of methods usable for preparing such hybridoma cells C1.

In a preferred embodiment, the method comprised the further step (vi) of isolating the nucleotide encoding for the antibody AB of interest and transfer it to another antibody-generating cell type C2 suitible for expressing the antibody AB. This may enable heterologous expression of the antibody AB or fragments thereof. Optionally, also the Fc part of the antibody may be altered. Exemplarily, the antibody AB may than be humanized. The person skilled in the art is well aware of methods usable for this purpose. Further, the person skilled in the art will notice that the optional steps (v) and (vi) may optionally also be combined with another.

In any case, the antibody-generating cells C, C1 or C2 of any of steps (iv) to (vi) are cultivated under conditions enabling the production of the antibody AB followed by isolating the antibody AB. Such isolation step may be performed by any means such as, e.g., by means of chromatographic means such as affinity chromatography using a stationary phase comprising the antigen of the antibody AB.

In a further aspect, the present invention also embraces each of the antibody-generating cells C, C1 or C2.

It will be noted that the present invention also refers to an anti-repetitive organellar protein, putative of *Plasmodium falciparum* 3D7 or anti-hypothetical protein PVNG_04523 of *Plasmodium vivax* North Korean antibody.

Accordingly, a still further aspect of the present invention refers to an antibody or antibody fragment AB binding a polypeptide strand P of SEQ ID NO: 2 or SEQ ID NO: 3 or a polynucleotide strand encoding for said polypeptide strand P with a dissociation constant of not more than 1000 nM.

Preferably, the antibody or antibody fragment AB binding a polypeptide strand P of SEQ ID NO: 2 or SEQ ID NO: 3 or a polynucleotide strand encoding for said polypeptide strand P with a dissociation constant of not more than 100 nM, more preferably not more than 100 nM, even more preferably not more than 50 nM or not more than 20 nM.

As used in the context of the present invention, the term "antibody" may be understood in the broadest sense as any type of immunoglobulin or antigen-binding fraction or mutant thereof known in the art.

Exemplarily, the antibody of the present invention may be an immunoglobulin A (IgA), immunoglobulin D (IgD), immunoglobulin E (IgE), immunoglobulin G (IgG), immunoglobulin M (IgM), immunoglobulin Y (IgY) or immunoglobulin W (IgW). Preferably, the antibody is an IgA, IgG or IgD. More preferably, the antibody is an IgG. However, it will be apparent that the type of antibody may be altered by biotechnological means by cloning the gene encoding for the antigen-binding domains of the antibody of the present invention into a common gene construct encoding for any other antibody type.

The binding between the antibody and its molecular target structure (i.e., its antigen based on the polypeptide strand P of SEQ ID NO: 2 or SEQ ID NO: 3 or a polynucleotide strand encoding for said polypeptide strand P) typically is a non-covalent binding. Preferably, the binding affinity of the antibody to its antigen has a dissociation constant (Kd) of less than 1000 nM, less than 500 nM, less than 200 nM, less than 100 nM, less than 50 nM, less than 40 nM, less than 30 nM or even less than 20 nM.

The term "antibody" as used herein may be understood in the broadest sense and also includes what may be designated as an antibody mutant. As used in the context of the present invention, an antibody mutant may be understood in the broadest sense as any antibody mimetic or antibody with altered sequence known in the art. The antibody mutant may have at least 10%, at least 20%, at least 50%, at least 60%, at least 70%, at least 80%, at least 85%, at least 90% or at least 95% of the binding affinity of a corresponding antibody, i.e., bear a dissociation constant (Kd) of less than 10 μM, less than 1 μM, less than 500 nM, less than 200 nM, less than 100 nM, less than 50 nM, less than 40 nM, less than 30 nM or even less than 20 nM.

As used herein, the term "antibody fragment" may be understood in the broadest sense as any fragment of an antibody that still bears binding affinity to its molecular target (i.e., its antigen based on the polypeptide strand P of SEQ ID NO: 2 or SEQ ID NO: 3 or a polynucleotide strand encoding for said polypeptide strand P). Exemplarily, the antibody fragment may be a fragment antigen binding (Fab fragment), Fc, $F(ab')_2$, Fab', scFv, a truncated antibody comprising one or both complementarity determining region (s) (CDR(s)) or the variable fragment (Fv) of an antibody. Variable domains (Fvs) are the smallest fragments with an intact antigen-binding domain consisting of one $V_L$ and one $V_H$. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides. A recombinant antibody fragment is the single-chain Fv (scFv) fragment. Dissociation of scFvs results in monomeric scFvs, which can be complexed into dimers (diabodies), trimers (triabodies) or larger aggregates such as TandAbs and Flexibodies. The antibody may be a Fab, a Fab', a F(ab')2, a Fv, a disulfide-linked Fv, a scFv, a $(scFv)_2$, a bivalent antibody, a bispecific antibody, a multispecific antibody, a diabody, a triabody, a tetrabody or a minibody.

As mentioned above, the term "antibody" may also include an antibody mimetic which may be understood in the broadest sense as organic compounds that, like antibodies, can specifically bind antigens and that typically have a molecular mass in a range of from approximately 3 kDa to approximately 25 kDa. Antibody mimetics may be, e.g., affibody molecules (affibodies), affilins, affitins, anticalins, avimers, DARPins, Fynomers, Kunitz domain peptides, single-domain antibodies (e.g., VHH antibodies or VNAR antibodies, nanobodies), monobodies, diabodies, triabodies, flexibodies and tandabs. The antibody mimetics may be of natural origin, of gene technologic origin and/or of synthetical origin. The antibody mimetics may also include polynucleotide-based binding units. Optionally, the antibody may also be a CovX-body. Optionally, the antibody may also be a cameloid species antibody.

In a preferred embodiment, the antibody or antibody fragment AB binds to its antigen based on the polypeptide strand P of SEQ ID NO: 2 or SEQ ID NO: 3 or a polynucleotide strand encoding for said polypeptide strand P with an at least 10-fold, even more preferably at least 100-fold, even more preferably at least 1000-fold higher binding affinity than to the corresponding (i.e., sequence homologue) antigen of a polypeptide SEQ ID NO: 2 or SEQ ID NO: 3 or the respective polynucleotide strand encoding for said polypeptide.

The antibody or antibody fragment AB may be obtained by any means. In a preferred embodiment, the antibody or antibody fragment AB is obtained from a method of the present invention.

Optionally, the antibody of the present invention may be a monoclonal antibody, a chimeric antibody and/or a humanized antibody. Monoclonal antibodies are monospecific antibodies that are identical because they are produced by one type of immune cell that are all clones of a single parent cell. A chimeric antibody is an antibody in which at least one region of an immunoglobulin of one species is fused to another region of an immunoglobulin of another species by genetic engineering in order to reduce its immunogenicity. For example murine $V_L$ and $V_H$ regions may be fused to the remaining part of a human immunoglobulin. A particularly preferred type of chimeric antibodies are humanized antibodies. Humanized antibodies are produced by merging the DNA that encodes the CDRs of a non-human antibody with human antibody-producing DNA. The resulting DNA construct can then be used to express and produce antibodies that are usually not as immunogenic as the non-human parenteral antibody or as a chimeric antibody, since merely the CDRs are non-human.

In a preferred embodiment, the antibody or antibody fragment AB is a monoclonal humanized antibody.

Preferably, the antibody or antibody fragment AB bears a high affinity to the polypeptide strand P of SEQ ID NO: 2 or SEQ ID NO: 3. In a preferred embodiment, the antibody or antibody fragment AB bears a binding affinity to a polypeptide strand P of SEQ ID NO: 2 or SEQ ID NO: 3 of a dissociation constant of not more than 100 nM, not more than 50 nM, not more than 20 nM, not more than 10 nM, or not more than 5 nM.

The antibody or antibody fragment AB may be provided and stored in any suitable form. The antibody or antibody fragment AB, independent on its chemical nature, may optionally be dissolved in any medium suitable for storing said antibody such as, e.g., water, an aqueous buffer (e.g., a Hepes, Tris, or phosphate buffer (e.g. phosphate buffered saline (PBS)), an organic solvent (e.g., dimethyl sulfoxide (DMSO), dimethylformide (DMF)) or a mixture of two or more thereof. The antibody or mutant thereof according to the present invention may be of any species or origin. It may bind to any epitope(s) comprised by its molecular target structure (e.g., linear epitope(s), structural epitope(s), primary epitope(s), secondary epitope(s), e.g., based on SEQ ID NO: 2 or SEQ ID NO: 3 or a nucleotide encoding therefor). Preferably, the antibody or mutant thereof may recognize the naturally folded molecular target structure or a domain or fragment thereof (e.g., SEQ ID NO: 2 or SEQ ID NO: 3 or a nucleotide encoding therefor in its natural environment inside the plasmodia). The antibody or mutant thereof may be of any origin an antibody may be obtained from such as, e.g., natural origin, a gene technologic origin and/or a synthetic origin. Optionally, the antibody may also be commercially available. The person skilled in the art will understand that the antibody may further comprise one or more posttranscriptional modification(s) and/or may be conjugated to one or more further structures such as label moieties or cell-penetrating peptides (CPPs). Optionally, the antibody or antibody fragment may be added to a support, particularly a solid support such as an array, bead (e.g. glass or magnetic), a fiber, a film etc. The skilled person will be able to adapt the antibody of the present invention and a further component to the intended use by choosing a suitable further component.

Optionally, the antibody or antibody fragment AB may be conjugated with any kind of detectable label moiety. Then, the antibody or antibody fragment AB and the label moiety may be covalently or non-covalently conjugated with another, either directly of via a spacer.

As used throughout the present invention, the term "conjugated with" may be understood in the broadest sense as any kind of covalent or non-covalent attachment or linkage of one component with another component. Such conjugate can be obtained by chemical means and/or by genetic engineering and biotechnological means. The label moiety may be any moiety that is detectable, preferably detectable by an imaging method.

Exemplarily, the label moiety may be a fluorescent moiety. Exemplarily, a fluorescent moiety may be a fluorescent polypeptide moiety (e.g., cyan fluorescent protein (CFP), green fluorescent protein (GFP) or yellow fluorescent protein (YFP), red fluorescent protein (RFP), mCherry, etc.), a small-molecule dye moiety (e.g., an Atto dye moiety (e.g., ATTO 390, ATTO 425, ATTO 465, ATTO 488, ATTO 495, ATTO 520, ATTO 532, ATTO 550, ATTO 565, ATTO 590, ATTO 594, ATTO 610, ATTO 611X, ATTO 620, ATTO 633, ATTO 635, ATTO 637, ATTO 647, ATTO 647N, ATTO 655, ATTO 665, ATTO 680, ATTO 700, ATTO 725, ATTO 740), a Cy dye moiety (e.g., Cy3, Cy5, Cy5.5, Cy 7), an Alexa dye moiety (e.g., Alexa Fluor 488, Alexa Fluor 546, Alexa Fluor 647, Alexa Fluor 680, Alexa Fluor 750), a VisEn dye moiety (e.g. VivoTag680, VivoTag750), an S dye (e.g., S0387), a DyLight fluorophore moiety (e.g., DyLight 750, DyLight 800), an IRDye moiety (e.g., IRDye 680, IRDye 800), a fluorescein dye moiety (e.g., fluorescein, carboxyfluorescein, fluorescein isothiocyanate (FITC)), a rhodamine dye moiety (e.g., rhodamine, tetramethylrhodamine (TAMRA)), a HOECHST dye moiety, a quantum dot moiety or a combination of two or more thereof. Such fluorescent label moiety may be used in fluorescence microscopy.

Alternatively or additionally, the label moiety may be metal atom, metal ion or metal bead (e.g., a (colloidal) gold such as a gold bead). Such metal bead may be used in electron microscopy.

Alternatively or additionally, the label moiety may be radioactive label such as, e.g., $^{3}H$, $^{14}C$, $^{123}I$, $^{124}I$, $^{131}I$, $^{32}P$, $^{99m}Tc$ or lanthanides (e.g., $^{64}Gd$). In this context, a radioactive label may or may not be suitable for scintillation assays, computer tomography (CT), single-photon emission computed tomography (SPECT) or as a label suitable for Positron Emission Tomography (PET) (e.g., $^{11}C$, $^{13}N$, $^{15}O$, $^{18}F$, $^{82}Rb$).

As indicated above, the present invention also refers to the medicinal and non-medicinal uses of the antibody or antibody fragment AB of the present invention.

Accordingly, a still further aspect of the present invention refers to an antibody or antibody fragment AB of the present invention for use in a method for treating or preventing malaria in a patient.

The present invention refers to a method for treating or preventing malaria in a patient, said method comprising administration of antibody or antibody fragment AB of the present invention to said patient in an amount suitible for treating or preventing malaria in said patient.

Preferably, administration is systemic administration (e.g., intravenously (i.v.), intraarterially (i.a.), intraperitoneally (i.p.), intramusculary (i.m.), subcutaneously (s.c.), transdermally, nasally). Alternatively, administration may also be local administration (e.g., intrathecally or intravitreally). Preferably, administration is systemic administration, in particular intravenous injection. The administration frequency may be adapted to the individual patient. Administration may be performed once, twice, or more often or continuously (e.g., via drip). Exemplarily, administration may be performed three times daily, twice daily, or every two days or less often.

A still further aspect of the present invention refers to an antibody or antibody fragment AB for use in a method for diagnosing malaria in a patient.

In other words, the present invention refers to a method for diagnosing malaria in a patient, said method comprising administration of antibody or antibody fragment AB of the present invention to said patient in an amount suitible for detecting *Plasmodium falciparum* or *Plasmodium vivax* in said patient.

For detecting the antibody or antibody fragment AB used for diagnostic purposes, the antibody or antibody fragment AB is preferably labelled, i.e., conjugated to a label moiety, as described above.

The antibody or antibody fragment AB according to the present invention may also be used for staining in vitro.

For example, detection may be performed by enzyme-linked immunosorbent assay (ELISA), flow cytometry, fluorescence activated cell sorting (FACS), magnetic activated cell sorting (MACS), antibody-based dipsticks, etc.

Accordingly, a further aspect of the present invention relates to a method for staining *Plasmodium falciparum* or *Plasmodium vivax* in vitro, said method comprising the steps of:

(i) providing
  (a) an optionally fixed sample S containing *Plasmodium falciparum* or *Plasmodium vivax*, and
  (b) an optionally stained antibody or antibody fragment AB according to the present invention;
(ii) contacting the sample S with the optionally stained antibody or antibody fragment AB; and
(iii) optionally contacting the treated sample of step (ii) with a second antibody or antibody fragment AB2 which is stained and selectively binds to the antibody or antibody fragment AB.

When at least one of AB1 or AB2 is fluorescently labelled, the sample may be investigated by fluorescence microscopy of flow cytometry. Exemplarily, fluorescence microscopy may comprise one or more of the following methods: laser scanning microscopy (LSM), two-photon fluorescence microscopy, fluorescence molecular imaging (FMI), fluorescence energy transfer (FRET), fluorescence correlation spectroscopy (FCS), and/or fluorescence cross-correlation spectroscopy (FCCS). All these techniques as such are well-known to those skilled in the art. In the imaging step, the polypeptide strand P of SEQ ID NO: 1, SEQ ID NO: 2, SEQ IND NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16 or nucleotide encoding for at least one thereof may be fluorescently stained by a fluorescently labeled antibody AB1 or unlabeled AB1 in combination with labelled AB2. The excess fluorescently labeled antibody may be washed away and the localization and intensity is determined spatially resolved in the sample.

A still further aspect of the present invention refers to the (preferably in vitro) use of any of the polypeptides of the present invention as described herein (e.g. a polypeptide selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and/or SEQ ID NO: 16) for detecting *Plasmodium falciparum* or *Plasmodium vivax* in a patient's body fluid.

In a preferred embodiment, patient's body fluid is blood, blood plasm, blood serum or a fraction thereof.

A still further aspect of the present invention refers to a method of detecting *Plasmodium falciparum* or *Plasmodium vivax* (preferably in vitro), said method comprising the step of detecting the presence of any of the polypeptides of the present invention as described herein (e.g. a polypeptide selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and/or SEQ ID NO: 16) in a patient's body fluid. A further step may optionally be treating malaria in the patient accordingly.

A still further aspect of the present invention refers to a polypeptide of the present invention as described herein (e.g. a polypeptide selected from the group consisting of (SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and/or SEQ ID NO: 16) for use in a method for diagnosing a *Plasmodium falciparum* or *Plasmodium vivax* infection in a patient. Optionally the patient is further subjected to a malaria treatment.

A still further aspect of the present invention refers to a method of detecting *Plasmodium falciparum* or *Plasmodium vivax* (preferably in vitro), said method comprising the step of detecting the presence of an antibody specific for any of the polypeptides of the present invention as described herein (e.g. a polypeptide selected from the group consisting of SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and/or SEQ ID NO: 16) in a patient's body fluid. A further step may optionally be treating malaria in the patient accordingly.

A still further aspect of the present invention refers to an antibody specific for any of the polypeptides of the present invention as described herein (e.g. a polypeptide selected from the group consisting of (SEQ ID NO: 2, SEQ ID NO: 3, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and/or SEQ ID NO: 16) for use in a method for diagnosing a *Plasmodium falciparum* or *Plasmodium vivax* infection in a patient. Optionally the patient is further subjected to a malaria treatment.

A still further aspect of the present invention refers to a primer that is complementary to a fraction of any of SEQ ID NO: 4, SEQ ID NO: 5, or SEQ ID NO: 6 for detecting *Plasmodium falciparum* or *Plasmodium vivax* in a patient's body fluid.

In a preferred embodiment, the primer is a single chain nucleotide strand of a length of between five to 50 nucleotide moieties in length, between seven to 40 nucleotide moieties in length, between eight to 35 nucleotide moieties in length, or between nine to 30 nucleotide moieties in length.

A still further aspect of the present invention refers to a pair of primers that are both complementary to a fraction of any of SEQ ID NO: 4, SEQ ID NO: 5, or SEQ ID NO: 6 for detecting *Plasmodium falciparum* or *Plasmodium vivax* in a patient's body fluid.

A still further aspect of the present invention refers to a method of detecting *Plasmodium falciparum* or *Plasmodium vivax* (preferably in vitro) in a patient, said method comprising the steps of (i) contacting the nucleotides contained in a patient's body fluid with a pair of primers of which at least one is complementary to a fraction of any of SEQ ID NO: 4, SEQ ID NO: 5, or SEQ ID NO: 6;
(ii) conducting polymerase chain reaction (PCR) with the sample obtained in step (i); and
(iii) detecting the presence or absence of amplification product comprising the primers; and
(iv) optionally treating malaria in the patient accordingly.

A still further aspect of the present invention refers to a method of detecting *Plasmodium falciparum* or *Plasmodium vivax* (preferably in vitro) in a patient, said method comprising the steps of (i) contacting the nucleotides contained in a patient's body fluid with a pair of primers which are both complementary to a fraction of any of SEQ ID NO: 4, SEQ ID NO: 5, or SEQ ID NO: 6;
(ii) conducting polymerase chain reaction (PCR) with the sample obtained in step (i); and
(iii) detecting the presence or absence of amplification product comprising the primers; and
(iv) optionally treating malaria in the patient accordingly.

The Examples provided below and the claims illustrate further embodiments of the present invention.

EXAMPLES

Example 1

Protective Effect of the Immunization with Pch ROPE

Immunization experiment with Pch ROPE in Balb/c mice.

A cDNA library of a *Plasmodium chabaudi* 96V was constructed in pBluescript SK (Werner et al. 1998). From the cDNA library the recombinant plasmid pBluescript SK (−) 70 was isolated by screening. It contains part of the Pch ROPE sequence coding for amino acids 1283-1516 (234 amino acids) as an insert.

The insert was sub cloned in the pGEX-1T vector, transformed in *E. coli* JM 109 bacteria and expressed as a glutathione-S-transferase fusion protein in *E. coli* JM 109. The fusion protein was isolated using glutathione-agarose beads, followed by thrombin cleavage to obtain the 234 amino acid Pch ROPE protein fragment in a pure form, called rec 700.

Mice were immunized at day 0 and day 21 with:

7.5 μg rec 700
60 μg Alum
in 200 μl PBS pH 7.4

At day 35, mice were infected with $5 \times 10^6$ *Plasmodium chabaudi* 96V parasitized erythrocytes. Balb/c mice were immunized only two times and without any supplementation of an adjuvant such as muramyl peptide (MDP).

Results

All of the non-immunized mice died. 50% of the immunized Balb/c survived and 50% died. The fact that a high number of Balb/c mice survived an otherwise deadly infection with this extremely virulent *Plasmodium chabaudi* 96V strain using a weak immunization protocol, was surprising.

It is noteworthy in this context to mention that in other experiments, not a single untreated mouse survived an infection with the *Plasmodium chabaudi* 96V strain over a period of about four years of conducting regular experiments with this strain (Watier et al., 1992).

Particularly surprising was the finding that a protective effect of the immunization could still be observed when adjuvants like muramyl peptide (MDP) were omitted. Such adjuvants are typically considered to be a relevant component to illicit a stronger immune response against an antigen used as a vaccine.

Furthermore it was recently shown that, in the case of malaria, alum (used in above immunization) is a comparably poor adjuvant for fighting diseases like malaria (Leslie, 2013). This shows that ROPE is a particularly effective immunogen. It is indicating a very high protection capacity of the ROPE protein when used as a malaria vaccine. Moreover, ROPE is very effective for generating specific antibodies.

It will be understood that an infection with *Plasmodium chabaudi* in rodents is a well-established model system for infections with *Plasmodium falciparum* or *Plasmodium vivax* in humans. For this reason, it is reasonable to assume that ROPE has a protective effect for mammals (including humans) immunized with *Plasmodium falciparum* or *Plasmodium vivax* recombinant ROPE against infection with these parasites. As shown immunization was highly efficient. Ideally a single immunization step using a strong immunization protocol would be sufficient to confer protection.

Example 2

Further Development of a Pf ROPE or Pv ROPE Malaria Vaccine

Steps towards the development of a Pf ROPE or Pv ROPE malaria vaccine include generation and testing of antibodies against ROPE fragments, testing of antibodies against ROPE peptide-microarrays covering the entire ROPE sequence, and preclinical and clinical trials.

a.) Generation and Testing of Antibodies Against ROPE Fragments

Synthesizing parts of *Plasmodium falciparum* (Pf) ROPE as peptides, raising soluble scFvs (single chain fragment variable) antibodies against these peptides and testing the capacity to block invasion of human red blood cells by *Plasmodium falciparum* in vitro in culture. Antibodies showing the strongest inhibition will be used to produce antibodies that can be used for passive immunization in humans, similar to an anti-malaria drug.

Several peptides are produced from the Pf ROPE amino acid sequence. To analyze the Pf B cell epitopes, the Pf ROPE sequence was analyzed using the PROTEAN subroutine in the DNASTAR package. This subroutine uses (Wang et al., 2016):

Predicted alpha-regions (Gamier and Robson, 1989; Chou and Fasman, 1978)
Hydrophilicity (Kyte and Doolittle, 1982)
Flexibility (Karpus and Schulz, 1985)
Surface probability (Emini et al., 1985)
Antigenicity (Jameson and Wolf, 1988).

Based on this analysis the following peptides with good hydrophilicity, high accessibility, high flexibility, and strong antigenicity were selected as the antigen epitopes as shown in Table 1.

TABLE 1

Epitopes derived from ROPE

| Amino acid position in ROPE | Sequence | Length (amino acids) | Sequence No. |
|---|---|---|---|
| 331-356 | KQEKEKEKEKEREKEKEREKEKEKEY | 26 | SEQ ID NO: 7 |
| 420-447 | KNLKTELEKKEKELKDIENVSKEEINKL | 28 | SEQ ID NO: 8 |
| 520-560 | SKKEKEYNQYKNTYIEEINNLNEKLEE TNKEYTNLQNNYTN | 41 | SEQ ID NO: 9 |
| 812-840 | KEEYEDKMNTLNEQNEDKMNSLKEEY ENK | 29 | SEQ ID NO: 10 |
| 953-996 | KGLKKEVEEKEHKRHSSFNILKSKEKFF KNSIEDKSHELKKKHE | 44 | SEQ ID NO: 11 |
| 1050-1079 | KDKSKEKIKDKENQINVEKNEEKDLKKK DD | 30 | SEQ ID NO: 12 |
| 1277-1305 | EDEKKRNLNEINNLKKKNEDMCIKYNEMN | 29 | SEQ ID NO: 13 |
| 1452-1479 | KTNKENEEKIINLTSQYSDAYKKKSDES | 28 | SEQ ID NO: 14 |
| 1497-1521 | SNNNIRTNEYKYEEMFDTNIEEKNG | 25 | SEQ ID NO: 15 |
| 1581-1605 | GNISNKNENNNKKNNTCDGYDEKVT | 25 | SEQ ID NO: 16 |

It is reasonable that these peptides or fragments thereof are particularly suitable as a polypeptide strand P usable in a vaccine V.

Human antibodies are generated against above Pf ROPE peptides by phage display using human antibody gene libraries (Kügler et al. 2015).

In brief, biotinylated Pf ROPE peptides are immobilized on streptavidin coated microtiter plates. The libraries are incubated with the peptides, non-binding antibody phage particles removed by rigid washing steps. The bound antibody phages are eluted by trypsin and re-amplified using *E. coli* XL1-Blue and the M13-K07 helper phage. Subsequently, two further panning rounds are performed. Monoclonal antibodies are produced as soluble scFvs (single chain fragment variable) antibodies, using the phage display vector pHAL30 and identified by screening ELISA on the immobilized Pf ROPE peptides. This step is needed to discard non-specific binders of the corresponding antibody phage particles.

For further tests the monoclonal scFvs—single chain fragment variable-antibodies are re-cloned into the bivalent scFv-Fc format and produced in mammalian cells. The mammalian vector pCSE2.6-hIgG-Fc-XP and HEK293 6E cells are used. This is an IgG like bivalent molecule and also effector functions are established. (Jager et al., 2013). These IgG-like antibodies are used to test for their capacity to block invasion of human red blood cells by *Plasmodium falciparum* in vitro in culture. An in vitro growth inhibition activity assay (GIA) is used to measure the efficacy of the soluble scFvs antibodies directed against our peptides in blocking merozoite invasion (Kennedy et al., 2002).

Peptides identified as protective in the context of this in vitro inhibition can be used for the production of chemically synthesized vaccines, either as single peptides or as a fusion of several peptides or can be used as diagnostics.

b.) Testing of Antibodies Against ROPE Fragments in Microarrays

Peptide microarrays covering the entire Pf ROPE sequence are prepared. Sera from malaria patients are used to identify the immunodominant parts of the Pf ROPE protein during the course of an infection with *Plasmodium falciparum.*

The whole amino acid sequence of the target protein is retrieved from a public database and translated into 15-mer peptides with a peptide-peptide overlap of e.g. 12 amino acids. The peptide arrays with the corresponding peptides are produced by the company PEPperPRINT GmbH (Heidelberg, Germany) in a laser printing process on glass slides, coated with a PEGMA/PMMA graft copolymer, which are functionalized with a ßAla-ßAla-linker.

A layer of amino acid particles, containing Fmoc-amino acid pentafluorophenyl esters, is printed layer after layer onto the functionalized glass slides, with intermittent melting (i.e. coupling) steps at 90° C. and chemical washing and capping steps (Stadler et al., 2008), based on the same principle as Merrifield's solid-phase peptide synthesis. Peptides are generated in duplicates on the arrays, which are screened for IgG and IgM responses in human sera.

Therefore, peptide microarrays are placed in incubation trays (PEPperPRINT GmbH, Heidelberg, Germany) and blocked for 30 min at room temperature with western blot blocking buffer MB-070 (Rockland, USA). Then, sera are diluted 1:1000 in PBS buffer with 0.05% Tween 20 pH 7.4 (PBS-T) and 10% blocking buffer, incubating the sera for 16 h at 4° C. and 50 RPM orbital shaking. Peptide microarrays are washed three times shortly with PBS-T, followed by an incubation with a 1:2500 dilution of the secondary fluorescently labeled antibody, together with a control antibody for 30 min at room temperature. The peptide microarrays are washed with PBST and rinsed with deionized water. After drying in a stream of air, fluorescent images are acquired using an Odyssey Imaging System (LI-COR, USA) at 700 nm. Image analysis and quantification is performed with the PepSlide Analyzer software (Sicasys Software GmbH, Heidelberg, Germany).

c.) Further Preclinical and Clinical Trials with Recombinant Pf ROPE Protein

The result of this mapping will determine which part of the long Pf ROPE protein (1979 amino acids) will be expressed as a recombinant protein in *E. coli* and be used as an anti-malaria vaccine in *Aotus* monkeys and once proven to be efficient in human trials.

The DNA sequence coding for the entire Pf ROPE protein or parts of it is amplified by PCR of genomic Pf DNA and cloned into the pET-21a (+)-plasmid at the multiple cloning site (MCS). The MCS is under the control of a T7 promoter and flanked by a T7- and a HIS-tag. The recombinant pET-21a (+)-plasmid containing a sequence coding for Pf ROPE is transformed into *E. coli* BL21(DE3), a strain that allows high-efficiency protein expression of any gene that is under the control of a T7 promoter. The expressed recombinant Pf ROPE protein carries a histidine-tag at its C-terminus and is purified on a Nickel-column.

The recombinant Pf ROPE protein is mixed with a pharmaceutically acceptable carrier or excipient. A vaccine is obtained. This is applied to *Aotus* monkeys and once proven to be efficient in human trials.

REFERENCES

U.S. Pat. No. 8,716,443

Chou P Y, Fasman G D (1978) Prediction of the secondary structure of proteins from their amino acid sequence. Adv Enzymol 47:45-148.

Emini E A, Hughes J V, Perlow D S, Boger J (1985) Induction of hepatitis A virus-neutralizing antibody by virus specific synthetic peptide. J Virol 55:836-839

Gamier J, Robson B (1989) The GOR method for predicting secondary structures in proteins. In Fasman G D ed., Prediction of protein structure and the principles of protein conformation. New York, USA. Plenum Press. pp 417-465.

Jager V, Büssow K, Wagner A, Weber S, Hust M, Frenzel A and Schirrmann (2013) High level transient production of recombinant antibodies and antibody fusion proteins in HEK293 cells. BMC Biotechnology 13:52, 1472-6750/13/52

Jameson B A, Wolf (1988) The antigenic index: a novel algorithm for predicting antigenic determinants. Comput Appl Biosci 4(1):181-186

Kulangara, C., A. V. Kajava, G. Corradin, and I. Felger (2009) Sequence conservation in *Plasmodium falciparum* alpha-helical coiled coil domains proposed for vaccine development. PLoS One 4:e5419.

Karplus P A, Schulz G E. (1985) Prediction of chain flexibility in proteins: tool for the selection of peptide antigens. Naturwissenschaften 72:212-213.

Kennedy M C, Jin Wang, Yanling Zhang, Miles A P, Chitsaz F, Saul A, Long C A, Miller L H, Stowers A W (2002) In vitro studies with recombinant *Plasmodium falciparum* apical membrane antigen 1 (AMA1): Production and activity of an AMA1 vaccine and generation of a multi-allelic response. Infect Immun 70(12):6948-6960.

Kügler J, Wilke S, Meier D, Tomszak F, Frenzel A, Schirrmann T, Dübel S, Garritsen H, Hock B, Toleikis L, Schütte M, Hust M (2015) Generation and analysis of the improved human HAL9/10 antibody phage display libraries Biotechnology 15:10; DOI 10.1186/s12896-015-0125-0

Kyte J, Doolittle R F. (1982) A simple method for displaying the hydropathic character of a protein. J Mol Biol 157: 105-132.

Leslie, M. (2013) Solution to Vaccine Mystery Starts to Crystallize. Science 341:26-27

Stadler V et al. (2008) Combinatorial synthesis of peptide arrays with a laser printer. Angew. Chem. Int. Ed. Engl. 47(37):7132-7135

Topolska A E, Richie T L, Nhan D H, Coppel, R L. (2004), Associations between responses to the rhoptry-associated membrane antigen of *Plasmodium falciparum* and immunity to malaria infection. Infect Immun 72(6):3325-3330

Villard V, Agak G W, Frank G, Jafarshad A, Servis C, Servis C, Nébié I, Sirima S B, Felger I, Arevalo-Herrera M, Herrera S, Heitz F, Bäcker V, Druilhe P, Kajava A V, Corradin G (2007) Rapid identification of malaria vaccine candidates based on alpha-helical coiled coil protein motif. PLoS ONE, Issue 7, e645.

Wang Y, Wang G, Cai J P (2016) Identifying Novel B Cell Epitopes within Toxoplasma gondii GRA6. Korean J Parasitol. 54(4):431-437 (English. https://doi.org/10.3347/kjp.2016.54.4.431)

Watier H, Verwaerde C, Landau I, Werner E, Fontaine J, Capron A, Auriault C (1992). T-cell dependent immunity and thrombocytopenia in rats infected with *Plasmodium chabaudi*. Infect Immune, 60:136-142

Werner E B E, William W R Taylor, Holder A A. (1998) A *Plasmodium chabaudi* protein contains a repetitive region with a predicted spectrin-like structure. Mol Biochem Parasitol. 94:185-196.

The invention claimed is:

1. An antigenic composition comprising:

(A) at least one isolated polypeptide (P) consisting of up to 50 amino acids inclusive of an antigenic epitope having the amino acid sequence according to SEQ ID NO: 8; and (B) at least one pharmaceutically acceptable carrier or excipient.

2. The antigenic composition of claim 1, wherein the isolated polypeptide (P) is obtained from heterologous expression in bacterial or eukaryotic cells.

3. The antigenic composition of claim 1, wherein the antigenic composition comprises an adjuvant supporting immunologic stimulation.

4. The antigenic composition of claim 1, wherein the antigenic composition comprises at least one adjuvant supporting immunologic stimulation selected from the group consisting of alum and an immunostimulatory peptide.

5. The antigenic composition of claim 1, wherein the at least one isolated polypeptide is expressed by a double stranded DNA polynucleotide, a single stranded DNA polynucleotide, a double stranded RNA polynucleotide, a single stranded RNA polynucleotide, or an analogue of any one of the foregoing polynucleotides.

6. A method for developing an immune response against *Plasmodium falciparum* or *Plasmodium vivax* malaria in a patient, the method comprising administering a sufficient amount of the antigenic composition of claim 1 to the patient.

7. A method for preparing an antibody binding to *Plasmodium falciparum* or *Plasmodium vivax* comprising the following steps:

(i) providing:

(a) an antigenic composition according to claim 1, and (b) an organism suitable for generating antibodies;

(ii) administering the organism with the antigenic composition;

(iii) waiting until the subjected organism of step (ii) shows an immune response against the antigens of the antigenic composition;

(iv) obtaining antibody-generating cells (C) of the organism of step (iii);

(v) optionally hybridizing the antibody-generating cells of step (iv) with myeloma cells obtaining immortalized antibody-generating cells (C1);

(vi) optionally isolating the nucleotide encoding for the antibody of interest and transferring it to another antibody-generating cell type (C2) suitable for expressing the antibody;

(vii) cultivating the antibody-generating cells C, C1, or C2 of any of steps (iv) to (vi) under conditions enabling the production of the antibody; and (viii) isolating the antibody from step (vii).

8. The antigenic composition of claim 1, wherein the up 50 amino acids is further inclusive of one or more further antigenic epitopes selected from SEQ ID NOs: 7 and 9-16.

* * * * *